(12) United States Patent
Alabi et al.

(10) Patent No.: US 9,895,443 B2
(45) Date of Patent: Feb. 20, 2018

(54) MULTI-TAILED LIPIDS AND USES THEREOF

(71) Applicant: Massachusetts Institute of Technology, Cambridge, MA (US)

(72) Inventors: Akinleye C. Alabi, Ithaca, NY (US); Kevin Thomas Love, Boston, MA (US); Daniel Griffith Anderson, Framingham, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 178 days.

(21) Appl. No.: 14/900,869

(22) PCT Filed: Jun. 26, 2014

(86) PCT No.: PCT/US2014/044408
§ 371 (c)(1),
(2) Date: Dec. 22, 2015

(87) PCT Pub. No.: WO2014/210356
PCT Pub. Date: Dec. 31, 2014

(65) Prior Publication Data
US 2016/0158363 A1    Jun. 9, 2016

Related U.S. Application Data

(60) Provisional application No. 61/839,616, filed on Jun. 26, 2013.

(51) Int. Cl.
| | |
|---|---|
| *A61K 47/22* | (2006.01) |
| *C07C 323/12* | (2006.01) |
| *C07D 207/09* | (2006.01) |
| *C07D 295/15* | (2006.01) |
| *C12N 15/113* | (2010.01) |
| *A61K 9/127* | (2006.01) |

(52) U.S. Cl.
CPC ............ *A61K 47/22* (2013.01); *C07C 323/12* (2013.01); *C07D 207/09* (2013.01); *C07D 295/15* (2013.01); *C12N 15/113* (2013.01); *C12N 15/1137* (2013.01); *A61K 9/127* (2013.01); *C12N 2310/14* (2013.01); *C12N 2320/32* (2013.01)

(58) Field of Classification Search
CPC ...... A61K 9/127; A61K 47/22; C07C 323/12; C07D 207/09; C07D 295/15
See application file for complete search history.

(56) References Cited

U.S. PATENT DOCUMENTS

| | | |
|---|---|---|
| 2011/0293703 A1 | 12/2011 | Mahon et al. |
| 2012/0128760 A1 | 5/2012 | Manoharan et al. |

FOREIGN PATENT DOCUMENTS

EP      2 532 649      12/2012

OTHER PUBLICATIONS

International Search Report and Written Opinion for PCT/US2014/044408, dated Oct. 24, 2014.
International Preliminary Report on Patentability for PCT/US2014/044408, dated Jan. 7, 2016.
Akinc et al., A combinatorial library of lipid-like materials for delivery of RNAi therapeutics. Nat Biotech. 2008;26(5):561-69.

*Primary Examiner* — Kendra D Carter
(74) *Attorney, Agent, or Firm* — Wolf, Greenfield & Sacks, P.C.

(57) ABSTRACT

The present invention provides multi-tailed lipid compounds, and salts and stereoisomers thereof, and methods of preparing the compounds. Also provided are compositions including a compound of the invention and an agent (e.g., an siRNA, mRNA, plasmid DNA, small molecule, protein, peptide). The present invention also provides methods, and kits using the compositions for delivering an agent to a subject (e.g., to the liver, spleen, or lung of the subject) or cell and for treating and/or preventing a range of diseases, such as genetic diseases, proliferative diseases, hematological diseases, neurological diseases, immunological diseases, gastrointestinal diseases (e.g., liver diseases), respiratory diseases (e.g., lung diseases), painful conditions, psychiatric disorders, metabolic disorders, and spleen diseases.

34 Claims, 22 Drawing Sheets

MULTI-TAILED LIPIDS AND USES THEREOF

RELATED APPLICATIONS

The present application is a national stage filing under 35 U.S.C. § 371 of international PCT application, PCT/US2014/044408, filed Jun. 26, 2014, which claims priority under 35 U.S.C. § 119(e) to U.S. provisional patent application, U.S. Ser. No. 61/839,616 filed Jun. 26, 2013, each of which is incorporated herein by reference.

GOVERNMENT SUPPORT

This invention was made with U.S. Government support under Grant No. R37-EB000244 awarded by the National Institutes of Health. The U.S. government has certain rights in this invention.

BACKGROUND OF THE INVENTION

The ability to silence genes via RNA interference (RNAi) was reported by Mello and Fire in 1998. See Fire et al., *Nature* (1998) 391:806-811. Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans*. See Davis et al., *Nature* (2010) 464: 1067-1070. The advantages of siRNA therapeutics include high target selectivity and specificity, and the potential to target pathways currently believed to be "undruggable" for the treatment of genetic diseases without effective therapy. siRNA therapeutics has shown promising results for the treatment of various diseases, such as hepatic carcinoma, hypercholesterolemia, refractory anemia, and familial amyloid neuropathy.

However, the efficient delivery of siRNA is still a challenge in the development of siRNA therapeutics. Due to issues associated with delivery efficiency and toxicity, the clinical use of siRNA requires safer and more effective delivery systems. It is understood that the development of genetic drugs is slowed by the inability to deliver nucleic acids effectively in vivo. When unprotected, genetic materials injected into the bloodstream can be degraded by deoxyribonucleases (DNAases) and ribonucleases (RNAases), or, if not degraded, the genetic materials can stimulate an immune response. See, e.g., Whitehead et al., *Nature Reviews Drug Discovery* (2009) 8:129-138; Robbins et al., *Oligonucleotides* (2009) 19:89-102. Intact siRNA must then enter the cytosol, where the antisense strand is incorporated into the RNA-induced silencing complex (RISC) (Whitehead et al., supra). The RISC associates with and degrades complementary mRNA sequences, thereby preventing translation of the target mRNA into protein, i.e., "silencing" the gene.

To overcome difficulties in delivery, polynucleotides have been complexed with a wide variety of delivery systems, including polymers, lipids, inorganic nanoparticles, and viruses. See, e.g., Peer et al., *Nature Nanotechnology*, (2007) 2:751-760. However, despite promising data from ongoing clinical trials for the treatment of respiratory syncytial virus infection and liver cancers (see, e.g., Zamora et al., *Am. J. Respir. Crit. Care Med.* (2011) 183:531-538), the clinical use of siRNA continues to require development of safer and more effective delivery systems. Toward this end, numerous lipid-like molecules have been developed including poly β-amino esters and amino alcohol lipids. See, e.g., International PCT Patent Application Publications, WO 2002/031025, WO 2004/106411, WO 2008/011561, WO 2007/143659, WO 2006/138380, WO 2010/053572, WO 2013/063468. Amino acid, peptide, polypeptide-lipids have also been studied for a variety of applications, including use as therapeutics, biosurfactants, and nucleotide delivery systems. See, e.g., Giuliani et al., *Cellular and Molecular Life Sciences* (2011) 68:2255-2266; Ikeda et al., *Current Medicinal Chemistry* (2007) 14: 111263-1275; Sen, *Advances in Experimental Medicine and Biology* (2010) 672:316-323; and Damen et al., *Journal of Controlled Release* (2010) 145:33-39.

Encapsulation of siRNAs within nanoparticles offers numerous delivery benefits, including protection from degradation by ubiquitous nucleases, passive and active targeting, and evasion of endosomal Toll-like receptors (1-9). To date, several polymeric, lipid, and dendritic nanoparticles have been developed for the encapsulation and delivery of siRNAs (1, 3, 5, 7-15). Despite the delivery successes met by some of these carriers, challenges to efficient delivery exist, including nanoparticle dissociation via serum proteins, cellular uptake, endosomal escape, and appropriate intracellular disassembly. To address some of these challenges, single parameter studies that evaluate the effect of chemical structure on a single biological property or on delivery performance have been reported (10-17). Furthermore, high-throughput synthetic methods have been exploited for the accelerated discovery of potent lipid nanoparticles (LNP) and evaluation of structure activity relationships (SARs) (16-20). In spite of these efforts, the relationships between physicochemical properties of nanoparticles and biological barriers, and that between biological barriers and gene silencing activity remain unclear. This lack of clarity has also resulted in poor in vitro-in vivo translation.

Therefore, there remains the need for new materials and systems for the delivery of siRNAs, other nucleic acids, and other agents to cells.

SUMMARY OF THE INVENTION

The present invention provides novel compounds and uses thereof. The compounds of the invention are multi-tailed lipids and are able to form lipid nanoparticles (LNPs), microparticles, micelles, liposomes, lipoplexes, and other forms. Also provided are compositions (e.g., pharmaceutical compositions) including a compound of the invention and an agent (e.g., an siRNA, mRNA, plasmid DNA, small molecule, protein, peptide). The present invention also provides methods and kits using the compositions for delivering an agent to a subject (e.g., to the liver, spleen, or lung of the subject) or cell and for treating and/or preventing a range of diseases, such as genetic diseases, proliferative disease, hematological diseases, neurological diseases, immunological diseases, gastrointestinal diseases (e.g., liver diseases), respiratory diseases (e.g., lung diseases), painful conditions, psychiatric disorders, metabolic disorders, and spleen diseases.

In one aspect, the invention provides compounds of Formula (I):

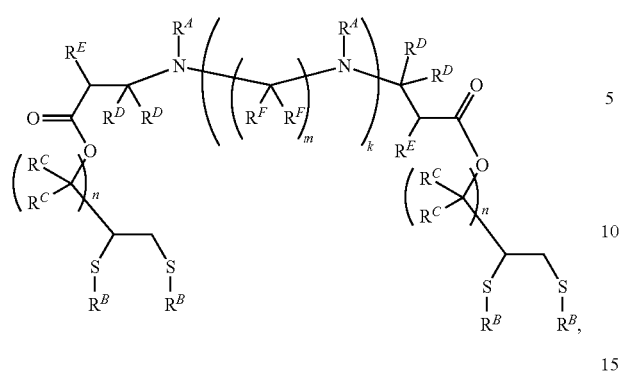
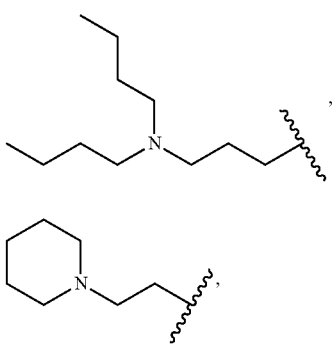
and salts and stereoisomers thereof, wherein $R^A$, $R^B$, $R^C$, $R^D$, $R^E$, $R^F$, k, m, and n are as described herein.
Exemplary compounds of Formula (I) include, but are not limited to compounds of any one of Formulae (I-1) to (I-31):
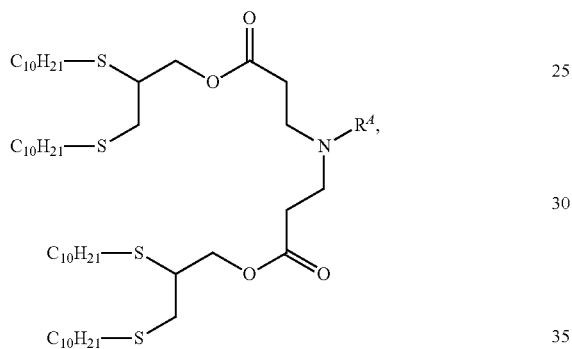
wherein $R^A$ is one of the formulae:
(I-1)
(I-2)
(I-3)
(I-4)
(I-5)
(I-6)
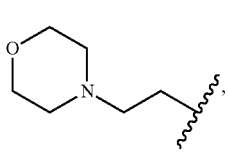
(I-7)
(I-8)
(I-9)
(I-10)
(I-11)
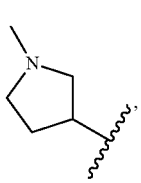
(I-12)
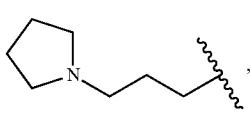
(I-13)
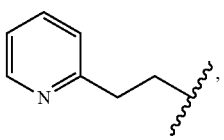
(I-14)
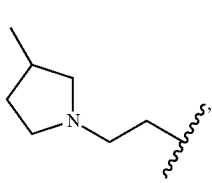
(I-15)
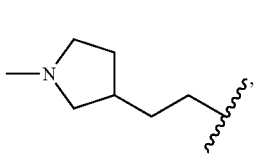

(I-16) 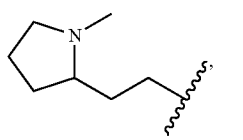

(I-17) 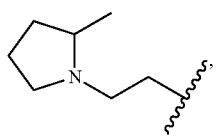

(I-18) 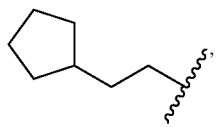

(I-19) 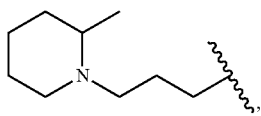

(I-20) 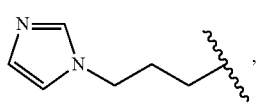

(I-21) 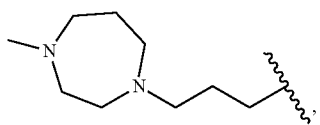

(I-22) 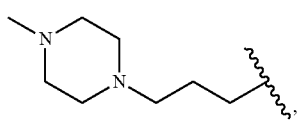

(I-23) 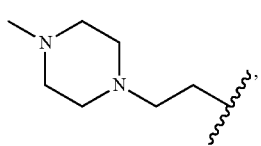

(I-24) 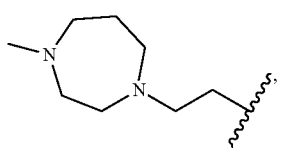

(I-25) 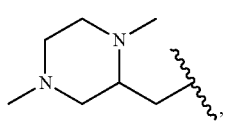

(I-26) n-Bu, 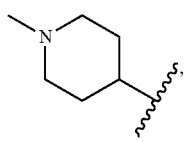

(I-27)

(I-28) 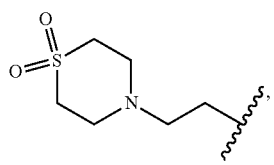

(I-29) 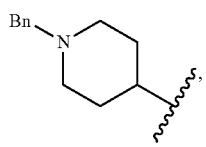

(I-30) 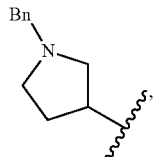

(I-31) 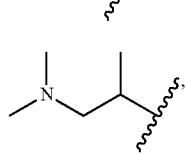

and salts and stereoisomers thereof.

A particular exemplary compound of Formula (I) is of Formula (I-32):

(I-32)

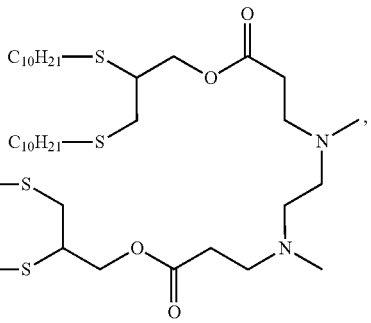

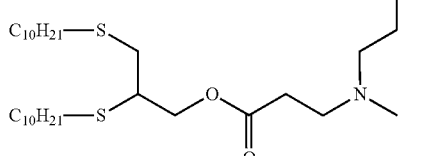

or a salt or stereoisomer thereof.

In yet another aspect, the present invention provides compositions (e.g., pharmaceutical compositions) comprising a compound of the invention, an agent (e.g., an agent, such as a polynucleotide), and optionally an excipient (e.g., a pharmaceutically acceptable excipient). Without wishing to be bound by any particular theory, the inventive compositions are thought to be useful for delivering the agent to a subject (e.g., to the liver, spleen, or lung of the subject) or cell. Without wishing to be bound by any particular theory, a compound of the invention, which includes more than one amino moiety (e.g., —$NR^A$— moieties of a compound of Formula (I)) that may be protonated to form positively charged ammonium cations, may bind to an agent that includes negatively charged moieties, such as a polynucleotide, to form a complex. A compound of the invention also typically includes more than one unsubstituted or substituted alkyl moiety (e.g., $R^B$ moieties of a compound of Formula (I)), which is hydrophobic and may assist the inventive compound and/or the complex of the inventive compound and the agent to pass through cell membranes or be taken up by cells. An inventive composition including a compound of the invention may be in the form of particles (e.g., nanoparticles, microparticles) because a plurality of molecules of the inventive compound may aggregate to form particles. In certain embodiments, the $R^A$ moieties of a compound of Formula (I), or a salt or stereoisomer thereof, are substantially within the inner portion of a particle described herein. In certain embodiments, the $R^B$ moieties of a compound of Formula (I), or a salt or stereoisomer thereof, are substantially on the outer portion of a particle described herein. An agent may be encapsulated within the inner portion of the particle described herein and may get transported through (e.g., into or out of a cell) the cell membranes. The particle may dissociate and release the agent to a cell (e.g., a target cell) or tissue (e.g., a target tissue).

The compositions of the invention (e.g., pharmaceutical compositions) may also be useful in treating and/or preventing a range of diseases (e.g., genetic diseases, proliferative diseases, hematological diseases, neurological diseases, immunological diseases, gastrointestinal diseases (e.g., liver diseases), respiratory diseases (e.g., lung diseases), painful conditions, psychiatric disorders, metabolic disorders, and spleen diseases) in a subject in need thereof. In certain embodiments, a composition of the invention includes an effective amount of the agent. The inventive compositions may also be useful in treating and/or preventing a disease, such as a genetic disease, a proliferative disease, a hematological disease, a neurological disease, an immunological disease, a gastrointestinal disease (e.g., liver disease), a respiratory disease (e.g., lung disease), a painful condition, a psychiatric disorder, a metabolic disorder, or a spleen disease. In certain embodiments, the inventive compositions are useful in treating and/or preventing hepatic carcinoma, hypercholesterolemia, refractory anemia, or familial amyloid neuropathy.

Another aspect of the present invention relates to methods of delivering an agent to a subject, tissue (e.g., a target tissue, such as the liver, spleen, or lung of a subject), or cell (e.g., a target cell, such as a liver cell, spleen cell, or lung cell). The cell may be in vitro, ex vivo, or in vivo. In certain embodiments, the method of delivering an agent comprises administering a composition of the invention to a subject or cell. The cell may be in vitro, ex vivo, or in vivo. In certain embodiments, the agent is selectively delivered to a target tissue or target cell, as opposed to a non-target tissue or non-target cell.

Another aspect of the invention relates to methods of increasing the exposure of an agent to a subject, tissue (e.g., a target tissue), or cell (e.g., a target cell).

Another aspect of the invention relates to methods of increasing the concentration of an agent in a subject or cell.

In another aspect, the present invention provides methods of treating and/or preventing a disease, such as a genetic disease, a proliferative disease, a hematological disease, a neurological disease, an immunological disease, a gastrointestinal disease (e.g., liver disease), a respiratory disease (e.g., lung disease), a painful condition, a psychiatric disorder, a metabolic disorder, or a spleen disease in a subject in need thereof. In certain embodiments, the disease that is treated and/or prevented by the inventive methods is hepatic carcinoma, hypercholesterolemia, refractory anemia, or familial amyloid neuropathy. In certain embodiments, the method of treating and/or preventing a disease comprises administering a composition of the invention to the subject.

Another aspect of the invention relates to methods of screening a library of compounds of Formula (I) to identify one or more compounds that are useful in the methods of the invention. The identified compound may be useful for delivering an agent (e.g., a polynucleotide, peptide, protein, small molecule) to a subject (e.g., to the liver, spleen, or lung of the subject) or cell. The identified compound may also be useful in treating and/or preventing a disease described herein.

In yet another aspect, the present invention provides compositions described herein for use in delivering an agent to a subject (e.g., to the liver, spleen, or lung of the subject) or cell. In certain embodiments, the present invention provides compositions described herein for use in treating and/or preventing a disease in a subject in need thereof.

Another aspect of the present invention relates to methods of preparing compounds of Formula (I), and salts and stereoisomers thereof, the method includes the Michael addition of an α,β-unsaturated ester containing an ethynyl moiety (e.g., a compound of Formula (A), or a salt thereof), with a primary or secondary amine (e.g., a compound of Formula (B), or a salt thereof), followed by a thiol-yne "click" photoaddition. In certain embodiments, the method of preparing compounds of Formula (I) includes (a) reacting a compound of Formula (A), or a salt thereof, with a compound of Formula (B), or a salt thereof, to provide a compound of Formula (C), or a salt thereof:

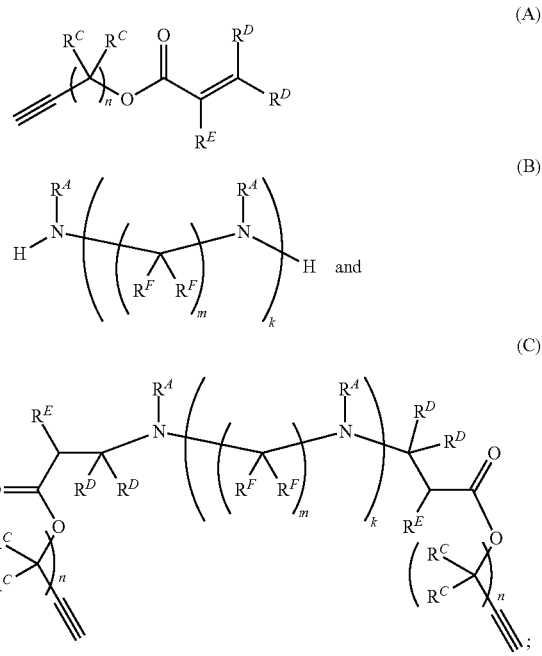

(b) reacting the compound of Formula (C), or a salt thereof, with a compound of Formula (D), or a salt thereof, to provide the compound of Formula (I), or salt or stereoisomer thereof:

wherein $R^A$, $R^B$, $R^C$, $R^D$, $R^E$, $R^F$, k, m, and n are as described herein.

Another aspect of the present invention relates to kits comprising a container with a composition of the invention. The kits of the invention may include a single dose or multiple doses of the composition. The provided kits may be useful in delivering an agent to a agent to a subject (e.g., to the liver, spleen, or lung of the subject) or cell. The provided kits may also be useful in in treating and/or preventing a disease in a subject in need thereof. In certain embodiments, the kit further includes instructions for administering the composition to the subject (e.g., as required by a regulatory agency).

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is unspecified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "heteroaliphatic" refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholinyl, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_R$(CO)R$_R$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix—ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{bb}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{bb}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$alkyl), —C(=NH)NH$_2$, —OC(=NH)N(C$_{1-6}$alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, C$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2- sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{aa}$, —SOR$^{aa}$, —C(=S)N(R$^{cc}$)$_2$, —C(=O)SR, —C(=S)SR$^{cc}$, —P(=O)$_2$R$^{aa}$, —P(=O)(R$^{bb}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamante, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=NR)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)($OR^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2$R$^{aa}$, —P(=O)(R$^{aa}$)$_2$, —P(=O)(OR), —P(=O)$_2$N(R$^{bb}$)$_2$, and —P(=O)(NR$^{bb}$)$_2$, wherein R$^{aa}$, R$^{bb}$, and R$^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The invention is not intended to be limited in any manner by the above exemplary listing of substituents.

Other Definitions

The following definitions are more general terms used throughout the present application.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the invention. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched C$_{1-24}$ alkyl. In certain embodiments, the lipophilic moiety is unsubstituted and unbranched C$_{6-24}$ alkyl. In certain embodiments, the lipophilic moiety is unsubstituted and unbranched C$_{12-24}$ alkyl.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

A "large organic molecule" or "large molecule" refers to an organic compound that is not a small molecule. In certain embodiments, the molecular weight of a large molecule is greater than about 2,000 g/mol, greater than about 3,000 g/mol, greater than about 4,000 g/mol, or greater than about 5,000 g/mol. In certain embodiments, the molecular weight of a large molecule is at most about 100,000 g/mol, at most about 30,000 g/mol, at most about 10,000 g/mol, at most about 5,000 g/mol, or at most about 2,000 g/mol. Combinations of the above ranges (e.g., greater than about 2,000 g/mol and at most about 10,000 g/mol) are also possible. In certain embodiments, the large molecule is a therapeutically active agent such as a drug (e.g., a molecule approved by the U.S. Food and Drug Administration as provided in the Code of Federal Regulations (C.F.R.)). The large molecule may also be complexed with one or more metal atoms and/or metal ions. In this instance, the large molecule is also referred to as an "large organometallic compound."

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature*, 290, 304-310, (1981); Yamamoto et al., *Cell*, 22, 787-797, (1980); Wagner et al., *Proc. Natl. Acad. Sci. U.S.A.* 78, 1441-1445, (1981); Brinster et al., *Nature* 296, 39-42, (1982)). Any type of plasmid, cosmid, yeast artificial chromosome or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design. Examples of recombinant nucleic acid molecule include recombinant vectors, such as cloning or expression vectors which contain DNA sequences encoding Ror family proteins or immunoglobulin proteins which are in a 5' to 3' (sense) orientation or in a 3' to 5' (antisense) orientation.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle. A crystalline nanoparticle is referred to as a "nanocrystal."

The term "microparticle" refers to a particle having a characteristic dimension of less than about 1 millimeter and at least about 1 micrometer, where the characteristic dimension of the particle is the smallest cross-sectional dimension of the particle.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The terms "administer," "administering," or "administration" refers to implanting, absorbing, ingesting, injecting, inhaling, or otherwise introducing an inventive compound, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barre syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as Pernicious Anemia, Hemorrhagic Anemia, Hemolytic Anemia, Aplastic Anemia, Sickle Cell Anemia, Sideroblastic Anemia, Anemia associated with chronic infections such as Malaria, Trypanosomiasis, HIV, Hepatitis virus or other viruses, Myelophthisic Anemias caused by marrow deficiencies, renal failure resulting from Anemia, Anemia, Polycethemia, Infectious Mononucleosis (EVI), Acute Non-Lymphocytic Leukemia (ANLL), Acute Myeloid Leukemia (AML), Acute Promyelocytic Leukemia (APL), Acute Myelomonocytic Leukemia (AMMoL), Polycethemia Vera, Lymphoma, Acute Lymphocytic Leukemia (ALL), Chronic Lymphocytic Leukemia, Wilm's Tumor, Ewing's Sarcoma, Retinoblastoma, Hemophilia, disorders associated with an increased risk of Thrombosis, Herpes, Thalessemia, antibody-mediated disorders such as transfusion reactions and Erythroblastosis, mechanical trauma to red blood cells such as micro-angiopathic hemolytic anemias, Thrombotic Thrombocytopenic Purpura and disseminated intravascular coagulation, infections by parasites such as Plasmodium, chemical injuries from, e.g., lead poisoning, and Hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases also refer to a type of neurological disease marked by the loss of nerve cells, including, but not limited to, Alzheimer's disease, Parkinson's disease, amyotrophic lateral sclerosis, tauopathies (including fronto-temporal dementia), and Huntington's disease. Examples of neurological diseases include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include Acquired Epileptiform Aphasia; Acute Disseminated Encephalomyelitis; Adrenoleukodystrophy; Agenesis of the corpus callosum; Agnosia; Aicardi syndrome; Alexander disease; Alpers' disease; Alternating hemiplegia; Alzheimer's disease; Amyotrophic lateral sclerosis; Anencephaly; Angelman syndrome; Angiomatosis; Anoxia; Aphasia; Apraxia; Arachnoid Cysts; Arachnoiditis; Arnold-Chiari malformation; Arteriovenous malformation; Asperger syndrome; Ataxia Telangiectasia; Attention Deficit Hyperactivity Disorder; Autism; Autonomic Dysfunction; Back Pain; Batten disease; Behcet's disease; Bell's palsy; Benign Essential Blepharospasm; Benign Focal; Amyotrophy; Benign Intracranial Hypertension; Binswanger's disease; Blepharospasm; Bloch Sulzberger syndrome; Brachial plexus injury; Brain abscess; Brain injury; Brain tumors (including Glioblastoma multiforme); Spinal tumor; Brown-Sequard syndrome; Canavan disease; Carpal tunnel syndrome (CTS); Causalgia; Central pain syndrome; Central pontine myelinolysis; Cephalic disorder; Cerebral aneurysm; Cerebral arteriosclerosis; Cerebral atrophy; Cerebral gigantism; Cerebral palsy; Charcot-Marie-Tooth disease; Chemotherapy-induced neuropathy and neuropathic pain; Chiari malformation; Chorea; Chronic inflammatory demyelinating polyneuropathy (CIDP); Chronic pain; Chronic regional pain syndrome; Coffin Lowry syndrome; Coma, including Persistent Vegetative State; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dancing eyes-dancing feet syndrome; Dandy-Walker syndrome; Dawson disease; De Morsier's syndrome; Dejerine-Klumpke palsy; Dementia; Dermatomyositis; Diabetic neuropathy; Diffuse sclerosis; Dysautonomia; Dysgraphia; Dyslexia; Dystonias; Early infantile epileptic encephalopathy; Empty sella syndrome; Encephalitis; Encephaloceles; Encephalotrigeminal angiomatosis; Epilepsy; Erb's palsy; Essential tremor; Fabry's disease; Fahr's syndrome; Fainting; Familial spastic paralysis; Febrile seizures; Fisher syndrome; Friedreich's ataxia; Fronto-Temporal Dementia and other "Tauopathies"; Gaucher's disease; Gerstmann's syndrome; Giant cell arteritis; Giant cell inclusion disease; Globoid cell Leukodystrophy; Guillain-Barre syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; HIV-Associated Dementia and Neuropathy (see also Neurological manifestations of AIDS); Holoprosencephaly; Huntington's disease and other polyglutamine repeat diseases; Hydranencephaly; Hydrocephalus; Hypercortisolism; Hypoxia; Immune-Mediated encephalomyelitis; Inclusion body myositis; Incontinentia pigmenti; Infantile; phytanic acid storage disease; Infantile Refsum disease; Infantile spasms; Inflammatory myopathy; Intracranial cyst; Intracranial hypertension; Joubert syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (aka Motor Neuron Disease or Amyotrophic Lateral Sclerosis); Lumbar disc disease; Lyme disease-Neurological Sequelae; Machado-Joseph disease; Macrencephaly; Megalencephaly; Melkersson-Rosenthal syndrome; Menieres disease; Meningitis; Menkes disease; Metachromatic leukodystrophy; Microcephaly; Migraine; Miller Fisher syndrome; Mini-Strokes; Mitochondrial Myopathies; Mobius syndrome; Monomelic amyotrophy; Motor Neurone Disease; Moyamoya disease; Mucopolysaccharidoses; Multi-Infarct Dementia; Multifocal motor neuropathy; Multiple sclerosis and other demyelinating disorders; Multiple system atrophy with postural hypotension; Muscular dystrophy; Myasthenia gravis; Myeloclastic diffuse sclerosis; Myoclonic encephalopathy of infants; Myoclonus; Myopathy; Myotonia congenital; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; O'Sullivan-McLeod syndrome; Occipital Neuralgia; Occult Spinal Dysraphism Sequence; Ohtahara syndrome; Olivopontocerebellar Atrophy; Opsoclonus Myoclonus; Optic neuritis; Orthostatic Hypotension; Overuse syndrome; Paresthesia; Parkinson's disease; Paramyotonia Congenita; Paraneoplastic diseases; Paroxysmal attacks; Parry Romberg syndrome; Pelizaeus-Merzbacher disease; Periodic Paralyses; Peripheral Neuropathy; Painful Neuropathy and Neuropathic Pain; Persistent Vegetative State; Pervasive developmental disorders; Photic sneeze reflex; Phytanic Acid Storage disease; Pick's disease; Pinched Nerve; Pituitary Tumors; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive; Hemifacial Atrophy; Progressive multifocal leukoencephalopathy; Progressive Sclerosing Poliodystrophy; Progressive Supranuclear Palsy; Pseudotumor cerebri; Ramsay-Hunt syndrome (Type I and Type II); Rasmussen's Encephalitis; Reflex Sympathetic Dystrophy syndrome; Refsum disease; Repetitive Motion Disorders; Repetitive Stress Injuries; Restless Legs syndrome; Retrovirus-Associated Myelopathy; Rett syndrome; Reye's syndrome; Saint Vitus Dance; Sandhoff disease; Schilder's disease; Schizencephaly; Septo-Optic Dysplasia; Shaken Baby syndrome; Shingles; Shy-Drager syndrome; Sjogren's syndrome; Sleep Apnea; Soto's syndrome; Spasticity; Spina *bifida*; Spinal cord injury; Spinal cord tumors; Spinal Muscular Atrophy; Stiff-Person syndrome; Stroke; Sturge-Weber syndrome; Subacute Sclerosing Panencephalitis; Subarachnoid Hemorrhage; Subcortical Arteriosclerotic Encephalopathy; Sydenham Chorea; Syncope; Syringomyelia; Tardive dyskinesia; Tay-Sachs disease; Temporal arteritis; Tethered Spinal Cord syndrome; Thomsen disease; Thoracic Outlet syndrome; Tic Douloureux; Todd's Paralysis; Tourette syndrome; Transient ischemic attack; Transmissible Spongiform Encephalopathies; Transverse myelitis; Traumatic Brain injury; Tremor; Trigeminal Neuralgia; Tropical Spastic Paraparesis; Tuberous Sclerosis; Vascular Dementia (Multi-Infarct Dementia); Vasculitis including Temporal Arteritis; Von Hippel-Lindau Disease (VHL); Wallenberg's syndrome; Werdnig-Hoffman disease; West syndrome; Whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

BRIEF DESCRIPTION OF THE DRAWINGS

FIG. 7 shows the in vitro transfection data (25 ng of siRNA) grouped according to the structural attributes of the inventive lipids.

FIG. 8 shows the in vitro transfection data (25 ng of siRNA) grouped according to the structural attributes of the inventive lipids.

DETAILED DESCRIPTION OF CERTAIN EMBODIMENTS OF THE INVENTION

Figure 1:
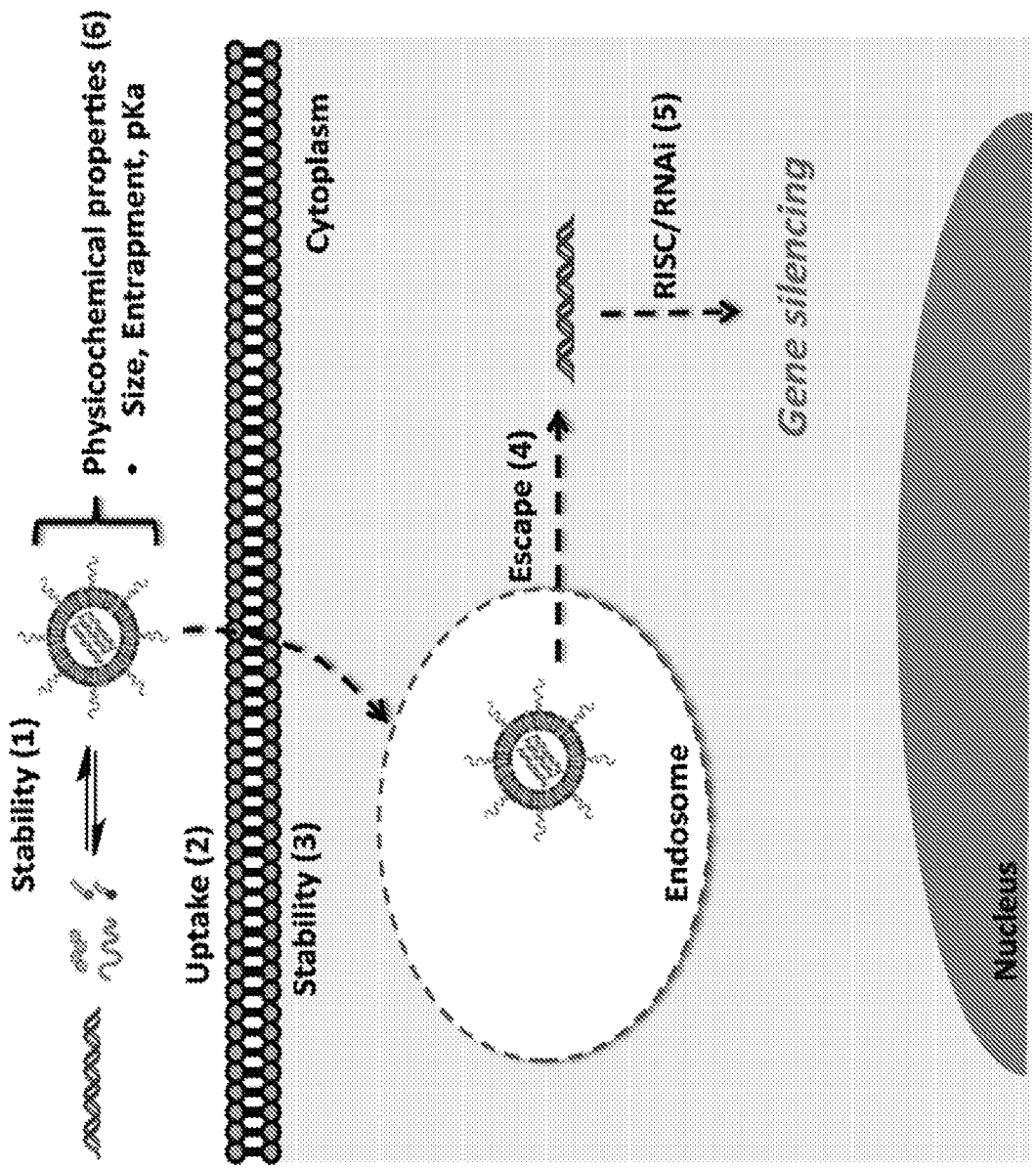
FIG. 1 shows a cellular delivery pathway via the lipid nanoparticles (LNPs) of the invention. Common barriers to delivery and the physicochemical LNP properties evaluated in this present invention are shown.

The present invention provides novel compounds and uses thereof. In one aspect, the invention provides compounds of Formula (I), and salts and stereoisomers thereof. Also provided in the present invention are compositions including a compound of the invention and an agent (e.g., a polynucleotide, such as an siRNA, mRNA, microRNA, shRNA, or plasmid DNA; peptide; protein; small molecule). The compositions have been found to be able to deliver effectively and efficiently the agent to a subject or cell. A compound of the invention, which includes one or more amino moieties that may be protonated to form positively charged ammonium cation(s), may bind to an agent that includes negatively charged moieties to form a complex. A compound of the invention also typically includes more than one unsubstituted or substituted alkyl moiety. The alkyl moitiesare hydrophobic and may assist the inventive compound and/or the complex of the inventive compound and the agent to pass through cell membranes and/or mask the charge on the agent to be delivered. In certain embodiments, an inventive composition including a plurality of molecules of a compound of the invention is in the form of particles.

An agent may be encapsulated within or otherwise associated with the particles. In certain embodiments, the inventive compositions are useful in delivering the agent selectively to a particular tissue or organ (e.g., the liver, spleen, or lung) of the subject. The compositions of the invention (e.g., pharmaceutical compositions) may also be useful in treating and/or preventing a variety of diseases (e.g., genetic diseases, proliferative diseases, hematological diseases, neurological diseases, immunological diseases, gastrointestinal diseases (e.g., liver diseases), respiratory diseases (e.g., lung diseases), painful conditions, psychiatric disorders, metabolic disorders, and spleen diseases) in a subject in need thereof.

Compounds

In one aspect, the present invention provides compounds of Formula (I):

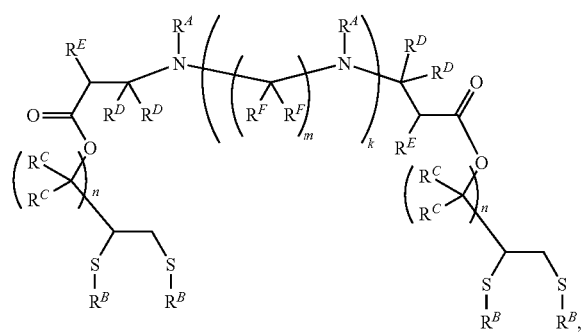

(I)

and salts and stereoisomers thereof;
wherein:

each instance of $R^A$ is independently substituted or unsubstituted acyl, substituted or unsubstituted alkyl, substituted or unsubstituted alkenyl, substituted or unsubstituted heteroaliphatic, substituted or unsubstituted carbocyclyl, substituted or unsubstituted heterocyclyl, substituted or unsubstituted aryl, substituted or unsubstituted heteroaryl, or a nitrogen protecting group;

each instance of $R^B$ is independently substituted or unsubstituted alkyl, substituted or unsubstituted acyl, substituted or unsubstituted carbocyclyl, substituted or unsubstituted heterocyclyl, substituted or unsubstituted aryl, or substituted or unsubstituted heteroaryl;

each instance of $R^C$ is independently hydrogen, halogen, or substituted or unsubstituted $C_{1-6}$ alkyl;

each instance of $R^D$ is independently hydrogen, halogen, or substituted or unsubstituted $C_{1-6}$ alkyl;

each instance of $R^E$ is independently hydrogen, halogen, or substituted or unsubstituted $C_{1-6}$ alkyl;

each instance of $R^F$ is independently hydrogen, halogen, or substituted or unsubstituted $C_{1-6}$ alkyl;

k is 0, 1, 2, 3, or 4;

m is 2, 3, 4, 5, or 6; and each instance of n is independently 1, 2, 3, 4, 5, or 6.

In certain embodiments, the compound of Formula (I) is of Formula (I-A):

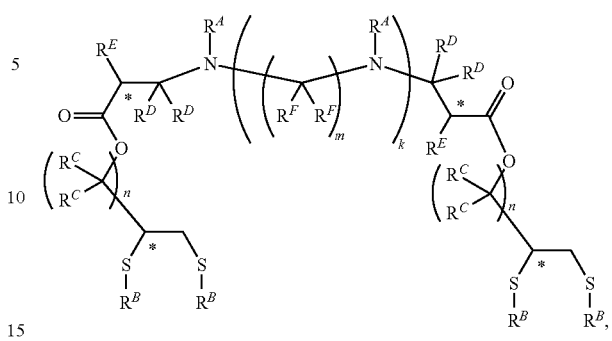

(I-A)

and salts and stereoisomers thereof, wherein the stereochemistry of each one of the carbon atoms labeled with "*" is independently S or R. In certain embodiments, the compounds of Formula (I-A) are a mixture of stereoisomers. In certain embodiments, the compounds of Formula (I-A) are a racemic mixture of stereoisomers.

Compounds of Formula (I) include one or two substituents $R^A$ on the amine moiety/moieties. In certain embodiments, at least one instance of $R^A$ is unsubstituted acyl. In certain embodiments, at least one instance of $R^A$ is unsubstituted acetyl. In certain embodiments, at least one instance of $R^A$ is substituted acyl. In certain embodiments, at least one instance of $R^A$ is unsubstituted alkyl. In certain embodiments, at least one instance of $R^A$ is substituted alkyl. In certain embodiments, at least one instance of $R^A$ is unbranched alkyl. In certain embodiments, at least one instance of $R^A$ is unbranched and unsubstituted alkyl. In certain embodiments, at least one instance of $R^A$ is branched alkyl. In certain embodiments, at least one instance of $R^A$ is unsubstituted $C_{1-12}$ alkyl. In certain embodiments, at least one instance of $R^A$ is substituted $C_{1-12}$ alkyl. In certain embodiments, at least one instance of $R^A$ is unsubstituted $C_{1-6}$ alkyl. In certain embodiments, at least one instance of $R^A$ is unsubstituted methyl. In certain embodiments, at least one instance of $R^A$ is unsubstituted ethyl. In certain embodiments, at least one instance of $R^A$ is unsubstituted propyl. In certain embodiments, at least one instance of $R^A$ is unsubstituted butyl. In certain embodiments, at least one instance of $R^A$ is unsubstituted pentyl. In certain embodiments, at least one instance of $R^A$ is unsubstituted hexyl. In certain embodiments, at least one instance of $R^A$ is substituted $C_{1-6}$ alkyl. In certain embodiments, at least one instance of $R^A$ is $C_{1-6}$ alkyl substituted with one or more substituents $R^{A1}$;

each instance of $R^{A1}$ is independently halogen, substituted or unsubstituted acyl, substituted or unsubstituted alkyl, substituted or unsubstituted alkenyl, substituted or unsubstituted heteroaliphatic, substituted or unsubstituted carbocyclyl, substituted or unsubstituted heterocyclyl, substituted or unsubstituted aryl, substituted or unsubstituted heteroaryl, or $-N(R^{A1a})_2$; and each instance of $R^{A1a}$ is independently hydrogen, substituted or unsubstituted acyl, substituted or unsubstituted alkyl, substituted or unsubstituted alkenyl, substituted or unsubstituted carbocyclyl, substituted or unsubstituted heterocyclyl, substituted or unsubstituted aryl, substituted or unsubstituted heteroaryl, or a nitrogen protecting group, or two instances of $R^{A1a}$ are joined to form a substituted or unsubstituted heterocyclic ring.

In certain embodiments, at least one instance of $R^A$ is $-CH_2F$. In certain embodiments, at least one instance of $R^A$ is $-CHF_2$. In certain embodiments, at least one instance of $R^A$ is $-CF_3$.

In certain embodiments, at least one instance of $R^A$ is $C_{1-6}$ alkyl substituted with one or more substituents $R^{A1}$, wherein each instance of $R^{A1}$ is independently selected from the group consisting of halogen, substituted or unsubstituted alkyl, and substituted or unsubstituted carbocyclyl. In certain embodiments, at least one instance of $R^A$ is $C_{1-6}$ alkyl substituted with one or more substituents $R^{A1}$, wherein at least one instance of $R^{A1}$ is substituted or unsubstituted carbocyclyl. In certain embodiments, at least one instance of $R^A$ is $C_{1-6}$ alkyl substituted with one or more substituents $R^{A1}$, wherein at least one instance of $R^{A1}$ is substituted or unsubstituted, 3- to 9-membered, monocyclic carbocyclyl including zero, one, or two double bonds in the carbocyclic ring. In certain embodiments, at least one instance of $R^A$ is $C_{1-6}$ alkyl substituted with one or more substituents $R^{A1}$, wherein at least one instance of $R^{A1}$ is 3- to 9-membered, monocyclic carbocyclyl including zero, one, or two double bonds in the carbocyclic ring, and wherein the carbocyclyl is unsubstituted or substituted with one or more substituents independently selected from the group consisting of halogen or unsubstituted $C_{1-6}$ alkyl. In certain embodiments, at least one instance of $R^A$ is of the formula:

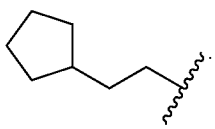 [SMILES: *CCC1CCCC1]

In certain embodiments, at least one instance of $R^A$ is $C_{1-6}$ alkyl substituted with one or more substituents $R^{A1}$, wherein each instance of $R^{A1}$ is independently selected from the group consisting of halogen, substituted or unsubstituted alkyl, and substituted or unsubstituted heterocyclyl. In certain embodiments, at least one instance of $R^A$ is $C_{1-6}$ alkyl substituted with one or more substituents $R^{A1}$, wherein at least one instance of $R^{A1}$ is substituted or unsubstituted heterocyclyl. In certain embodiments, at least one instance of $R^A$ is $C_{1-6}$ alkyl substituted with one or more substituents $R^{A1}$, wherein at least one instance of $R^{A1}$ is substituted or unsubstituted, 3- to 9-membered, monocyclic heterocyclyl including zero, one, or two double bonds in the heterocyclic ring, wherein one, two, or three atoms in the heterocyclic ring is independently selected from the group consisting of nitrogen, oxygen, or sulfur. In certain embodiments, at least one instance of $R^A$ is $C_{1-6}$ alkyl substituted with one or more substituents $R^{A1}$, wherein at least one instance of $R^{A1}$ is 3- to 9-membered, monocyclic heterocyclyl including zero, one, or two double bonds in the heterocyclic ring, wherein one, two, or three atoms in the heterocyclic ring is independently selected from the group consisting of nitrogen, oxygen, or sulfur, and wherein the heterocyclyl is unsubstituted or substituted with one or more substituents independently selected from the group consisting of halogen or unsubstituted $C_{1-6}$ alkyl. In certain embodiments, at least one instance of $R^A$ is of the formula:

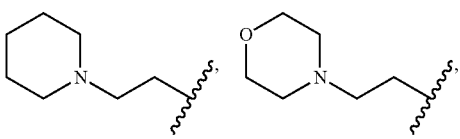

-continued

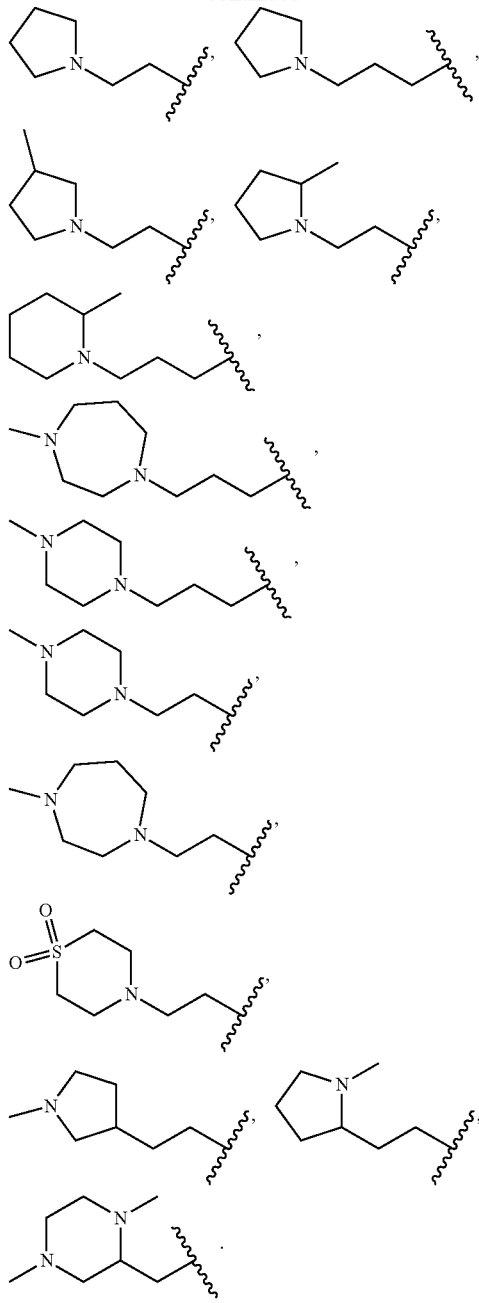

In certain embodiments, at least one instance of $R^A$ is $C_{1-6}$ alkyl substituted with one or more substituents $R^{A1}$, wherein each instance of $R^{A1}$ is independently selected from the group consisting of halogen, substituted or unsubstituted alkyl, and substituted or unsubstituted heteroaryl. In certain embodiments, at least one instance of $R^A$ is $C_{1-6}$ alkyl substituted with one or more substituents $R^{A1}$, wherein at least one instance of $R^{A1}$ is substituted or unsubstituted heteroaryl. In certain embodiments, at least one instance of $R^A$ is $C_{1-6}$ alkyl substituted with one or more substituents $R^{A1}$, wherein at least one instance of $R^{A1}$ is substituted or unsubstituted, 5- to 6-membered, monocyclic heteroaryl, wherein one, two, three, or four atoms in the heteroaryl ring is independently selected from the group consisting of nitrogen, oxygen, or sulfur. In certain embodiments, at least one instance of $R^A$ is $C_{1-6}$ alkyl substituted with one or more substituents $R^{A1}$, wherein at least one instance of $R^{A1}$ is 5- to 6-membered, monocyclic heteroaryl, wherein one, two, three, or four atoms in the heteroaryl ring is independently selected from the group consisting of nitrogen, oxygen, or sulfur, and wherein the heteroaryl is unsubstituted or substituted with one or more substituents independently selected from the group consisting of halogen or unsubstituted $C_{1-6}$ alkyl. In certain embodiments, at least one instance of $R^A$ is $C_{1-6}$ alkyl substituted with one or more substituents $R^{A1}$, wherein at least one instance of $R^{A1}$ is substituted or unsubstituted, 9- to 10-membered, bicyclic heteroaryl, wherein one, two, three, or four atoms in the heteroaryl ring is independently selected from the group consisting of nitrogen, oxygen, or sulfur. In certain embodiments, at least one instance of $R^A$ is $C_{1-6}$ alkyl substituted with one or more substituents $R^{A1}$, wherein at least one instance of $R^{A1}$ is 9- to 10-membered, bicyclic heteroaryl, wherein one, two, three, or four atoms in the heteroaryl ring is independently selected from the group consisting of nitrogen, oxygen, or sulfur, and wherein the heteroaryl is unsubstituted or substituted with one or more substituents independently selected from the group consisting of halogen or unsubstituted $C_{1-6}$ alkyl. In certain embodiments, at least one instance of $R^A$ is of the formula:

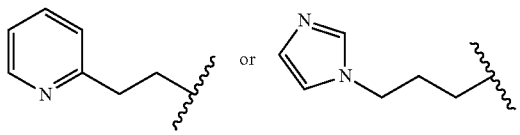

In certain embodiments, at least one instance of $R^A$ is $C_{1-6}$ alkyl substituted with one or more substituents $R^{A1}$, wherein each instance of $R^{A1}$ is independently selected from the group consisting of halogen, substituted or unsubstituted alkyl, and —N($R^{A1a}$)$_2$. In certain embodiments, at least one instance of $R^A$ is $C_{1-6}$ alkyl substituted with one or more substituents $R^{A1}$, wherein at least one instance of $R^{A1}$ is —N($R^{A1a}$)$_2$. In certain embodiments, at least one instance of $R^A$ is $C_{1-6}$ alkyl substituted with one or more substituents, wherein at least one substituent is —N(substituted or unsubstituted alkyl)$_2$. In certain embodiments, at least one instance of $R^A$ is $C_{1-6}$ alkyl substituted with one or more substituents, wherein at least one substituent is —N(unsubstituted alkyl)$_2$. In certain embodiments, at least one instance of $R^A$ is $C_{1-6}$ alkyl substituted with one or more substituents, wherein at least one substituent is —N(unsubstituted $C_{1-6}$ alkyl)$_2$. In certain embodiments, at least one instance of $R^A$ is of the formula:

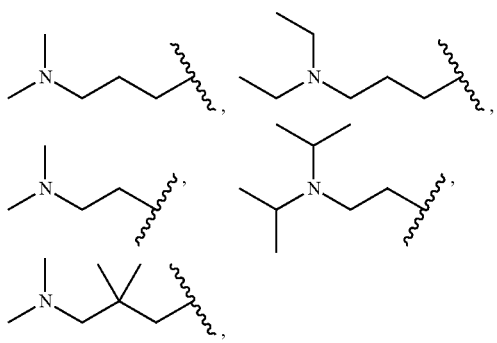

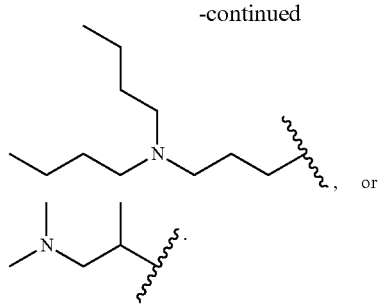

In certain embodiments, at least one instance of $R^A$ is unsubstituted alkenyl. In certain embodiments, at least one instance of $R^A$ is unsubstituted vinyl. In certain embodiments, at least one instance of $R^A$ is substituted alkenyl. In certain embodiments, at least one instance of $R^A$ is unsubstituted heteroaliphatic. In certain embodiments, at least one instance of $R^A$ is saturated heteroaliphatic. In certain embodiments, at least one instance of $R^A$ is unsaturated heteroaliphatic. In certain embodiments, at least one instance of $R^A$ is substituted heteroaliphatic. In certain embodiments, at least one instance of $R^A$ is unbranched heteroaliphatic. In certain embodiments, at least one instance of $R^A$ is branched heteroaliphatic. In certain embodiments, at least one instance of $R^A$ is unsubstituted and unbranched heteroaliphatic. In certain embodiments, at least one instance of $R^A$ is unsubstituted and unbranched heteroaliphatic including 0 to 3 double bonds, 1 to 12 carbon atoms, and 1 to 4 heteroatoms independently selected from the group consisting of nitrogen, oxygen, and sulfur.

In certain embodiments, at least one instance of $R^A$ is substituted carbocyclyl. In certain embodiments, at least one instance of $R^A$ is unsubstituted carbocyclyl. In certain embodiments, at least one instance of $R^A$ is saturated carbocyclyl. In certain embodiments, at least one instance of $R^A$ is unsaturated carbocyclyl. In certain embodiments, at least one instance of $R^A$ is carbocyclyl including one, two, or three double bonds in the carbocyclic ring. In certain embodiments, at least one instance of $R^A$ is monocyclic carbocyclyl. In certain embodiments, at least one instance of $R^A$ is 3- to 9-membered, monocyclic carbocyclyl. In certain embodiments, at least one instance of $R^A$ is cylcopropyl. In certain embodiments, at least one instance of $R^A$ is cyclobutyl. In certain embodiments, at least one instance of $R^A$ is cyclopentyl. In certain embodiments, at least one instance of $R^A$ is cyclohexyl. In certain embodiments, at least one instance of $R^A$ is cycloheptyl. In certain embodiments, at least one instance of $R^A$ is cyclooctyl. In certain embodiments, at least one instance of $R^A$ is cyclononyl. In certain embodiments, at least one instance of $R^A$ is bicyclic carbocyclyl. In certain embodiments, at least one instance of $R^A$ is 5- to 16-membered, bicyclic carbocyclyl.

In certain embodiments, at least one instance of $R^A$ is substituted heterocyclyl. In certain embodiments, at least one instance of $R^A$ is unsubstituted heterocyclyl. In certain embodiments, at least one instance of $R^A$ is saturated heterocyclyl. In certain embodiments, at least one instance of $R^A$ is unsaturated heterocyclyl. In certain embodiments, at least one instance of $R^A$ is heterocyclyl including one, two, or three double bonds in the heterocyclic ring. In certain embodiments, at least one instance of $R^A$ is heterocyclyl, wherein one, two, or three atoms in the heterocyclic ring are independently selected from the group consisting of nitrogen, oxygen, and sulfur. In certain embodiments, at least one instance of $R^A$ is monocyclic heterocyclyl. In certain embodiments, at least one instance of $R^A$ is 3- to 9-membered, monocyclic heterocyclyl. In certain embodiments, at least one instance of $R^A$ is bicyclic heterocyclyl. In certain embodiments, at least one instance of $R^A$ is 5- to 16-membered, bicyclic heterocyclyl. In certain embodiments, at least one instance of $R^A$ is of the formula:

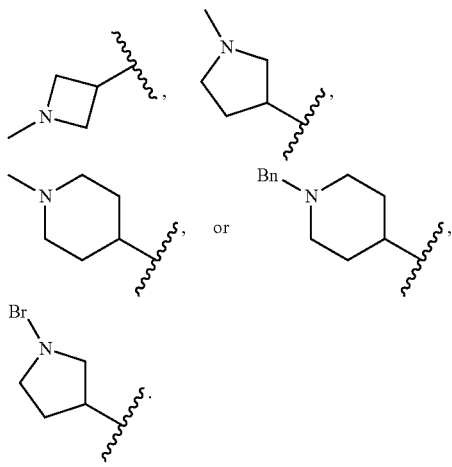

In certain embodiments, at least one instance of $R^A$ is substituted aryl. In certain embodiments, at least one instance of $R^A$ is unsubstituted aryl. In certain embodiments, at least one instance of $R^A$ is 6- to 14-membered aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted naphthyl. In certain embodiments, at least one instance of $R^A$ is unsubstituted naphthyl.

In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms in the heteroaryl ring are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is pyridyl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9-membered, bicyclic heteroaryl. In certain embodiments, at least one instance of $R^A$ is 10-membered, bicyclic heteroaryl.

In certain embodiments, at least one instance of $R^A$ is a nitrogen protecting group. In certain embodiments, at least one instance of $R^A$ is Bn, Boc, Cbz, Fmoc, trifluoroacetyl, triphenylmethyl, acetyl, or Ts.

In certain embodiments, all instances of $R^A$ are different. In certain embodiments, all instances of $R^A$ are the same.

In certain embodiments, at least one instance of $R^{A1}$ is halogen. In certain embodiments, at least one instance of $R^{A1}$ is F. In certain embodiments, at least one instance of $R^{A1}$ is Cl. In certain embodiments, at least one instance of $R^{A1}$ is Br. In certain embodiments, at least one instance of $R^{A1}$ is I (iodine). In certain embodiments, at least one instance of $R^{A1}$ is unsubstituted acyl. In certain embodiments, at least one instance of $R^{A1}$ is unsubstituted acetyl. In certain embodiments, at least one instance of $R^{A1}$ is substituted acyl. In certain embodiments, at least one instance of $R^{A1}$ is unsubstituted alkyl. In certain embodiments, at least one instance of $R^{A1}$ is substituted alkyl. In certain embodiments, at least one instance of $R^{A1}$ is unbranched alkyl. In certain embodiments, at least one instance of $R^{A1}$ is unbranched and unsubstituted alkyl. In certain embodiments, at least one instance of $R^{A1}$ is branched alkyl. In certain embodiments, at least one instance of $R^{A1}$ is unsubstituted $C_{1-12}$ alkyl. In certain embodiments, at least one instance of $R^{A1}$ is substituted $C_{1-12}$ alkyl. In certain embodiments, at least one instance of $R^{A1}$ is unsubstituted $C_{1-6}$ alkyl. In certain embodiments, at least one instance of $R^{A1}$ is unsubstituted methyl. In certain embodiments, at least one instance of $R^{A1}$ is unsubstituted ethyl. In certain embodiments, at least one instance of $R^{A1}$ is unsubstituted propyl. In certain embodiments, at least one instance of $R^{A1}$ is unsubstituted butyl. In certain embodiments, at least one instance of $R^{A1}$ is unsubstituted pentyl. In certain embodiments, at least one instance of $R^{A1}$ is unsubstituted hexyl. In certain embodiments, at least one instance of $R^{A1}$ is substituted $C_{1-6}$ alkyl. In certain embodiments, at least one instance of $R^{A1}$ is —$CH_2F$. In certain embodiments, at least one instance of $R^{A1}$ is —$CHF_2$. In certain embodiments, at least one instance of $R^{A1}$ is —$CF_3$. In certain embodiments, at least one instance of $R^{A1}$ is unsubstituted alkenyl. In certain embodiments, at least one instance of $R^{A1}$ is unsubstituted vinyl. In certain embodiments, at least one instance of $R^{A1}$ is substituted alkenyl. In certain embodiments, at least one instance of $R^{A1}$ is unsubstituted heteroaliphatic. In certain embodiments, at least one instance of $R^{A1}$ is saturated heteroaliphatic. In certain embodiments, at least one instance of $R^{A1}$ is unsaturated heteroaliphatic. In certain embodiments, at least one instance of $R^{A1}$ is substituted heteroaliphatic. In certain embodiments, at least one instance of $R^{A1}$ is unbranched heteroaliphatic. In certain embodiments, at least one instance of $R^{A1}$ is branched heteroaliphatic. In certain embodiments, at least one instance of $R^{A1}$ is unsubstituted and unbranched heteroaliphatic. In certain embodiments, at least one instance of $R^{A1}$ is unsubstituted and unbranched heteroaliphatic including 0 to 3 double bonds, 1 to 12 carbon atoms and 1 to 4 heteroatoms independently selected from the group consisting of nitrogen, oxygen, and sulfur.

In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is saturated carbocyclyl. In certain embodiments, at least one instance of $R^{A1}$ is unsaturated carbocyclyl. In certain embodiments, at least one instance of $R^{A1}$ is carbocyclyl including one, two, or three double bonds in the carbocyclic ring. In certain embodiments, at least one instance of $R^{A1}$ is monocyclic carbocyclyl. In certain embodiments, at least one instance of $R^{A1}$ is 3- to 9-membered, monocyclic carbocyclyl. In certain embodiments, at least one instance of $R^{A1}$ is cylcopropyl. In certain embodiments, at least one instance of $R^{A1}$ is cyclobutyl. In certain embodiments, at least one instance of $R^{A1}$ is cyclopentyl. In certain embodiments, at least one instance of $R^{A1}$ is cyclohexyl. In certain embodiments, at least one instance of $R^{A1}$ is cycloheptyl. In certain embodiments, at least one instance of $R^{A1}$ is cyclooctyl. In certain embodiments, at least one instance of $R^{A1}$ is cyclononyl. In certain embodiments, at least one instance of $R^{A1}$ is bicyclic carbocyclyl. In certain embodiments, at least one instance of $R^{A1}$ is 5- to 16-membered, bicyclic carbocyclyl.

In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is saturated heterocyclyl. In certain embodiments, at least one instance of $R^{A1}$ is unsaturated heterocyclyl. In certain embodiments, at least one instance of $R^{A1}$ is heterocyclyl including one, two, or three double bonds in the heterocyclic ring. In certain embodiments, at least one instance of $R^{A1}$ is heterocyclyl, wherein one, two, or three atoms in the heterocyclic ring are independently selected from the group consisting of nitrogen, oxygen, and sulfur. In certain embodiments, at least one instance of $R^{A1}$ is monocyclic heterocyclyl. In certain embodiments, at least one instance of $R^{A1}$ is 3- to 9-membered, monocyclic heterocyclyl. In certain embodiments, at least one instance of $R^{A1}$ is bicyclic heterocyclyl. In certain embodiments, at least one instance of $R^{A1}$ is 5- to 16-membered, bicyclic heterocyclyl.

In certain embodiments, at least one instance of $R^{A1}$ is substituted aryl. In certain embodiments, at least one instance of $R^{A1}$ is unsubstituted aryl. In certain embodiments, at least one instance of $R^{A1}$ is 6- to 14-membered aryl. In certain embodiments, at least one instance of $R^{A1}$ is 6- to 10-membered aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is substituted naphthyl. In certain embodiments, at least one instance of $R^{A1}$ is unsubstituted naphthyl.

In certain embodiments, at least one instance of $R^{A1}$ is substituted heteroaryl. In certain embodiments, at least one instance of $R^{A1}$ is unsubstituted heteroaryl. In certain embodiments, at least one instance of $R^{A1}$ is heteroaryl, wherein one, two, three, or four atoms in the heteroaryl ring are independently selected from the group consisting of nitrogen, oxygen, and sulfur. In certain embodiments, at least one instance of $R^{A1}$ is monocyclic heteroaryl. In certain embodiments, at least one instance of $R^{A1}$ is 5-membered, monocyclic heteroaryl. In certain embodiments, at least one instance of $R^{A1}$ is 6-membered, monocyclic heteroaryl. In certain embodiments, at least one instance of $R^{A1}$ is pyridyl. In certain embodiments, at least one instance of $R^{A1}$ is bicyclic heteroaryl, wherein the point of attachment may be on any atom of the bicyclic heteroaryl ring system, as valency permits. In certain embodiments, at least one instance of $R^{A1}$ is 9-membered, bicyclic heteroaryl. In certain embodiments, at least one instance of $R^{A1}$ is 10-membered, bicyclic heteroaryl.

In certain embodiments, at least one instance of $R^{A1}$ is —N($R^{A1a}$)$_2$. In certain embodiments, at least one instance of $R^{A1}$ is —N(substituted or unsubstituted alkyl)$_2$. In certain embodiments, at least one instance of $R^{A1}$ is —N(unsubstituted alkyl)$_2$. In certain embodiments, at least one instance of $R^{A1}$ is —N(unsubstituted $C_{1-6}$ alkyl)$_2$.

In certain embodiments, at least one instance of $R^{A1a}$ is hydrogen. In certain embodiments, at least one instance of $R^{A1a}$ is unsubstituted acyl. In certain embodiments, at least one instance of $R^{A1a}$ is unsubstituted acetyl. In certain embodiments, at least one instance of $R^{A1a}$ is substituted acyl. In certain embodiments, at least one instance of $R^{A1a}$ is unsubstituted alkyl. In certain embodiments, at least one instance of $R^{A1a}$ is substituted alkyl. In certain embodiments, at least one instance of $R^{A1a}$ is unbranched alkyl. In certain embodiments, at least one instance of $R^{A1a}$ is unbranched and unsubstituted alkyl. In certain embodiments, at least one instance of $R^{A1a}$ is branched alkyl. In certain embodiments, at least one instance of $R^{A1a}$ is unsubstituted $C_{1-12}$ alkyl. In certain embodiments, at least one instance of $R^{A1a}$ is substituted $C_{1-12}$ alkyl. In certain embodiments, at least one instance of $R^{A1a}$ is unsubstituted $C_{1-6}$ alkyl. In certain embodiments, at least one instance of $R^{A1a}$ is unsubstituted methyl. In certain embodiments, at least one instance of $R^{A1a}$ is unsubstituted ethyl. In certain embodiments, at least one instance of $R^{A1a}$ is unsubstituted propyl. In certain embodiments, at least one instance of $R^{A1a}$ is unsubstituted butyl. In certain embodiments, at least one instance of $R^{A1a}$ is unsubstituted pentyl. In certain embodiments, at least one instance of $R^{A1a}$ is unsubstituted hexyl. In certain embodiments, at least one instance of $R^{A1a}$ is substituted $C_{1-6}$ alkyl. In certain embodiments, at least one instance of $R^{A1a}$ is —CH$_2$F. In certain embodiments, at least one instance of $R^{A1a}$ is —CHF$_2$. In certain embodiments, at least one instance of $R^{A1a}$ is —CF$_3$. In certain embodiments, at least one instance of $R^{A1a}$ is unsubstituted alkenyl. In certain embodiments, at least one instance of $R^{A1a}$ is unsubstituted vinyl. In certain embodiments, at least one instance of $R^{A1a}$ is substituted alkenyl.

In certain embodiments, at least one instance of $R^{A1a}$ is substituted carbocyclyl. In certain embodiments, at least one instance of $R^{A1a}$ is unsubstituted carbocyclyl. In certain embodiments, at least one instance of $R^{A1a}$ is saturated carbocyclyl. In certain embodiments, at least one instance of $R^{A1a}$ is unsaturated carbocyclyl. In certain embodiments, at least one instance of $R^{A1a}$ is carbocyclyl including one, two, or three double bonds in the carbocyclic ring. In certain embodiments, at least one instance of $R^{A1a}$ is monocyclic carbocyclyl. In certain embodiments, at least one instance of $R^{A1a}$ is 3- to 9-membered, monocyclic carbocyclyl. In certain embodiments, at least one instance of $R^{A1a}$ is cylcopropyl. In certain embodiments, at least one instance of $R^{A1a}$ is cyclobutyl. In certain embodiments, at least one instance of $R^{A1a}$ is cyclopentyl. In certain embodiments, at least one instance of $R^{A1a}$ is cyclohexyl. In certain embodiments, at least one instance of $R^{A1a}$ is cycloheptyl. In certain embodiments, at least one instance of $R^{A1a}$ is cyclooctyl. In certain embodiments, at least one instance of $R^{A1a}$ is cyclononyl. In certain embodiments, at least one instance of $R^{A1a}$ is bicyclic carbocyclyl. In certain embodiments, at least one instance of $R^{A1a}$ is 5- to 16-membered, bicyclic carbocyclyl.

In certain embodiments, at least one instance of $R^{A1a}$ is substituted heterocyclyl. In certain embodiments, at least one instance of $R^{A1a}$ is unsubstituted heterocyclyl. In certain embodiments, at least one instance of $R^{A1a}$ is saturated heterocyclyl. In certain embodiments, at least one instance of $R^{A1a}$ is unsaturated heterocyclyl. In certain embodiments, at least one instance of $R^{A1a}$ is heterocyclyl including one, two, or three double bonds in the heterocyclic ring. In certain embodiments, at least one instance of $R^{A1a}$ is heterocyclyl, wherein one, two, or three atoms in the heterocyclic ring are independently selected from the group consisting of nitrogen, oxygen, and sulfur. In certain embodiments, at least one instance of $R^{A1a}$ is monocyclic heterocyclyl. In certain embodiments, at least one instance of $R^{A1a}$ is 3- to 9-membered, monocyclic heterocyclyl. In certain embodiments, at least one instance of $R^{A1a}$ is bicyclic heterocyclyl. In certain embodiments, at least one instance of $R^{A1a}$ is 5- to 16-membered, bicyclic heterocyclyl.

In certain embodiments, at least one instance of $R^{A1a}$ is substituted aryl. In certain embodiments, at least one instance of $R^{A1a}$ is unsubstituted aryl. In certain embodiments, at least one instance of $R^{A1a}$ is 6- to 14-membered aryl. In certain embodiments, at least one instance of $R^{A1a}$ is 6- to 10-membered aryl. In certain embodiments, at least one instance of $R^{A1a}$ is substituted phenyl. In certain embodiments, at least one instance of $R^{A1a}$ is unsubstituted phenyl. In certain embodiments, at least one instance of $R^{A1a}$ is substituted naphthyl. In certain embodiments, at least one instance of $R^{A1a}$ is unsubstituted naphthyl.

In certain embodiments, at least one instance of $R^{A1a}$ is substituted heteroaryl. In certain embodiments, at least one instance of $R^{A1a}$ is unsubstituted heteroaryl. In certain embodiments, at least one instance of $R^{A1a}$ is heteroaryl, wherein one, two, three, or four atoms in the heteroaryl ring are independently selected from the group consisting of nitrogen, oxygen, and sulfur. In certain embodiments, at least one instance of $R^{A1a}$ is monocyclic heteroaryl. In certain embodiments, at least one instance of $R^{A1a}$ is 5-membered, monocyclic heteroaryl. In certain embodiments, at least one instance of $R^{A1a}$ is 6-membered, monocyclic heteroaryl. In certain embodiments, at least one instance of $R^{A1a}$ is pyridyl. In certain embodiments, at least one instance of $R^{A1a}$ is bicyclic heteroaryl, wherein the point of attachment may be on any atom of the bicyclic heteroaryl ring system, as valency permits. In certain embodiments, at least one instance of $R^{A1a}$ is 9-membered, bicyclic heteroaryl. In certain embodiments, at least one instance of $R^{A1a}$ is 10-membered, bicyclic heteroaryl.

In certain embodiments, at least one instance of $R^{A1a}$ is a nitrogen protecting group. In certain embodiments, at least one instance of $R^{A1a}$ is Bn, Boc, Cbz, Fmoc, trifluoroacetyl, triphenylmethyl, acetyl, or Ts.

In certain embodiments, two instances of $R^{A1a}$ are joined to form substituted or unsubstituted heterocyclyl. In certain embodiments, two instances of $R^{A1a}$ are joined to form saturated or unsaturated heterocyclyl. In certain embodiments, two instances of $R^{A1a}$ are joined to form heterocyclyl including one, two, or three double bonds in the heterocyclic ring. In certain embodiments, two instances of $R^{A1a}$ are joined to form heterocyclyl, wherein one, two instances of, or three atoms in the heterocyclic ring are independently selected from the group consisting of nitrogen, oxygen, and sulfur. In certain embodiments, two instances of $R^{A1a}$ are joined to form 3- to 9-membered, monocyclic heterocyclyl. In certain embodiments, two instances of $R^{A1a}$ are joined to form 5- to 16-membered, bicyclic heterocyclyl.

Compounds of Formula (I) include $R^B$ groups on the sulfur atoms. In certain embodiments, at least one instance of $R^B$ is unsubstituted alkyl. In certain embodiments, at least one instance of $R^B$ is substituted alkyl. In certain embodiments, at least one instance of $R^B$ is unbranched alkyl. In certain embodiments, at least one instance of $R^B$ is unbranched and unsubstituted alkyl. In certain embodiments, at least one instance of $R^B$ is branched alkyl. In certain embodiments, at least one instance of $R^B$ is unsubstituted $C_{1-24}$ alkyl. In certain embodiments, at least one instance of $R^B$ is substituted $C_{1-24}$ alkyl. In certain embodiments, at least one instance of $R^B$ is fluorinated $C_{1-24}$ alkyl. In certain embodiments, at least one instance of $R^B$ is unsubstituted $C_{6-24}$ alkyl. In certain embodiments, at least one instance of $R^B$ is substituted $C_{6-24}$ alkyl. In certain embodiments, at least one instance of $R^B$ is unsubstituted $C_{12-24}$ alkyl. In certain embodiments, at least one instance of $R^B$ is substituted $C_{12-24}$ alkyl. In certain embodiments, at least one instance of $R^B$ is unsubstituted $C_{18-24}$ alkyl. In certain embodiments, at least one instance of $R^B$ is substituted $C_{18-24}$ alkyl. In certain embodiments, at least one instance of $R^B$ is unsubstituted $C_{1-24}$ alkyl. In certain embodiments, at least one instance of $R^B$ is substituted $C_{1-18}$ alkyl. In certain embodiments, at least one instance of $R^B$ is unsubstituted $C_{6-18}$ alkyl. In certain embodiments, at least one instance of $R^B$ is substituted $C_{6-18}$ alkyl. In certain embodiments, at least one instance of $R^B$ is unsubstituted $C_{12-18}$ alkyl. In certain embodiments, at least one instance of $R^B$ is substituted $C_{12-18}$ alkyl. In certain embodiments, at least one instance of $R^B$ is unsubstituted $C_{1-12}$ alkyl. In certain embodiments, at least one instance of $R^B$ is substituted $C_{1-12}$ alkyl. In certain embodiments, at least one instance of $R^B$ is unsubstituted $C_{6-12}$ alkyl. In certain embodiments, at least one instance of $R^B$ is substituted $C_{6-12}$ alkyl. In certain embodiments, at least one instance of $R^B$ is unsubstituted $C_{1-6}$ alkyl. In certain embodiments, at least one instance of $R^B$ is substituted $C_{1-6}$ alkyl. In certain embodiments, at least one instance of $R^B$ is unsubstituted $C_4$ alkyl. In certain embodiments, at least one instance of $R^B$ is substituted $C_4$ alkyl. In certain embodiments, at least one instance of $R^B$ is unsubstituted $C_{1-4}$ alkyl. In certain embodiments, at least one instance of $R^B$ is substituted $C_{1-4}$ alkyl. In certain embodiments, at least one instance of $R^B$ is unsubstituted methyl. In certain embodiments, at least one instance of $R^B$ is substituted methyl. In certain embodiments, at least one instance of $R^B$ is —$CH_2F$. In certain embodiments, at least one instance of $R^B$ is —$CHF_2$. In certain embodiments, at least one instance of $R^B$ is —$CF_3$. In certain embodiments, at least one instance of $R^B$ is unsubstituted ethyl. In certain embodiments, at least one instance of $R^B$ is substituted ethyl. In certain embodiments, at least one instance of $R^B$ is fluorinated ethyl. In certain embodiments, at least one instance of $R^B$ is perfluorinated ethyl. In certain embodiments, at least one instance of $R^B$ is unsubstituted propyl. In certain embodiments, at least one instance of $R^B$ is substituted propyl. In certain embodiments, at least one instance of $R^B$ is fluorinated propyl. In certain embodiments, at least one instance of $R^B$ is perfluorinated propyl. In certain embodiments, at least one instance of $R^B$ is unsubstituted butyl. In certain embodiments, at least one instance of $R^B$ is substituted butyl. In certain embodiments, at least one instance of $R^B$ is fluorinated butyl. In certain embodiments, at least one instance of $R^B$ is perfluorinated butyl. In certain embodiments, at least one instance of $R^B$ is unsubstituted pentyl. In certain embodiments, at least one instance of $R^B$ is substituted pentyl. In certain embodiments, at least one instance of $R^B$ is fluorinated pentyl. In certain embodiments, at least one instance of $R^B$ is perfluorinated pentyl. In certain embodiments, at least one instance of $R^B$ is unsubstituted hexyl. In certain embodiments, at least one instance of $R^B$ is substituted hexyl. In certain embodiments, at least one instance of $R^B$ is fluorinated hexyl. In certain embodiments, at least one instance of $R^B$ is perfluorinated hexyl. In certain embodiments, at least one instance of $R^B$ is unsubstituted heptyl. In certain embodiments, at least one instance of $R^B$ is substituted heptyl. In certain embodiments, at least one instance of $R^B$ is fluorinated heptyl. In certain embodiments, at least one instance of $R^B$ is perfluorinated heptyl. In certain embodiments, at least one instance of $R^B$ is unsubstituted octyl. In certain embodiments, at least one instance of $R^B$ is substituted octyl. In certain embodiments, at least one instance of $R^B$ is fluorinated octyl. In certain embodiments, at least one instance of $R^B$ is perfluorinated octyl. In certain embodiments, at least one instance of $R^B$ is unsubstituted nonyl. In certain embodiments, at least one instance of $R^B$ is substituted nonyl. In certain embodiments, at least one instance of $R^B$ is fluorinated nonyl. In certain embodiments, at least one instance of $R^B$ is perfluorinated nonyl. In certain embodiments, at least one instance of $R^B$ is unsubstituted decyl. In certain embodiments, at least one instance of $R^B$ is substituted decyl. In certain embodiments, at least one instance of $R^B$ is fluorinated decyl. In certain embodiments, at least one instance of $R^B$ is perfluorinated decyl. In certain embodiments, at least one instance of $R^B$ is unsubstituted undecyl. In certain embodiments, at least one instance of $R^B$ is substituted undecyl. In certain embodiments, at least one instance of $R^B$ is fluorinated undecyl. In certain embodiments, at least one instance of $R^B$ is perfluorinated undecyl. In certain embodiments, at least one instance of $R^B$ is unsubstituted dodecyl. In certain embodiments, at least one instance of $R^B$ is substituted dodecyl. In certain embodiments, at least one instance of $R^B$ is fluorinated dodecyl. In certain embodiments, at least one instance of $R^B$ is perfluorinated dodecyl. In certain embodiments, at least one instance of $R^B$ is unsubstituted tridecyl. In certain embodiments, at least one instance of $R^B$ is substituted tridecyl. In certain embodiments, at least one instance of $R^B$ is fluorinated tridecyl. In certain embodiments, at least one instance of $R^B$ is perfluorinated tridecyl. In certain embodiments, at least one instance of $R^B$ is unsubstituted tetradecyl. In certain embodiments, at least one instance of $R^B$ is substituted tetradecyl. In certain embodiments, at least one instance of $R^B$ is fluorinated tetradecyl. In certain embodiments, at least one instance of $R^B$ is perfluorinated tetradecyl. In certain embodiments, at least one instance of $R^B$ is unsubstituted pentadecyl. In certain embodiments, at least one instance of $R^B$ is substituted pentadecyl. In certain embodiments, at least one instance of $R^B$ is fluorinated pentadecyl. In certain embodiments, at least one instance of $R^B$ is perfluorinated pentadecyl. In certain embodiments, at least one instance of $R^B$ is unsubstituted hexadecyl. In certain embodiments, at least one instance of $R^B$ is substituted hexadecyl. In certain embodiments, at least one instance of $R^B$ is fluorinated hexadecyl. In certain embodiments, at least one instance of $R^B$ is perfluorinated hexadecyl. In certain embodiments, at least one instance of $R^B$ is unsubstituted heptadecyl. In certain embodiments, at least one instance of $R^B$ is substituted heptadecyl. In certain embodiments, at least one instance of $R^B$ is fluorinated heptadecyl. In certain embodiments, at least one instance of $R^B$ is perfluorinated heptadecyl. In certain embodiments, at least one instance of $R^B$ is unsubstituted octadecyl. In certain embodiments, at least one instance of $R^B$ is substituted octadecyl. In certain embodiments, at least one instance of $R^B$ is fluorinated octadecyl. In certain embodiments, at least one instance of $R^B$ is perfluorinated octadecyl.

In certain embodiments, at least two instances of $R^B$ are unsubstituted alkyl. In certain embodiments, at least two instances of $R^B$ are substituted alkyl. In certain embodiments, at least two instances of $R^B$ are unbranched alkyl. In certain embodiments, at least two instances of $R^B$ are unbranched and unsubstituted alkyl. In certain embodiments, at least two instances of $R^B$ are branched alkyl. In certain embodiments, at least two instances of $R^B$ are unsubstituted $C_{1-24}$ alkyl. In certain embodiments, at least two instances of $R^B$ are substituted $C_{1-24}$ alkyl. In certain embodiments, at least two instances of $R^B$ are fluorinated $C_{1-24}$ alkyl. In certain embodiments, at least two instances of $R^B$ are unsubstituted $C_{6-24}$ alkyl. In certain embodiments, at least two instances of $R^B$ are substituted $C_{6-24}$ alkyl. In certain embodiments, at least two instances of $R^B$ are unsubstituted $C_{12-24}$ alkyl. In certain embodiments, at least two instances of $R^B$ are substituted $C_{12-24}$ alkyl. In certain embodiments, at least two instances of $R^B$ are unsubstituted $C_{18-24}$ alkyl. In certain embodiments, at least two instances of $R^B$ are substituted $C_{18-24}$ alkyl. In certain embodiments, at least two instances of $R^B$ are unsubstituted $C_{1-18}$ alkyl. In certain embodiments, at least two instances of $R^B$ are substituted $C_{6-18}$ alkyl. In certain embodiments, at least two instances of $R^B$ are unsubstituted $C_{6-18}$ alkyl. In certain embodiments, at least two instances of $R^B$ are substituted $C_{6-18}$ alkyl. In certain embodiments, at least two instances of $R^B$ are unsubstituted $C_{12-18}$ alkyl. In certain embodiments, at least two instances of $R^B$ are substituted $C_{12-18}$ alkyl. In certain embodiments, at least two instances of $R^B$ are unsubstituted $C_{1-12}$ alkyl. In certain embodiments, at least two instances of $R^B$ are substituted $C_{1-12}$ alkyl. In certain embodiments, at least two instances of $R^B$ are unsubstituted $C_{6-12}$ alkyl. In certain embodiments, at least two instances of $R^B$ are substituted $C_{6-2}$ alkyl. In certain embodiments, at least two instances of $R^B$ are unsubstituted $C_{1-6}$ alkyl. In certain embodiments, at least two instances of $R^B$ are substituted $C_{1-6}$ alkyl. In certain embodiments, at least two instances of $R^B$ are unsubstituted $C_{4-6}$ alkyl. In certain embodiments, at least two instances of $R^B$ are substituted $C_{4-6}$ alkyl. In certain embodiments, at least two instances of $R^B$ are unsubstituted $C_{1-4}$ alkyl. In certain embodiments, at least two instances of $R^B$ are substituted $C_{1-4}$ alkyl. In certain embodiments, at least two instances of $R^B$ are unsubstituted methyl. In certain embodiments, at least two instances of $R^B$ are substituted methyl. In certain embodiments, at least two instances of $R^B$ are —$CH_2F$. In certain embodiments, at least two instances of $R^B$ are —$CHF_2$. In certain embodiments, at least two instances of $R^B$ are —$CF_3$. In certain embodiments, at least two instances of $R^B$ are unsubstituted ethyl. In certain embodiments, at least two instances of $R^B$ are substituted ethyl. In certain embodiments, at least two instances of $R^B$ are fluorinated ethyl. In certain embodiments, at least two instances of $R^B$ are perfluorinated ethyl. In certain embodiments, at least two instances of $R^B$ are unsubstituted propyl. In certain embodiments, at least two instances of $R^B$ are substituted propyl. In certain embodiments, at least two instances of $R^B$ are fluorinated propyl. In certain embodiments, at least two instances of $R^B$ are perfluorinated propyl. In certain embodiments, at least two instances of $R^B$ are unsubstituted butyl. In certain embodiments, at least two instances of $R^B$ are substituted butyl. In certain embodiments, at least two instances of $R^B$ are fluorinated butyl. In certain embodiments, at least two instances of $R^B$ are perfluorinated butyl. In certain embodiments, at least two instances of $R^B$ are unsubstituted pentyl. In certain embodiments, at least two instances of $R^B$ are substituted pentyl. In certain embodiments, at least two instances of $R^B$ are fluorinated pentyl. In certain embodiments, at least two instances of $R^B$ are perfluorinated pentyl. In certain embodiments, at least two instances of $R^B$ are unsubstituted hexyl. In certain embodiments, at least two instances of $R^B$ are substituted hexyl. In certain embodiments, at least two instances of $R^B$ are fluorinated hexyl. In certain embodiments, at least two instances of $R^B$ are perfluorinated hexyl. In certain embodiments, at least two instances of $R^B$ are unsubstituted heptyl. In certain embodiments, at least two instances of $R^B$ are substituted heptyl. In certain embodiments, at least two instances of $R^B$ are fluorinated heptyl. In certain embodiments, at least two instances of $R^B$ are perfluorinated heptyl. In certain embodiments, at least two instances of $R^B$ are unsubstituted octyl. In certain embodiments, at least two instances of $R^B$ are substituted octyl. In certain embodiments, at least two instances of $R^B$ are fluorinated octyl. In certain embodiments, at least two instances of $R^B$ are perfluorinated octyl. In certain embodiments, at least two instances of $R^B$ are unsubstituted nonyl. In certain embodiments, at least two instances of $R^B$ are substituted nonyl. In certain embodiments, at least two instances of $R^B$ are fluorinated nonyl. In certain embodiments, at least two instances of $R^B$ are perfluorinated nonyl. In certain embodiments, at least two instances of $R^B$ are unsubstituted decyl. In certain embodiments, at least two instances of $R^B$ are substituted decyl. In certain embodiments, at least two instances of $R^B$ are fluorinated decyl. In certain embodiments, at least two instances of $R^B$ are perfluorinated decyl. In certain embodiments, at least two instances of $R^B$ are unsubstituted undecyl. In certain embodiments, at least two instances of $R^B$ are substituted undecyl. In certain embodiments, at least two instances of $R^B$ are fluorinated undecyl. In certain embodiments, at least two instances of $R^B$ are perfluorinated undecyl. In certain embodiments, at least two instances of $R^B$ are unsubstituted dodecyl. In certain embodiments, at least two instances of $R^B$ are substituted dodecyl. In certain embodiments, at least two instances of $R^B$ are fluorinated dodecyl. In certain embodiments, at least two instances of $R^B$ are perfluorinated dodecyl. In certain embodiments, at least two instances of $R^B$ are unsubstituted tridecyl. In certain embodiments, at least two instances of $R^B$ are substituted tridecyl. In certain embodiments, at least two instances of $R^B$ are fluorinated tridecyl. In certain embodiments, at least two instances of $R^B$ are perfluorinated tridecyl. In certain embodiments, at least two instances of $R^B$ are unsubstituted tetradecyl. In certain embodiments, at least two instances of $R^B$ are substituted tetradecyl. In certain embodiments, at least two instances of $R^B$ are fluorinated tetradecyl. In certain embodiments, at least two instances of $R^B$ are perfluorinated tetradecyl. In certain embodiments, at least two instances of $R^B$ are unsubstituted pentadecyl. In certain embodiments, at least two instances of $R^B$ are substituted pentadecyl. In certain embodiments, at least two instances of $R^B$ are fluorinated pentadecyl. In certain embodiments, at least two instances of $R^B$ are perfluorinated pentadecyl. In certain embodiments, at least two instances of $R^B$ are unsubstituted hexadecyl. In certain embodiments, at least two instances of $R^B$ are substituted hexadecyl. In certain embodiments, at least two instances of $R^B$ are fluorinated hexadecyl. In certain embodiments, at least two instances of $R^B$ are perfluorinated hexadecyl. In certain embodiments, at least two instances of $R^B$ are unsubstituted heptadecyl. In certain embodiments, at least two instances of $R^B$ are substituted heptadecyl. In certain embodiments, at least two instances of $R^B$ are fluorinated heptadecyl. In certain embodiments, at least two instances of $R^B$ are perfluorinated heptadecyl. In certain embodiments, at least two instances of $R^B$ are unsubstituted octadecyl. In certain embodiments, at least two instances of $R^B$ are substituted octadecyl. In certain embodiments, at least two instances of $R^B$ are fluorinated octadecyl. In certain embodiments, at least two instances of $R^B$ are perfluorinated octadecyl.

In certain embodiments, at least three instances of $R^B$ are unsubstituted alkyl. In certain embodiments, at least three instances of $R^B$ are substituted alkyl. In certain embodiments, at least three instances of $R^B$ are unbranched alkyl. In certain embodiments, at least three instances of $R^B$ are unbranched and unsubstituted alkyl. In certain embodiments, at least three instances of $R^B$ are branched alkyl. In certain embodiments, at least three instances of $R^B$ are unsubstituted $C_{1-24}$ alkyl. In certain embodiments, at least three instances of $R^B$ are substituted $C_{1-24}$ alkyl. In certain embodiments, at least three instances of $R^B$ are fluorinated $C_{1-24}$ alkyl. In certain embodiments, at least three instances of $R^B$ are unsubstituted $C_{6-24}$ alkyl. In certain embodiments, at least three instances of $R^B$ are substituted $C_{6-24}$ alkyl. In certain embodiments, at least three instances of $R^B$ are unsubstituted $C_{12-24}$ alkyl. In certain embodiments, at least three instances of $R^B$ are substituted $C_{12-24}$ alkyl. In certain embodiments, at least three instances of $R^B$ are unsubstituted $C_{18-24}$ alkyl. In certain embodiments, at least three instances of $R^B$ are substituted $C_{18-24}$ alkyl. In certain embodiments, at least three instances of $R^B$ are unsubstituted $C_{1-18}$ alkyl. In certain embodiments, at least three instances of $R^B$ are substituted $C_{1-18}$ alkyl. In certain embodiments, at least three instances of $R^B$ are unsubstituted $C_{6-18}$ alkyl. In certain embodiments, at least three instances of $R^B$ are substituted $C_{6-18}$ alkyl. In certain embodiments, at least three instances of $R^B$ are unsubstituted $C_{12-18}$ alkyl. In certain embodiments, at least three instances of $R^B$ are substituted $C_{12-18}$ alkyl. In certain embodiments, at least three instances of $R^B$ are unsubstituted $C_{1-12}$ alkyl. In certain embodiments, at least three instances of $R^B$ are substituted $C_{1-12}$ alkyl. In certain embodiments, at least three instances of $R^B$ are unsubstituted $C_{6-12}$ alkyl. In certain embodiments, at least three instances of $R^B$ are substituted $C_{6-12}$ alkyl. In certain embodiments, at least three instances of $R^B$ are unsubstituted $C_{1-6}$ alkyl. In certain embodiments, at least three instances of $R^B$ are substituted $C_{1-6}$ alkyl. In certain embodiments, at least three instances of $R^B$ are unsubstituted $C_{4-6}$ alkyl. In certain embodiments, at least three instances of $R^B$ are substituted $C_{4-6}$ alkyl. In certain embodiments, at least three instances of $R^B$ are unsubstituted $C_{1-4}$ alkyl. In certain embodiments, at least three instances of $R^B$ are substituted $C_{1-4}$ alkyl. In certain embodiments, at least three instances of $R^B$ are unsubstituted methyl. In certain embodiments, at least three instances of $R^B$ are substituted methyl. In certain embodiments, at least three instances of $R^B$ are —$CH_2F$. In certain embodiments, at least three instances of $R^B$ are —$CHF_2$. In certain embodiments, at least three instances of $R^B$ are —$CF_3$. In certain embodiments, at least three instances of $R^B$ are unsubstituted ethyl. In certain embodiments, at least three instances of $R^B$ are substituted ethyl. In certain embodiments, at least three instances of $R^B$ are fluorinated ethyl. In certain embodiments, at least three instances of $R^B$ are perfluorinated ethyl. In certain embodiments, at least three instances of $R^B$ are unsubstituted propyl. In certain embodiments, at least three instances of $R^B$ are substituted propyl. In certain embodiments, at least three instances of $R^B$ are fluorinated propyl. In certain embodiments, at least three instances of $R^B$ are perfluorinated propyl. In certain embodiments, at least three instances of $R^B$ are unsubstituted butyl. In certain embodiments, at least three instances of $R^B$ are substituted butyl. In certain embodiments, at least three instances of $R^B$ are fluorinated butyl. In certain embodiments, at least three instances of $R^B$ are perfluorinated butyl. In certain embodiments, at least three instances of $R^B$ are unsubstituted pentyl. In certain embodiments, at least three instances of $R^B$ are substituted pentyl. In certain embodiments, at least three instances of $R^B$ are fluorinated pentyl. In certain embodiments, at least three instances of $R^B$ are perfluorinated pentyl. In certain embodiments, at least three instances of $R^B$ are unsubstituted hexyl. In certain embodiments, at least three instances of $R^B$ are substituted hexyl. In certain embodiments, at least three instances of $R^B$ are fluorinated hexyl. In certain embodiments, at least three instances of $R^B$ are perfluorinated hexyl. In certain embodiments, at least three instances of $R^B$ are unsubstituted heptyl. In certain embodiments, at least three instances of $R^B$ are substituted heptyl. In certain embodiments, at least three instances of $R^B$ are fluorinated heptyl. In certain embodiments, at least three instances of $R^B$ are perfluorinated heptyl. In certain embodiments, at least three instances of $R^B$ are unsubstituted octyl. In certain embodiments, at least three instances of $R^B$ are substituted octyl. In certain embodiments, at least three instances of $R^B$ are fluorinated octyl. In certain embodiments, at least three instances of $R^B$ are perfluorinated octyl. In certain embodiments, at least three instances of $R^B$ are unsubstituted nonyl. In certain embodiments, at least three instances of $R^B$ are substituted nonyl. In certain embodiments, at least three instances of $R^B$ are fluorinated nonyl. In certain embodiments, at least three instances of $R^B$ are perfluorinated nonyl. In certain embodiments, at least three instances of $R^B$ are unsubstituted decyl. In certain embodiments, at least three instances of $R^B$ are substituted decyl. In certain embodiments, at least three instances of $R^B$ are fluorinated decyl. In certain embodiments, at least three instances of $R^B$ are perfluorinated decyl. In certain embodiments, at least three instances of $R^B$ are unsubstituted undecyl. In certain embodiments, at least three instances of $R^B$ are substituted undecyl. In certain embodiments, at least three instances of $R^B$ are fluorinated undecyl. In certain embodiments, at least three instances of $R^B$ are perfluorinated undecyl. In certain embodiments, at least three instances of $R^B$ are unsubstituted dodecyl. In certain embodiments, at least three instances of $R^B$ are substituted dodecyl. In certain embodiments, at least three instances of $R^B$ are fluorinated dodecyl. In certain embodiments, at least three instances of $R^B$ are perfluorinated dodecyl. In certain embodiments, at least three instances of $R^B$ are unsubstituted tridecyl. In certain embodiments, at least three instances of $R^B$ are substituted tridecyl. In certain embodiments, at least three instances of $R^B$ are fluorinated tridecyl. In certain embodiments, at least three instances of $R^B$ are perfluorinated tridecyl. In certain embodiments, at least three instances of $R^B$ are unsubstituted tetradecyl. In certain embodiments, at least three instances of $R^B$ are substituted tetradecyl. In certain embodiments, at least three instances of $R^B$ are fluorinated tetradecyl. In certain embodiments, at least three instances of $R^B$ are perfluorinated tetradecyl. In certain embodiments, at least three instances of $R^B$ are unsubstituted pentadecyl. In certain embodiments, at least three instances of $R^B$ are substituted pentadecyl. In certain embodiments, at least three instances of $R^B$ are fluorinated pentadecyl. In certain embodiments, at least three instances of $R^B$ are perfluorinated pentadecyl. In certain embodiments, at least three instances of $R^B$ are unsubstituted hexadecyl. In certain embodiments, at least three instances of $R^B$ are substituted hexadecyl. In certain embodiments, at least three instances of $R^B$ are fluorinated hexadecyl. In certain embodiments, at least three instances of $R^B$ are perfluorinated hexadecyl. In certain embodiments, at least three instances of $R^B$ are unsubstituted heptadecyl. In certain embodiments, at least three instances of $R^B$ are substituted heptadecyl. In certain embodiments, at least three instances of $R^B$ are fluorinated heptadecyl. In certain embodiments, at least three instances of $R^B$ are perfluorinated heptadecyl. In certain embodiments, at least three instances of $R^B$ are unsubstituted octadecyl. In certain embodiments, at least three instances of $R^B$ are substituted octadecyl. In certain embodiments, at least three instances of $R^B$ are fluorinated octadecyl. In certain embodiments, at least three instances of $R^B$ are perfluorinated octadecyl.

In certain embodiments, all instances of $R^B$ are unsubstituted alkyl. In certain embodiments, all instances of $R^B$ are substituted alkyl. In certain embodiments, all instances of $R^B$ are unbranched alkyl. In certain embodiments, all instances of $R^B$ are unbranched and unsubstituted alkyl. In certain embodiments, all instances of $R^B$ are branched alkyl. In certain embodiments, all instances of $R^B$ are unsubstituted $C_{1-24}$ alkyl. In certain embodiments, all instances of $R^B$ are substituted $C_{1-24}$ alkyl. In certain embodiments, all instances of $R^B$ are fluorinated $C_{1-24}$ alkyl. In certain embodiments, all instances of $R^B$ are unsubstituted $C_{6-24}$ alkyl. In certain embodiments, all instances of $R^B$ are substituted $C_{6-24}$ alkyl. In certain embodiments, all instances of $R^B$ are unsubstituted $C_{12-24}$ alkyl. In certain embodiments, all instances of $R^B$ are substituted $C_{12-24}$ alkyl. In certain embodiments, all instances of $R^B$ are unsubstituted $C_{18-24}$ alkyl. In certain embodiments, all instances of $R^B$ are substituted $C_{18-24}$ alkyl. In certain embodiments, all instances of $R^B$ are unsubstituted $C_{1-18}$ alkyl. In certain embodiments, all instances of $R^B$ are substituted $C_{1-18}$ alkyl. In certain embodiments, all instances of $R^B$ are unsubstituted $C_6$-18 alkyl. In certain embodiments, all instances of $R^B$ are substituted $C_{6-18}$ alkyl. In certain embodiments, all instances of $R^B$ are unsubstituted $C_{12-18}$ alkyl. In certain embodiments, all instances of $R^B$ are substituted $C_{12-18}$ alkyl. In certain embodiments, all instances of $R^B$ are unsubstituted $C_{1-12}$ alkyl. In certain embodiments, all instances of $R^B$ are substituted $C_{1-12}$ alkyl. In certain embodiments, all instances of $R^B$ are unsubstituted $C_{6-12}$ alkyl. In certain embodiments, all instances of $R^B$ are substituted $C_{6-12}$ alkyl. In certain embodiments, all instances of $R^B$ are unsubstituted $C_{1-6}$ alkyl. In certain embodiments, all instances of $R^B$ are substituted $C_{1-6}$ alkyl. In certain embodiments, all instances of $R^B$ are unsubstituted $C_{4-6}$ alkyl. In certain embodiments, all instances of $R^B$ are substituted $C_{4-6}$ alkyl. In certain embodiments, all instances of $R^B$ are unsubstituted $C_{1-4}$ alkyl. In certain embodiments, all instances of $R^B$ are substituted $C_{1-4}$ alkyl. In certain embodiments, all instances of $R^B$ are unsubstituted methyl. In certain embodiments, all instances of $R^B$ are substituted methyl. In certain embodiments, all instances of $R^B$ are —$CH_2F$. In certain embodiments, all instances of $R^B$ are —$CHF_2$. In certain embodiments, all instances of $R^B$ are —$CF_3$. In certain embodiments, all instances of $R^B$ are unsubstituted ethyl. In certain embodiments, all instances of $R^B$ are substituted ethyl. In certain embodiments, all instances of $R^B$ are fluorinated ethyl. In certain embodiments, all instances of $R^B$ are perfluorinated ethyl. In certain embodiments, all instances of $R^B$ are unsubstituted propyl. In certain embodiments, all instances of $R^B$ are substituted propyl. In certain embodiments, all instances of $R^B$ are fluorinated propyl. In certain embodiments, all instances of $R^B$ are perfluorinated propyl. In certain embodiments, all instances of $R^B$ are unsubstituted butyl. In certain embodiments, all instances of $R^B$ are substituted butyl. In certain embodiments, all instances of $R^B$ are fluorinated butyl. In certain embodiments, all instances of $R^B$ are perfluorinated butyl. In certain embodiments, all instances of $R^B$ are unsubstituted pentyl. In certain embodiments, all instances of $R^B$ are substituted pentyl. In certain embodiments, all instances of $R^B$ are fluorinated pentyl. In certain embodiments, all instances of $R^B$ are perfluorinated pentyl. In certain embodiments, all instances of $R^B$ are unsubstituted hexyl. In certain embodiments, all instances of $R^B$ are substituted hexyl. In certain embodiments, all instances of $R^B$ are fluorinated hexyl. In certain embodiments, all instances of $R^B$ are perfluorinated hexyl. In certain embodiments, all instances of $R^B$ are unsubstituted heptyl. In certain embodiments, all instances of $R^B$ are substituted heptyl. In certain embodiments, all instances of $R^B$ are fluorinated heptyl. In certain embodiments, all instances of $R^B$ are perfluorinated heptyl. In certain embodiments, all instances of $R^B$ are unsubstituted octyl. In certain embodiments, all instances of $R^B$ are substituted octyl. In certain embodiments, all instances of $R^B$ are fluorinated octyl. In certain embodiments, all instances of $R^B$ are perfluorinated octyl. In certain embodiments, all instances of $R^B$ are unsubstituted nonyl. In certain embodiments, all instances of $R^B$ are substituted nonyl. In certain embodiments, all instances of $R^B$ are fluorinated nonyl. In certain embodiments, all instances of $R^B$ are perfluorinated nonyl. In certain embodiments, all instances of $R^B$ are unsubstituted decyl. In certain embodiments, all instances of $R^B$ are substituted decyl. In certain embodiments, all instances of $R^B$ are fluorinated decyl. In certain embodiments, all instances of $R^B$ are perfluorinated decyl. In certain embodiments, all instances of $R^B$ are unsubstituted undecyl. In certain embodiments, all instances of $R^B$ are substituted undecyl. In certain embodiments, all instances of $R^B$ are fluorinated undecyl. In certain embodiments, all instances of $R^B$ are perfluorinated undecyl. In certain embodiments, all instances of $R^B$ are unsubstituted dodecyl. In certain embodiments, all instances of $R^B$ are substituted dodecyl. In certain embodiments, all instances of $R^B$ are fluorinated dodecyl. In certain embodiments, all instances of $R^B$ are perfluorinated dodecyl. In certain embodiments, all instances of $R^B$ are unsubstituted tridecyl. In certain embodiments, all instances of $R^B$ are substituted tridecyl. In certain embodiments, all instances of $R^B$ are fluorinated tridecyl. In certain embodiments, all instances of $R^B$ are perfluorinated tridecyl. In certain embodiments, all instances of $R^B$ are unsubstituted tetradecyl. In certain embodiments, all instances of $R^B$ are substituted tetradecyl. In certain embodiments, all instances of $R^B$ are fluorinated tetradecyl. In certain embodiments, all instances of $R^B$ are perfluorinated tetradecyl. In certain embodiments, all instances of $R^B$ are unsubstituted pentadecyl. In certain embodiments, all instances of $R^B$ are substituted pentadecyl. In certain embodiments, all instances of $R^B$ are fluorinated pentadecyl. In certain embodiments, all instances of $R^B$ are perfluorinated pentadecyl. In certain embodiments, all instances of $R^B$ are unsubstituted hexadecyl. In certain embodiments, all instances of $R^B$ are substituted hexadecyl. In certain embodiments, all instances of $R^B$ are fluorinated hexadecyl. In certain embodiments, all instances of $R^B$ are perfluorinated hexadecyl. In certain embodiments, all instances of $R^B$ are unsubstituted heptadecyl. In certain embodiments, all instances of $R^B$ are substituted heptadecyl. In certain embodiments, all instances of $R^B$ are fluorinated heptadecyl. In certain embodiments, all instances of $R^B$ are perfluorinated heptadecyl. In certain embodiments, all instances of $R^B$ are unsubstituted octadecyl. In certain embodiments, all instances of $R^B$ are substituted octadecyl. In certain embodiments, all instances of $R^B$ are fluorinated octadecyl. In certain embodiments, all instances of $R^B$ are perfluorinated octadecyl.

In certain embodiments, at least one instance of $R^B$ is unsubstituted acyl. In certain embodiments, at least one instance of $R^B$ is unsubstituted acetyl. In certain embodiments, at least one instance of $R^B$ is substituted acyl.

In certain embodiments, at least one instance of R is substituted carbocyclyl. In certain embodiments, at least one instance of $R^B$ is unsubstituted carbocyclyl. In certain embodiments, at least one instance of $R^B$ is saturated carbocyclyl. In certain embodiments, at least one instance of $R^B$ is unsaturated carbocyclyl. In certain embodiments, at least one instance of $R^B$ is carbocyclyl including one, two, or three double bonds in the carbocyclic ring. In certain embodiments, at least one instance of $R^B$ is monocyclic carbocyclyl. In certain embodiments, at least one instance of $R^B$ is 3- to 9-membered, monocyclic carbocyclyl. In certain embodiments, at least one instance of $R^B$ is cylcopropyl. In certain embodiments, at least one instance of $R^B$ is cyclobutyl. In certain embodiments, at least one instance of $R^B$ is cyclopentyl. In certain embodiments, at least one instance of $R^B$ is cyclohexyl. In certain embodiments, at least one instance of $R^B$ is cycloheptyl. In certain embodiments, at least one instance of $R^B$ is cyclooctyl. In certain embodiments, at least one instance of $R^B$ is cyclononyl. In certain embodiments, at least one instance of $R^B$ is bicyclic carbocyclyl. In certain embodiments, at least one instance of $R^B$ is 5- to 16-membered, bicyclic carbocyclyl.

In certain embodiments, at least one instance of $R^B$ is substituted heterocyclyl. In certain embodiments, at least one instance of $R^B$ is unsubstituted heterocyclyl. In certain embodiments, at least one instance of $R^B$ is saturated heterocyclyl. In certain embodiments, at least one instance of $R^B$ is unsaturated heterocyclyl. In certain embodiments, at least one instance of $R^B$ is heterocyclyl including one, two, or three double bonds in the heterocyclic ring. In certain embodiments, at least one instance of $R^B$ is heterocyclyl, wherein one, two, or three atoms in the heterocyclic ring are independently selected from the group consisting of nitrogen, oxygen, and sulfur. In certain embodiments, at least one instance of $R^B$ is monocyclic heterocyclyl. In certain embodiments, at least one instance of $R^B$ is 3- to 9-membered, monocyclic heterocyclyl. In certain embodiments, at least one instance of $R^B$ is bicyclic heterocyclyl. In certain embodiments, at least one instance of $R^B$ is 5- to 16-membered, bicyclic heterocyclyl.

In certain embodiments, at least one instance of $R^B$ is substituted aryl. In certain embodiments, at least one instance of $R^B$ is unsubstituted aryl. In certain embodiments, at least one instance of $R^B$ is 6- to 14-membered aryl. In certain embodiments, at least one instance of $R^B$ is 6- to 10-membered aryl. In certain embodiments, at least one instance of $R^B$ is substituted phenyl. In certain embodiments, at least one instance of $R^B$ is unsubstituted phenyl. In certain embodiments, at least one instance of $R^B$ is substituted naphthyl. In certain embodiments, at least one instance of $R^B$ is unsubstituted naphthyl.

In certain embodiments, at least one instance of $R^B$ is substituted heteroaryl. In certain embodiments, at least one instance of $R^B$ is unsubstituted heteroaryl. In certain embodiments, at least one instance of $R^B$ is heteroaryl, wherein one, two, three, or four atoms in the heteroaryl ring are independently selected from the group consisting of nitrogen, oxygen, and sulfur. In certain embodiments, at least one instance of $R^B$ is monocyclic heteroaryl. In certain embodiments, at least one instance of $R^B$ is 5-membered, monocyclic heteroaryl. In certain embodiments, at least one instance of $R^B$ is 6-membered, monocyclic heteroaryl. In certain embodiments, at least one instance of $R^B$ is pyridyl. In certain embodiments, at least one instance of $R^B$ is bicyclic heteroaryl, wherein the point of attachment may be on any atom of the bicyclic heteroaryl ring system, as valency permits. In certain embodiments, at least one instance of $R^B$ is 9-membered, bicyclic heteroaryl. In certain embodiments, at least one instance of $R^B$ is 10-membered, bicyclic heteroaryl.

In certain embodiments, all instances of $R^B$ are unsubstituted acyl. In certain embodiments, all instances of $R^B$ are unsubstituted acetyl. In certain embodiments, all instances of $R^B$ are substituted acyl.

In certain embodiments, all instances of $R^B$ are substituted carbocyclyl. In certain embodiments, all instances of $R^B$ are unsubstituted carbocyclyl. In certain embodiments, all instances of $R^B$ are saturated carbocyclyl. In certain embodiments, all instances of $R^B$ are unsaturated carbocyclyl. In certain embodiments, all instances of $R^B$ are carbocyclyl including one, two, or three double bonds in the carbocyclic ring. In certain embodiments, all instances of $R^B$ are monocyclic carbocyclyl. In certain embodiments, all instances of $R^B$ are 3- to 9-membered, monocyclic carbocyclyl. In certain embodiments, all instances of $R^B$ are cylcopropyl. In certain embodiments, all instances of $R^B$ are cyclobutyl. In certain embodiments, all instances of $R^B$ are cyclopentyl. In certain embodiments, all instances of $R^B$ are cyclohexyl. In certain embodiments, all instances of $R^B$ are cycloheptyl. In certain embodiments, all instances of $R^B$ are cyclooctyl. In certain embodiments, all instances of $R^B$ are cyclononyl. In certain embodiments, all instances of $R^B$ are bicyclic carbocyclyl. In certain embodiments, all instances of $R^B$ are 5- to 16-membered, bicyclic carbocyclyl.

In certain embodiments, all instances of $R^B$ are substituted heterocyclyl. In certain embodiments, all instances of $R^B$ are unsubstituted heterocyclyl. In certain embodiments, all instances of $R^B$ are saturated heterocyclyl. In certain embodiments, all instances of $R^B$ are unsaturated heterocyclyl. In certain embodiments, all instances of $R^B$ are heterocyclyl including one, two, or three double bonds in the heterocyclic ring. In certain embodiments, all instances of $R^B$ are heterocyclyl, wherein one, two, or three atoms in the heterocyclic ring are independently selected from the group consisting of nitrogen, oxygen, and sulfur. In certain embodiments, all instances of $R^B$ are monocyclic heterocyclyl. In certain embodiments, all instances of $R^B$ are 3- to 9-membered, monocyclic heterocyclyl. In certain embodiments, all instances of $R^B$ are bicyclic heterocyclyl. In certain embodiments, all instances of $R^B$ are 5- to 16-membered, bicyclic heterocyclyl.

In certain embodiments, all instances of $R^B$ are substituted aryl. In certain embodiments, all instances of $R^B$ are unsubstituted aryl. In certain embodiments, all instances of $R^B$ are 6- to 14-membered aryl. In certain embodiments, all instances of $R^B$ are 6- to 10-membered aryl. In certain embodiments, all instances of $R^B$ are substituted phenyl. In certain embodiments, all instances of $R^B$ are unsubstituted phenyl. In certain embodiments, all instances of $R^B$ are substituted naphthyl. In certain embodiments, all instances of $R^B$ are unsubstituted naphthyl.

In certain embodiments, all instances of $R^B$ are substituted heteroaryl. In certain embodiments, all instances of $R^B$ are unsubstituted heteroaryl. In certain embodiments, all instances of $R^B$ are heteroaryl, wherein one, two, three, or four atoms in the heteroaryl ring are independently selected from the group consisting of nitrogen, oxygen, and sulfur. In certain embodiments, all instances of $R^B$ are monocyclic heteroaryl. In certain embodiments, all instances of $R^B$ are 5-membered, monocyclic heteroaryl. In certain embodiments, all instances of $R^B$ are 6-membered, monocyclic heteroaryl. In certain embodiments, all instances of $R^B$ are pyridyl. In certain embodiments, all instances of $R^B$ are bicyclic heteroaryl, wherein the point of attachment may be on any atom of the bicyclic heteroaryl ring system, as valency permits. In certain embodiments, all instances of $R^B$ are 9-membered, bicyclic heteroaryl. In certain embodiments, all instances of $R^B$ are 10-membered, bicyclic heteroaryl.

In certain embodiments, all instances of $R^B$ are different. In certain embodiments, two instances of $R^B$ are the same. In certain embodiments, three instances of $R^B$ are the same. In certain embodiments, all instances of $R^B$ are the same.

The compounds of Formula (I) may include one or more substituents $R^C$. In certain embodiments, at least one instance of $R^C$ is H. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted $C_{1-6}$ alkyl. In certain embodiments, at least one instance of $R^C$ is fluorinated $C_{1-6}$ alkyl. In certain embodiments, at least one instance of $R^C$ is unsubstituted $C_{1-6}$ alkyl. In certain embodiments, at least one instance of $R^C$ is unsubstituted methyl. In certain embodiments, at least one instance of $R^C$ is substituted methyl. In certain embodiments, at least one instance of $R^C$ is —$CH_2F$. In certain embodiments, at least one instance of $R^C$ is —$CHF_2$. In certain embodiments, at least one instance of $R^C$ is —$CF_3$. In certain embodiments, at least one instance of $R^C$ is ethyl. In certain embodiments, at least one instance of $R^C$ is propyl. In certain embodiments, at least one instance of $R^C$ is butyl. In certain embodiments, at least one instance of $R^C$ is pentyl. In certain embodiments, at least one instance of $R^C$ is hexyl.

In certain embodiments, at least two instances of $R^C$ are H. In certain embodiments, at least two instances of $R^C$ are halogen. In certain embodiments, at least two instances of $R^C$ are F. In certain embodiments, at least two instances of $R^C$ are Cl. In certain embodiments, at least two instances of $R^C$ are Br. In certain embodiments, at least two instances of $R^C$ are I (iodine). In certain embodiments, at least two instances of Rcare substituted $C_{1-6}$ alkyl. In certain embodiments, at least two instances of $R^C$ are fluorinated $C_{1-6}$ alkyl. In certain embodiments, at least two instances of $R^C$ are unsubstituted $C_{1-6}$ alkyl. In certain embodiments, at least two instances of $R^C$ are unsubstituted methyl. In certain embodiments, at least two instances of $R^C$ are substituted methyl. In certain embodiments, at least two instances of $R^C$ are —$CH_2F$. In certain embodiments, at least two instances of $R^C$ are —$CHF_2$. In certain embodiments, at least two instances of $R^C$ are —$CF_3$. In certain embodiments, at least two instances of $R^C$ are ethyl. In certain embodiments, at least two instances of $R^C$ are propyl. In certain embodiments, at least two instances of $R^C$ are butyl. In certain embodiments, at least two instances of $R^C$ are pentyl. In certain embodiments, at least two instances of $R^C$ are hexyl.

In certain embodiments, all instances of $R^C$ are H. In certain embodiments, all instances of $R^C$ are halogen. In certain embodiments, all instances of $R^C$ are F. In certain embodiments, all instances of $R^C$ are Cl. In certain embodiments, all instances of $R^C$ are Br. In certain embodiments, all instances of $R^C$ are I (iodine). In certain embodiments, all instances of $R^C$ are substituted $C_{1-6}$ alkyl. In certain embodiments, all instances of $R^C$ are fluorinated $C_{1-6}$ alkyl. In certain embodiments, all instances of $R^C$ are unsubstituted $C_{1-6}$ alkyl. In certain embodiments, all instances of $R^C$ are unsubstituted methyl. In certain embodiments, all instances of $R^C$ are substituted methyl. In certain embodiments, all instances of $R^C$ are —$CH_2F$. In certain embodiments, all instances of $R^C$ are —$CHF_2$. In certain embodiments, all instances of $R^C$ are —$CF_3$. In certain embodiments, all instances of $R^C$ are ethyl. In certain embodiments, all instances of $R^C$ are propyl. In certain embodiments, all instances of $R^C$ are butyl. In certain embodiments, all instances of $R^C$ are pentyl. In certain embodiments, all instances of $R^C$ are hexyl.

In certain embodiments, all instances of $R^C$ are different. In certain embodiments, two instances of $R^C$ are the same. In certain embodiments, three instances of $R^C$ are the same. In certain embodiments, four instances of $R^C$ are the same. In certain embodiments, five instances of $R^C$ are the same. In certain embodiments, all instances of $R^C$ are the same.

In certain embodiments, at least one instance of n is 1. In certain embodiments, at least one instance of n is 2. In certain embodiments, at least one instance of n is 3. In certain embodiments, at least one instance of n is 4. In certain embodiments, at least one instance of n is 5. In certain embodiments, at least one instance of n is 6.

In certain embodiments, two instances of n are 1. In certain embodiments, two instances of n are 2. In certain embodiments, two instances of n are 3. In certain embodiments, two instances of n are 4. In certain embodiments, two instances of n are 5. In certain embodiments, two instances of n are 6.

The compounds of Formula (I) include substituents $R^D$. In certain embodiments, at least one instance of $R^D$ is H. In certain embodiments, at least one instance of $R^D$ is halogen. In certain embodiments, at least one instance of $R^D$ is F. In certain embodiments, at least one instance of $R^D$ is Cl. In certain embodiments, at least one instance of $R^D$ is substituted $C_{1-6}$ alkyl. In certain embodiments, at least one instance of $R^D$ is fluorinated $C_{1-6}$ alkyl. In certain embodiments, at least one instance of $R^D$ is unsubstituted $C_{1-6}$ alkyl. In certain embodiments, at least one instance of $R^D$ is unsubstituted methyl. In certain embodiments, at least one instance of $R^D$ is substituted methyl. In certain embodiments, at least one instance of $R^D$ is —$CH_2F$. In certain embodiments, at least one instance of $R^D$ is —$CHF_2$. In certain embodiments, at least one instance of $R^D$ is —$CF_3$. In certain embodiments, at least one instance of $R^D$ is ethyl. In certain embodiments, at least one instance of $R^D$ is propyl. In certain embodiments, at least one instance of $R^D$ is butyl. In certain embodiments, at least one instance of $R^D$ is pentyl. In certain embodiments, at least one instance of $R^D$ is hexyl.

In certain embodiments, at least two instances of $R^D$ are H. In certain embodiments, at least two instances of $R^D$ are halogen. In certain embodiments, at least two instances of $R^D$ are F. In certain embodiments, at least two instances of $R^D$ are Cl. In certain embodiments, at least two instances of $R^D$ are substituted $C_{1-6}$ alkyl. In certain embodiments, at least two instances of $R^D$ are fluorinated $C_{1-6}$ alkyl. In certain embodiments, at least two instances of $R^D$ are unsubstituted $C_{1-6}$ alkyl. In certain embodiments, at least two instances of $R^D$ are unsubstituted methyl. In certain embodiments, at least two instances of $R^D$ are substituted methyl. In certain embodiments, at least two instances of $R^D$ are —$CH_2F$. In certain embodiments, at least two instances of $R^D$ are —$CHF_2$. In certain embodiments, at least two instances of $R^D$ are —$CF_3$. In certain embodiments, at least two instances of $R^D$ are ethyl. In certain embodiments, at least two instances of $R^D$ are propyl. In certain embodiments, at least two instances of $R^D$ are butyl. In certain embodiments, at least two instances of $R^D$ are pentyl. In certain embodiments, at least two instances of $R^D$ are hexyl.

In certain embodiments, at least three instances of $R^D$ are H. In certain embodiments, at least three instances of $R^D$ are halogen. In certain embodiments, at least three instances of $R^D$ are F. In certain embodiments, at least three instances of $R^D$ are Cl. In certain embodiments, at least three instances of $R^D$ are substituted $C_{1-6}$ alkyl. In certain embodiments, at least three instances of $R^D$ are fluorinated $C_{1-6}$ alkyl. In certain embodiments, at least three instances of $R^D$ are unsubstituted $C_{1-6}$ alkyl. In certain embodiments, at least three instances of $R^D$ are unsubstituted methyl. In certain embodiments, at least three instances of $R^D$ are substituted methyl. In certain embodiments, at least three instances of $R^D$ are —$CH_2F$. In certain embodiments, at least three instances of $R^D$ are —$CHF_2$. In certain embodiments, at least three instances of $R^D$ are —$CF_3$. In certain embodiments, at least three instances of $R^D$ are ethyl. In certain embodiments, at least three instances of $R^D$ are propyl. In certain embodiments, at least three instances of $R^D$ are butyl. In certain embodiments, at least three instances of $R^D$ are pentyl. In certain embodiments, at least three instances of $R^D$ are hexyl.

In certain embodiments, all instances of $R^D$ are H. In certain embodiments, all instances of $R^D$ are halogen. In certain embodiments, all instances of $R^D$ are F. In certain embodiments, all instances of $R^D$ are Cl. In certain embodiments, all instances of $R^D$ are substituted $C_{1-6}$ alkyl. In certain embodiments, all instances of $R^D$ are fluorinated $C_{1-6}$ alkyl. In certain embodiments, all instances of $R^D$ are unsubstituted $C_{1-6}$ alkyl. In certain embodiments, all instances of $R^D$ are unsubstituted methyl. In certain embodiments, all instances of $R^D$ are substituted methyl. In certain embodiments, all instances of $R^D$ are —$CH_2F$. In certain embodiments, all instances of $R^D$ are —$CHF_2$. In certain embodiments, all instances of $R^D$ are —$CF_3$. In certain embodiments, all instances of $R^D$ are ethyl. In certain embodiments, all instances of $R^D$ are propyl. In certain embodiments, all instances of $R^D$ are butyl.

In certain embodiments, all instances of $R^D$ are the same.

The compounds of Formula (I) include substituents $R^E$. In certain embodiments, at least one instance of $R^E$ is H. In certain embodiments, at least one instance of $R^E$ is halogen. In certain embodiments, at least one instance of $R^E$ is F. In certain embodiments, at least one instance of $R^E$ is Cl. In certain embodiments, at least one instance of $R^E$ is substituted $C_{1-6}$ alkyl. In certain embodiments, at least one instance of $R^E$ is fluorinated $C_{1-6}$ alkyl. In certain embodiments, at least one instance of $R^E$ is unsubstituted $C_{1-6}$ alkyl. In certain embodiments, at least one instance of $R^E$ is unsubstituted methyl. In certain embodiments, at least one instance of $R^E$ is substituted methyl. In certain embodiments, at least one instance of $R^E$ is —$CH_2F$. In certain embodiments, at least one instance of $R^E$ is —$CHF_2$. In certain embodiments, at least one instance of $R^E$ is —$CF_3$. In certain embodiments, at least one instance of $R^E$ is ethyl. In certain embodiments, at least one instance of $R^E$ is propyl. In certain embodiments, at least one instance of $R^E$ is butyl.

In certain embodiments, both instances of $R^E$ are H. In certain embodiments, both instances of $R^E$ are halogen. In certain embodiments, both instances of $R^E$ are F. In certain embodiments, both instances of $R^E$ are Cl. In certain embodiments, both instances of $R^E$ are substituted $C_{1-6}$ alkyl. In certain embodiments, both instances of $R^E$ are fluorinated $C_{1-6}$ alkyl. In certain embodiments, both instances of $R^E$ are unsubstituted $C_{1-6}$ alkyl. In certain embodiments, both instances of $R^E$ are unsubstituted methyl. In certain embodiments, both instances of $R^E$ are substituted methyl. In certain embodiments, both instances of $R^E$ are —$CH_2F$. In certain embodiments, both instances of $R^E$ are —$CHF_2$. In certain embodiments, both instances of $R^E$ are —$CF_3$. In certain embodiments, both instances of $R^E$ are ethyl. In certain embodiments, both instances of $R^E$ are propyl. In certain embodiments, both instances of $R^E$ are butyl. In certain embodiments, both instances of $R^E$ are pentyl. In certain embodiments, both instances of $R^E$ are hexyl.

The compounds of Formula (I) may include one or more substituents $R^F$. In certain embodiments, at least one instance of $R^F$ is H. In certain embodiments, at least one instance of $R^F$ is halogen. In certain embodiments, at least one instance of $R^F$ is F. In certain embodiments, at least one instance of $R^F$ is Cl. In certain embodiments, at least one instance of $R^F$ is Br. In certain embodiments, at least one instance of $R^F$ is I (iodine). In certain embodiments, at least one instance of $R^F$ is substituted $C_{1-6}$ alkyl. In certain embodiments, at least one instance of $R^F$ is fluorinated $C_{1-6}$ alkyl. In certain embodiments, at least one instance of $R^F$ is unsubstituted $C_{1-6}$ alkyl. In certain embodiments, at least one instance of $R^F$ is unsubstituted methyl. In certain embodiments, at least one instance of $R^F$ is substituted methyl. In certain embodiments, at least one instance of $R^F$ is —CH$_2$F. In certain embodiments, at least one instance of $R^F$ is —CHF$_2$. In certain embodiments, at least one instance of $R^F$ is —CF$_3$. In certain embodiments, at least one instance of $R^F$ is ethyl. In certain embodiments, at least one instance of $R^F$ is propyl. In certain embodiments, at least one instance of $R^F$ is butyl. In certain embodiments, at least one instance of $R^F$ is pentyl. In certain embodiments, at least one instance of $R^F$ is hexyl.

In certain embodiments, at least two instances of $R^F$ are H. In certain embodiments, at least two instances of $R^F$ are halogen. In certain embodiments, at least two instances of $R^F$ are F. In certain embodiments, at least two instances of $R^F$ are Cl. In certain embodiments, at least two instances of $R^F$ are Br. In certain embodiments, at least two instances of $R^F$ are I (iodine). In certain embodiments, at least two instances of $R^F$ are substituted $C_{1-6}$ alkyl. In certain embodiments, at least two instances of $R^F$ are fluorinated $C_{1-6}$ alkyl. In certain embodiments, at least two instances of $R^F$ are unsubstituted $C_{1-6}$ alkyl. In certain embodiments, at least two instances of $R^F$ are unsubstituted methyl. In certain embodiments, at least two instances of $R^F$ are substituted methyl. In certain embodiments, at least two instances of $R^F$ are —CH$_2$F. In certain embodiments, at least two instances of $R^F$ are —CHF$_2$. In certain embodiments, at least two instances of $R^F$ are —CF$_3$. In certain embodiments, at least two instances of $R^F$ are ethyl. In certain embodiments, at least two instances of $R^F$ are propyl. In certain embodiments, at least two instances of $R^F$ are butyl. In certain embodiments, at least two instances of $R^F$ are pentyl. In certain embodiments, at least two instances of $R^F$ are hexyl.

In certain embodiments, all instances of $R^F$ are H. In certain embodiments, all instances of $R^F$ are halogen. In certain embodiments, all instances of $R^F$ are F. In certain embodiments, all instances of $R^F$ are Cl. In certain embodiments, all instances of $R^F$ are Br. In certain embodiments, all instances of $R^F$ are I (iodine). In certain embodiments, all instances of $R^F$ are substituted $C_{1-6}$ alkyl. In certain embodiments, all instances of $R^F$ are fluorinated $C_{1-6}$ alkyl. In certain embodiments, all instances of $R^F$ are unsubstituted $C_{1-6}$ alkyl. In certain embodiments, all instances of $R^F$ are unsubstituted methyl. In certain embodiments, all instances of $R^F$ are substituted methyl. In certain embodiments, all instances of $R^F$ are —CH$_2$F. In certain embodiments, all instances of $R^F$ are —CHF$_2$. In certain embodiments, all instances of $R^F$ are —CF$_3$. In certain embodiments, all instances of $R^F$ are ethyl. In certain embodiments, all instances of $R^F$ are propyl. In certain embodiments, all instances of $R^F$ are butyl. In certain embodiments, all instances of $R^F$ are pentyl. In certain embodiments, all instances of $R^F$ are hexyl.

In certain embodiments, all instances of $R^F$ are different. In certain embodiments, two instances of $R^F$ are the same. In certain embodiments, three instances of $R^F$ are the same. In certain embodiments, four instances of $R^F$ are the same. In certain embodiments, five instances of $R^F$ are the same. In certain embodiments, all instances of $R^F$ are the same.

In certain embodiments, moiety —(C($R^F$)$_2$)$_m$— of compounds of Formula (I) is —(CH$_2$)$_2$—. In certain embodiments, moiety —(C($R^F$)$_2$)$_m$— of compounds of Formula (I) is —(CH$_2$)$_3$—. In certain embodiments, moiety —(C($R^F$)$_2$)$_m$— of compounds of Formula (I) is —(CH$_2$)$_4$—.

In certain embodiments, m is 2. In certain embodiments, m is 3. In certain embodiments, m is 4. In certain embodiments, m is 5. In certain embodiments, m is 6.

In certain embodiments, k is 0. In certain embodiments, k is 1.

In certain embodiments, the compound of Formula (I) is of the formula:

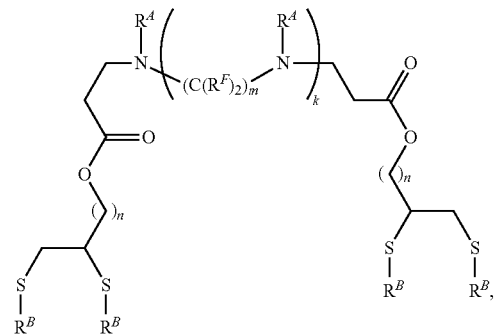

or a salt or stereoisomer thereof.

In certain embodiments, the compound of Formula (I) is of the formula:

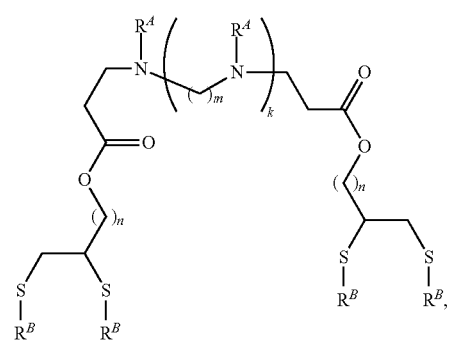

or a salt or stereoisomer thereof.

In certain embodiments, the compound of Formula (I) is of Formula (I-B):

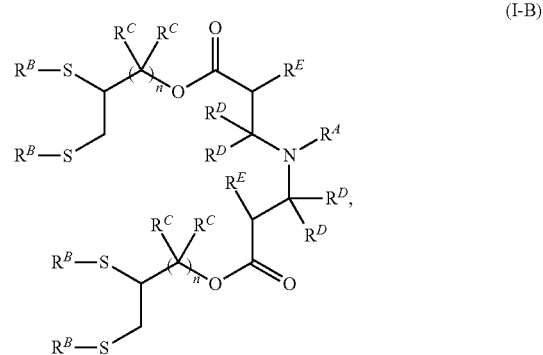

(I-B)

or a salt or stereoisomer thereof.

In certain embodiments, the compound of Formula (I) is of Formula (I-B-1):

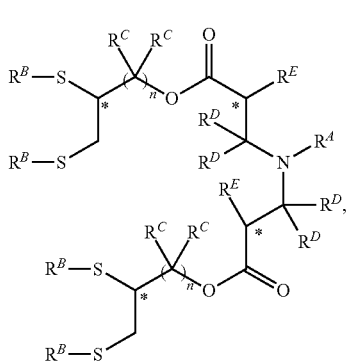
(I-B-1)

wherein the stereochemistry of each one of the carbon atoms labeled with "*" is independently S or R. In certain embodiments, the compounds of Formula (I-B-1) are a mixture of stereoisomers. In certain embodiments, the compounds of Formula (I-B-1) are a racemic mixture of stereoisomers.

In certain embodiments, the compound of Formula (I) is of Formula (I-B-2):

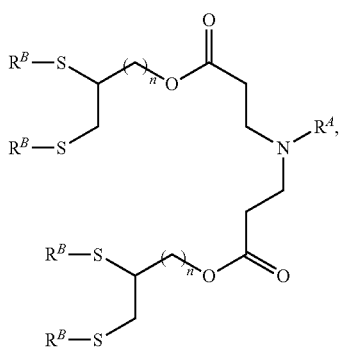
(I-B-2)

or a salt or stereoisomer thereof.

In certain embodiments, the compound of Formula (I) is of Formula (I-B-3):

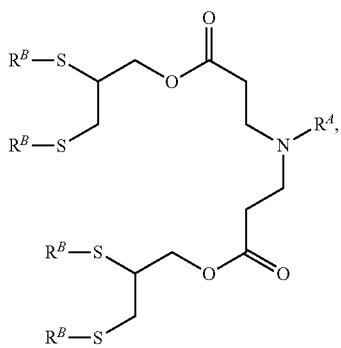
(I-B-3)

or a salt or stereoisomer thereof.

In certain embodiments, the compound of Formula (I) is of the formula:

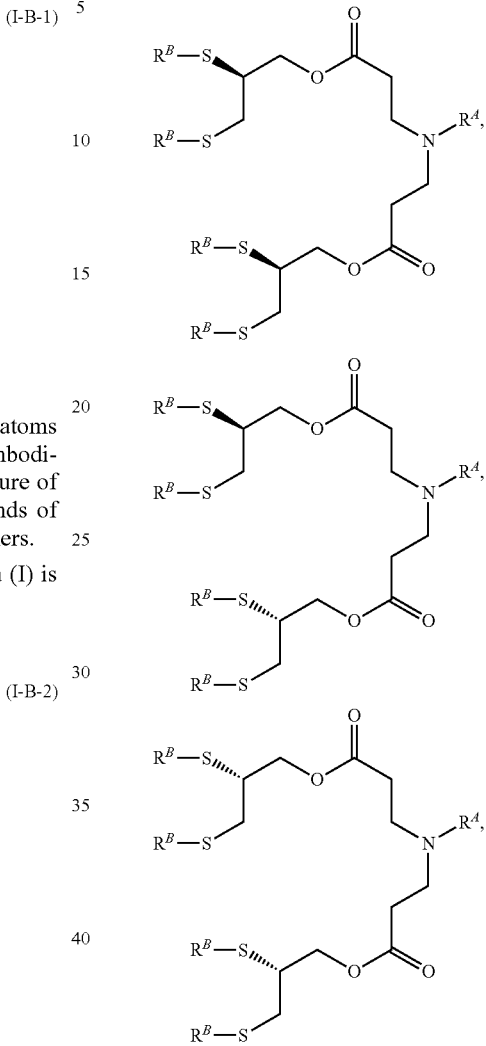

or a salt or stereoisomer thereof.

In certain embodiments, the compound of Formula (I) is of Formula (I-C):

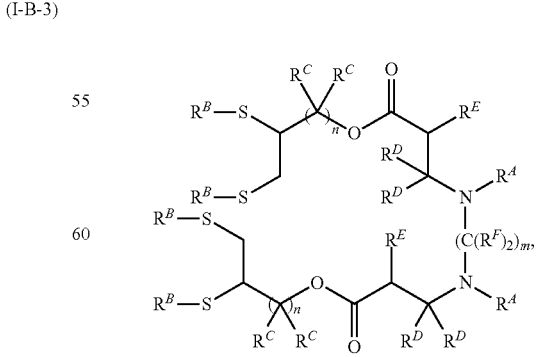
(I-C)

or a salt or stereoisomer thereof.

In certain embodiments, the compound of Formula (I) is of Formula (I-C-1):

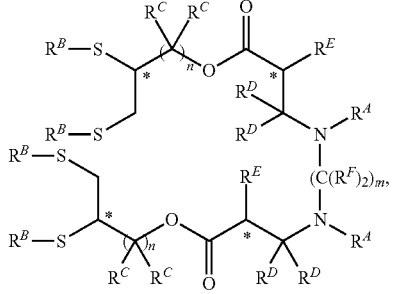

wherein the stereochemistry of each one of the carbon atoms labeled with "*" is independently S or R. In certain embodiments, the compounds of Formula (I-C-C) are a mixture of stereoisomers. In certain embodiments, the compounds of Formula (I-C-1) are a racemic mixture of stereoisomers.

In certain embodiments, the compound of Formula (I) is of the formula:

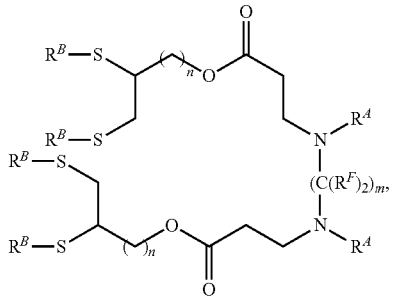

or a salt or stereoisomer thereof.

In certain embodiments, the compound of Formula (I) is of Formula (I-C-2):

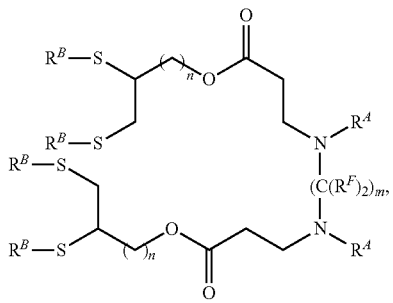

or a salt or stereoisomer thereof.

In certain embodiments, the compound of Formula (I) is of Formula (I-C-3):

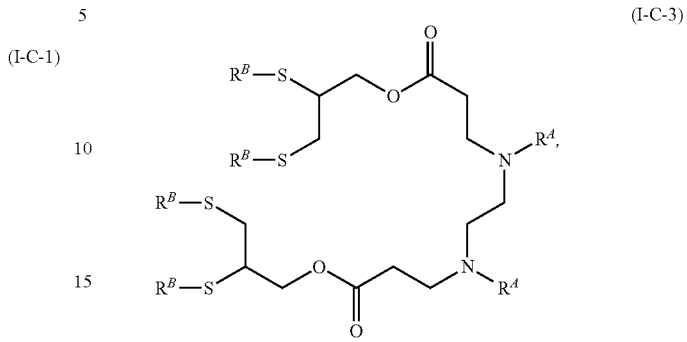

or a salt or stereoisomer thereof.

In certain embodiments, the compound of Formula (I) is of the formula:

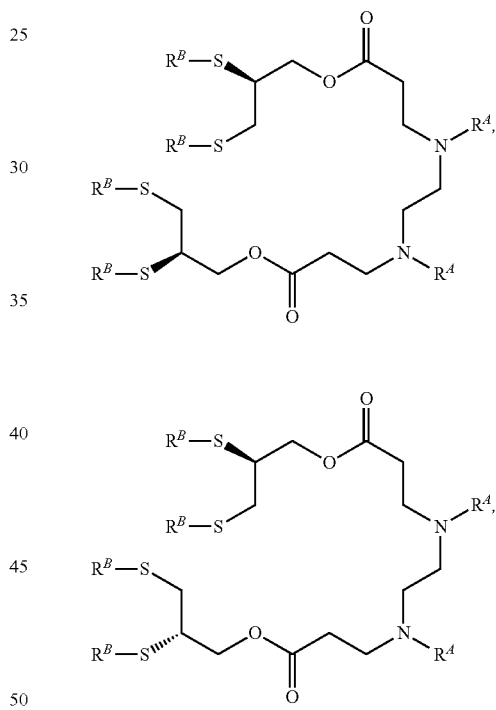

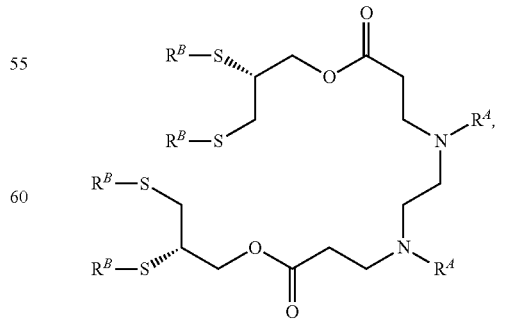

or a salt or stereoisomer thereof.

In certain embodiments, the compound of Formula (I) is of any one of Formulae (I-1) to (I-31):
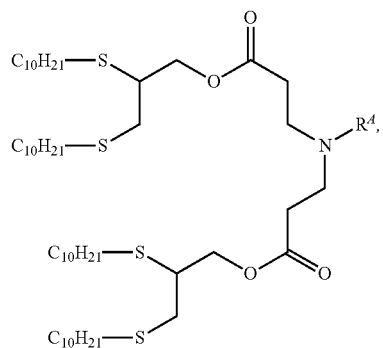
wherein $R^A$ is one of the formulae:
(I-1)
(I-2)
(I-3)
(I-4)
(I-5)
(I-6)
(I-7)
(I-8)
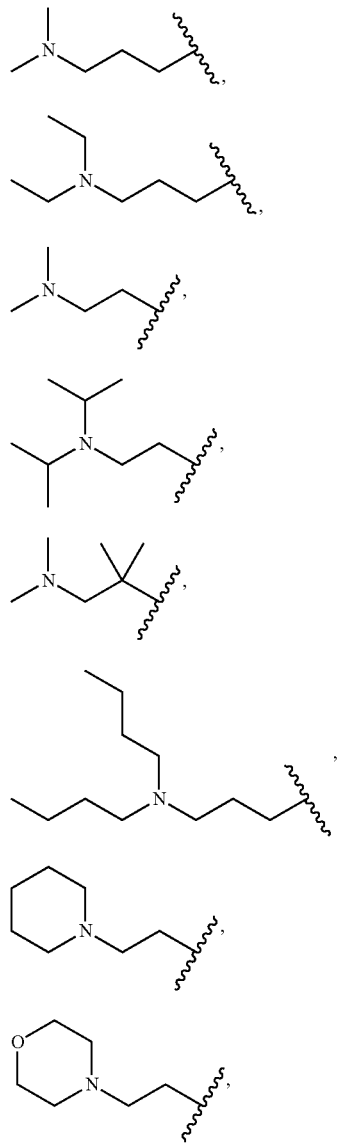
(I-9)
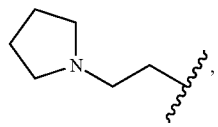
(I-10)
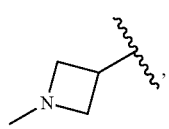
(I-11)
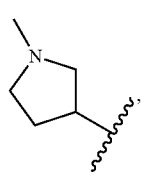
(I-12)
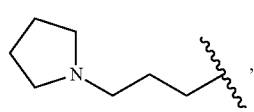
(I-13)
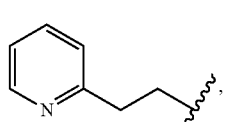
(I-14)
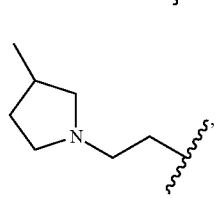
(I-15)
(I-16)
(I-17)
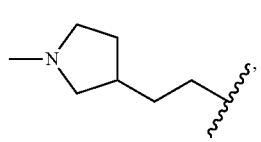
(I-18)
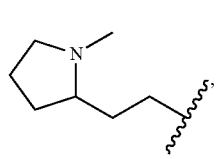
(I-19)
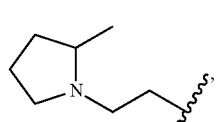
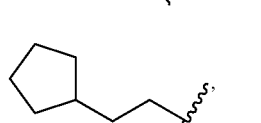
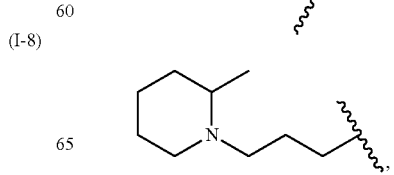

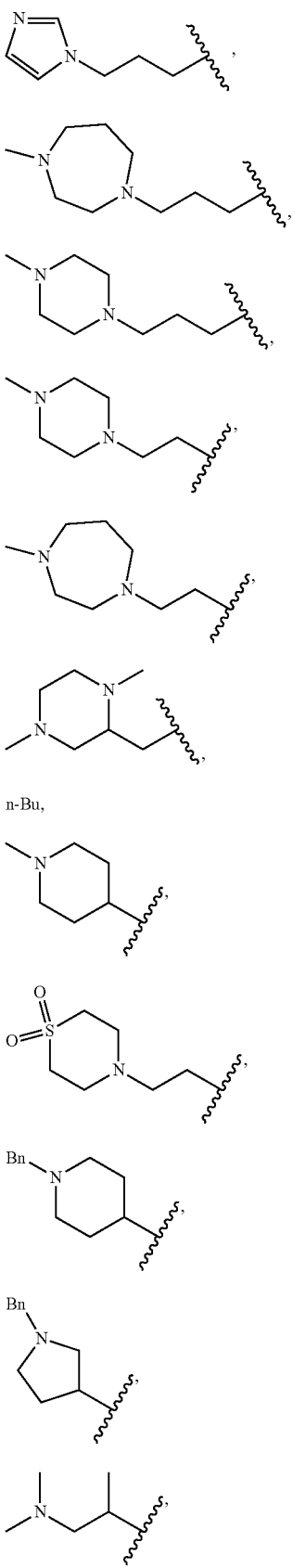

(I-20), (I-21), (I-22), (I-23), (I-24), (I-25), (I-26), (I-27), (I-28), (I-29), (I-30), (I-31)

and salts and stereoisomers thereof.

In certain embodiments, the compound of Formula (I) is of Formula (I-32):

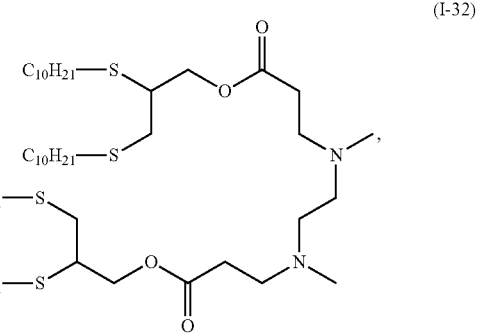

(I-32)

or a salt or stereoisomer thereof.

The compounds of the invention or, in other words, the inventive compounds or lipids, include the compounds described herein, and salts and stereoisomers thereof. In certain embodiments, the compounds of the invention are the compounds described herein, and salts thereof. In certain embodiments, the compounds of the invention are the compounds described herein, and pharmaceutical acceptable salts thereof. In certain embodiments, the compounds of the invention are the compounds of Formula (I), and salts and stereoisomers thereof. In certain embodiments, the compounds of the invention are the compounds of Formula (I), and salts thereof. In certain embodiments, the compounds of the invention are the compounds of Formula (I), and pharmaceutical acceptable salts thereof.

In certain embodiments, the compounds of the invention are not dendrimers. In certain embodiments, each instance of $R^A$ of a compound of Formula (I) is not of the formula:

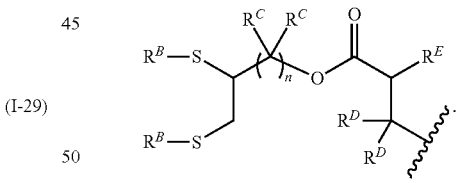

In certain embodiments, each instance of $R^A$ of a compound of Formula (I) is not of the formula:

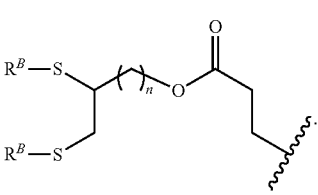

In certain embodiments, each instance of $R^A$ of a compound of Formula (I) is not of the formula:

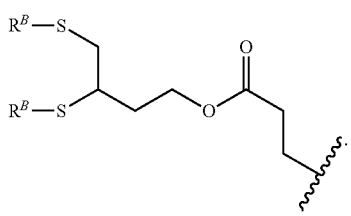

In certain embodiments, each instance of $R^4$ of a compound of Formula (I) is not of the formula:

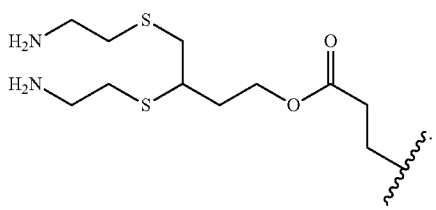 [SMILES: *CCC(=O)OCCC(CSCCN)SCCN]

In certain embodiments, the compound of Formula (I) is not of the formula:

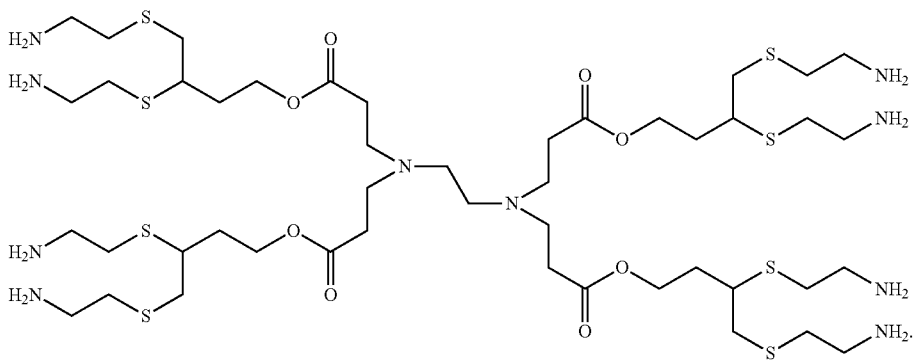 [SMILES: NCCSCC(CCOC(=O)CCN(CCC(=O)OCCC(CSCCN)SCCN)CCN(CCC(=O)OCCC(CSCCN)SCCN)CCC(=O)OCCC(CSCCN)SCCN)SCCN]

The compounds of the invention may be useful in treating and/or preventing a disease (e.g., a genetic disease, proliferative disease, hematological disease, neurological disease, immunological disease, gastrointestinal disease (e.g., liver disease), respiratory disease (e.g., lung disease), painful condition, psychiatric disorder, metabolic disorder, or spleen disease) in a subject in need thereof. In certain embodiments, the inventive compounds are useful in gene therapy. For example, the compounds of the invention may be useful in delivering an agent, such as a polynucleotide (e.g., an siRNA, mRNA, plasmid DNA, or a combination thereof), to a subject in need thereof.

Compositions

The present invention provides compositions comprising a compound of the invention (e.g., a compound of Formulae (I), or a salt or stereoisomer thereof), an agent (e.g., a pharmaceutical agent or diagnostic agent), and optionally an excipient. In certain embodiments, the compositions of the invention are pharmaceutical compositions. In certain embodiments, the compositions are compositions for non-medical applications. In certain embodiments, the compositions are cosmetic compositions. In certain embodiments, the compositions are dietary compositions. In certain embodiments, the compositions are nutraceutical compositions. In certain embodiments, a composition of the invention comprises a compound of Formula (I), or a salt thereof, and optionally an excipient. In certain embodiments, a composition of the invention comprises a compound of Formula (I), or a pharmaceutically acceptable salt thereof, and optionally a pharmaceutically acceptable excipient.

The compositions of the invention comprise one or more agents. The agents are described in more detail herein. In an inventive composition, an agent may form a complex with a compound of the invention. The complexes are described in more detail herein. In certain embodiments, the composition is useful in the delivery of the agent to a subject in need thereof. In certain embodiments, the composition is useful in the delivery of an effective amount of the agent to the subject. In certain embodiments, the agent is covalently attached to the compound of the invention in the inventive composition. In certain embodiments, the agent is not covalently attached to the compound of the invention in the inventive composition.

The inventive compositions comprising an agent may improve or increase the delivery of the agent to a subject, tissue, or cell. In certain embodiments, the compositions of the invention increase the delivery of the agent to a target tissue or target cell. In certain embodiments, the compositions selectively deliver the agent to the target tissue or target cell (e.g., the compositions deliver more agent to the target tissue than to a non-target tissue or deliver more agent to the target cell than to a non-target cell). In certain embodiments, the compositions increase the delivery of the agent to the liver of the subject. In certain embodiments, the compositions increase the delivery of the agent to the spleen of the subject. In certain embodiments, the compositions increase the delivery of the agent to the lung of the subject. In certain embodiments, the compositions selectively deliver the agent to the liver, spleen, and/or lung of the subject. In certain embodiments, the compositions increase the delivery of the agent to a liver cell. In certain embodiments, the compositions increase the delivery of the agent to a spleen cell. In certain embodiments, the compositions increase the delivery of the agent to a lung cell. In certain embodiments, the compositions selectively deliver the agent to the liver, spleen, and/or lung cell.

The delivery of the agent may be characterized in various ways, such as the exposure, concentration, and bioavailability of the agent. The exposure of an agent in a subject may be defined as the area under the curve (AUC) of the concentration of the agent in the subject or cell after administration or dosing. In certain embodiments, the exposure described herein is the exposure of the agent in a target tissue (e.g., liver, spleen, or lung) of the subject. In general, an increase in exposure may be calculated by taking the difference in the AUC measured in a subject or cell between those of an inventive composition and a control composition, and dividing the difference by the exposure of the control composition. Exposure of an agent may be measured in an appropriate animal model. The concentration of an agent and, when appropriate, its metabolite(s), in a subject or cell is measured as a function of time after administration.

In certain embodiments, the concentration described herein is the concentration of the agent in a target tissue (e.g., liver, spleen, or lung) of the subject. Concentration of an agent, and, when appropriate, of its metabolite(s), in a subject or cell, may be measured as a function of time in vivo using an appropriate animal model. One method of determining the concentration of an agent involves dissecting of a tissue or organ of the subject. The concentration of the agent in the subject or cell may be determined by HPLC or LC/MS analysis.

In some embodiments, the delivery of the agent increases due to the presence of an inventive compound in the composition. In some embodiments, the delivery of the agent increases due to the presence of a complex formed between an inventive compound and the agent in the composition. In some embodiments, the compositions of the invention increase the delivery of the agent by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, or at least about 1000-fold. In certain embodiments, the compositions of the invention increase the delivery of the agent by less than about 1000-fold, less than about 300-fold, less than about 100-fold, less than about 30-fold, less than about 10-fold, less than about 3-fold, less than about 2-fold, less than about 100%, less than about 50%, less than about 30%, less than about 20%, or less than about 10%. Combinations of the above-referenced ranges are also possible (e.g., an increase of at least about 100% and less than about 10 fold). Other ranges are also within the scope of the invention. In certain embodiments, a compound of the invention is present in the composition in a sufficient amount to increase the delivery of the agent by an amount described herein when administered in the composition compared to the delivery of the agent when administered in the absence of a compound of the invention.

The compositions of the invention may deliver an agent selectively to a tissue or organ of a subject. In certain embodiments, the tissue or organ to which the agent is selectively delivered to is a target tissue. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the agent to a target tissue than to a non-target tissue. The amount of agent may be measured by the exposure, concentration, and/or bioavailability of the agent in a tissue or organ as described herein. In certain embodiments, the compositions deliver at most about 1000-fold, at most about 300-fold, at most about 100-fold, at most about 30-fold, at most about 10-fold, at most about 3-fold, at most about 100%, at most about 70%, at most about 50%, at most about 40%, at most about 30%, at most about 20%, or at most about 10% more amount of the agent to a target tissue than to a non-target tissue. Combinations of the above ranges (e.g., at least about 100% and at most about 10 fold) are also with the scope of the invention. In certain embodiments, the target tissue is the liver. In certain embodiments, the target tissue is the spleen. In certain embodiments, In certain embodiments, the target tissue is the lung.

The inventive compositions (e.g., pharmaceutical compositions) including one or more agents (e.g., pharmaceutical agents) may be useful in treating and/or preventing a disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing an immunological disease. In certain embodiments, the compositions are useful for treating and/or preventing a gastrointestinal disease (e.g., liver disease). In certain embodiments, the compositions are useful for treating and/or preventing a respiratory disease (e.g., lung disease). In certain embodiments, the compositions are useful for treating and/or preventing a painful condition. In certain embodiments, the compositions are useful for treating and/or preventing a psychiatric disorder. In certain embodiments, the compositions are useful for treating and/or preventing a metabolic disorder. In certain embodiments, the compositions are useful for treating and/or preventing a spleen disease. In certain embodiments, the compositions are useful for treating and/or preventing hepatic carcinoma, hypercholesterolemia, refractory anemia, or familial amyloid neuropathy.

The agents may be provided in an effective amount in a composition of the invention. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease. In certain embodiments, the effective amount is an amount effective for treating and/or preventing a genetic disease. In certain embodiments, the effective amount is an amount effective for treating and/or preventing a proliferative disease. In certain embodiments, the effective amount is an amount effective for treating and/or preventing cancer. In certain embodiments, the effective amount is an amount effective for treating and/or preventing a benign neoplasm. In certain embodiments, the effective amount is an amount effective for treating and/or preventing pathological angiogenesis. In certain embodiments, the effective amount is an amount effective for treating and/or preventing an inflammatory disease. In certain embodiments, the effective amount is an amount effective for treating and/or preventing an autoimmune disease. In certain embodiments, the effective amount is an amount effective for treating and/or preventing a hematological disease. In certain embodiments, the effective amount is an amount effective for treating and/or preventing a neurological disease. In certain embodiments, the effective amount is an amount effective for treating and/or preventing an immunological disease. In certain embodiments, the effective amount is an amount effective for treating and/or preventing a gastrointestinal disease (e.g., liver disease). In certain embodiments, the effective amount is an amount effective for treating and/or preventing a respiratory disease (e.g., lung disease). In certain embodiments, the effective amount is an amount effective for treating and/or preventing a painful condition. In certain embodiments, the effective amount is an amount effective for treating and/or preventing a psychiatric disorder. In certain embodiments, the effective amount is an amount effective for treating and/or preventing a metabolic disorder. In certain embodiments, the effective amount is an amount effective for treating and/or preventing a spleen disease. In certain embodiments, the effective amount is an amount effective for treating and/or preventing hepatic carcinoma, hypercholesterolemia, refractory anemia, or familial amyloid neuropathy.

An effective amount of an agent may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the compositions of the invention are in the form of a particle. In certain embodiments, the particle is a nanoparticle or microparticle. In certain embodiments, the compositions are in the form of liposomes or micelles. It is understood that, in certain embodiments, the particles, micelles, or liposomes described herein result from self-assembly of the components of the composition. In certain embodiments, the particle, micelle, or liposome encapsulates an agent. The agent to be delivered by the particle, micelle, or liposome may be in the form of a gas, liquid, or solid. The compounds of the invention may be combined with polymers (synthetic or natural), surfactants, cholesterol, carbohydrates, proteins, lipids, lipidoids, etc. to form the particles. These particles may be further combined with an excipient to form the compositions of the invention. The particles, micelles, and liposomes are described in more detail herein.

The compositions described herein (e.g., pharmaceutical compositions) can be prepared by any method known in the art (e.g., pharmacology). In general, such preparatory methods include the steps of bringing a compound of the invention into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A "unit dose" is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition of the invention will vary, depending upon the identity, size, and/or condition of the subject treated and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms*. Mol Ther. 18 (7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a composition of this invention may include ointments, pastes, creams, lotions, gels, powders, solutions, sprays, inhalants, and/or patches. Generally, the active ingredient is admixed under sterile conditions with a carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, a composition of the invention is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

The compositions of the invention may include a hydrophilic polymer (e.g., polyethylene glycol (PEG)) and/or a lipid (e.g., a triglyceride, a driglyceride, a PEGylated lipid, a phospholipid (e.g., 1,2-distearoyl-sn-glycero-3-phosphocholine (DSPC)), a cholesterol, a apolipoprotein, or a combination thereof) in addition to a compound of the invention and an agent described herein. In certain embodiments, the compositions include two components selected from the group consisting of the following components: a hydrophilic polymer, a triglyceride, a driglyceride, a PEGylated lipid, a phospholipid, a cholesterol, and a apolipoprotein. In certain embodiments, the compositions include three components selected from the group consisting of the following components: a hydrophilic polymer, a triglyceride, a driglyceride, a PEGylated lipid, a phospholipid, a cholesterol, and a apolipoprotein. In certain embodiments, the compositions include at least four components selected from the group consisting of the following components: a hydrophilic polymer, a triglyceride, a driglyceride, a PEGylated lipid, a phospholipid, a cholesterol, and a apolipoprotein. In certain embodiments, the compositions include a hydrophilic polymer, a phospholipid, and a cholesterol. In certain embodiments, the compositions include PEG, DSPC, and cholesterol.

The compositions of the invention may be useful in other applications, e.g., non-medical applications. Nutraceutical compositions of the invention may be useful in the delivery of an effective amount of a nutraceutical, e.g., a dietary supplement, to a subject in need thereof. Cosmetic compositions of the invention may be formulated as a cream, ointment, balm, paste, film, or liquid, etc., and may be useful in the application of make-up, hair products, and materials useful for personal hygiene, etc. Compositions of the invention may be useful for other non-medical applications, e.g., such as an emulsion, emulsifier, or coating, useful, for example, as a food component, for extinguishing fires, for disinfecting surfaces, for oil cleanup, etc.

Agents

Agents that are delivered by the systems (e.g., pharmaceutical compositions) described herein may be (e.g., therapeutic or prophylactic), diagnostic, cosmetic, or nutraceutical agents. Any chemical compound to be administered to a subject may be delivered using the complexes, picoparticles, nanoparticles, microparticles, micelles, or liposomes, described herein. The agent may be an organic molecule, inorganic molecule, nucleic acid, protein, peptide, polynucleotide, targeting agent, an isotopically labeled chemical compound, vaccine, or an immunological agent. The agent may be an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a cell may be delivered to the subject or cell using the compositions of the invention.

The agents included in the compositions of the invention may be independently selected from the group consisting of small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, and agents useful in bioprocessing. The targeting agents are described in more detail herein. In certain embodiments, the agents are nutraceutical agents. In certain embodiments, the agents are agents. In certain embodiments, the agent is a therapeutic or prophylactic agent. In certain embodiments, the agent is an antibiotic agent (e.g., anti-bacterial agent, anti-viral agent, anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anticholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts.

Therapeutic and prophylactic agents may be combined with interleukins, interferon, cytokines, and adjuvants such as cholera toxin, alum, and Freund's adjuvant, etc.

In certain embodiments, the agents include a polynucleotide. In certain embodiments, the agents include a DNA. In certain embodiments, the agents include a plasmid DNA (pDNA). In certain embodiments, the agents include a genomic DNA (gDNA). In certain embodiments, the agents include a complementary DNA (cDNA). In certain embodiments, the agents include a RNA. In certain embodiments, the agents include a small interfering RNA (siRNA). In certain embodiments, the agents include a messenger RNA (mRNA). In certain embodiments, the agents include a double-stranded RNA (dsRNA), small hairpin RNA (shRNA), microRNA (miRNA), transfer RNA (tRNA), or antisense RNA (asRNA). In certain embodiments, the agents include a pDNA, siRNA, or a combination thereof. In certain embodiments, the agents include a pDNA, siRNA, mRNA, or a combination thereof. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the agents include an siRNA. In certain embodiments, the agents include a dsRNA. In certain embodiments, the agents include an shRNA. In certain embodiments, the agents include an miRNA. miRNAs are genomically encoded non-coding RNAs of about 21-23 nucleotides in length that help regulate gene expression, particularly during development. See, e.g., Bartel, 2004, *Cell*, 116:281; Novina and Sharp, 2004, *Nature*, 430:161; and U.S. Patent Application Publication, US 2005/0059005; Wang et al., 2007, *Front. Biosci.*, 12:3975; and Zhao, 2007, *Trends Biochem. Sci.*, 32:189. In certain embodiments, the agents include an mRNA. In certain embodiments, the agents include a tRNA. In certain embodiments, the agents include an asRNA. In certain embodiments, the agents include a combination of pDNA and siRNA. In certain embodiments, upon delivery of an RNA into a subject or cell, the RNA is able to interfere with the expression of a specific gene in the subject or cell.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, siRNA, dsRNA, shRNA, miRNA, mRNA, tRNA, asRNA, and/or RNAi can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, RNA, 13:1765; Yiu et al., 2005, *Bioinformatics*, 21:144; and Jia et al., 2006, *BMC Bioinformatics*, 7: 271.

The polynucleotide included in a composition of the invention may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes less than about 10,000, less than about 3,000, less than about 1,000, less than about 300, less than about 100, or less than about 30 base pairs. Combinations of the above ranges (e.g., at least about 100 and less than about 1,000) are also within the scope of the invention. The polynucleotide may be provided by any means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and end-capping, etc. In certain embodiments, the modifications lead to increased stability of the polynucleotide.

Wherever a polynucleotide is employed in the present invention, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyluridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, and an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, and insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription, etc. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, hepatitis E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

In certain embodiments, the agent in a composition of the invention that is delivered to a subject in need thereof may be a mixture of two or more agents that may be useful as, e.g., combination therapies. The compositions including the two or more agents can be administered to achieve a synergistic effect. In certain embodiments, the compositions including the two or more agents can be administered to improve the activity and/or bioavailability, reduce and/or modify the metabolism, inhibit the excretion, and/or modify the distribution within the body of a subject, of each one of the two or more agents. It will also be appreciated that the therapy employed may achieve a desired effect for the same disorder, and/or it may achieve different effects.

The compositions (e.g., pharmaceutical compositions) of the invention can be administered concurrently with, prior to, or subsequent to the one or more agents (e.g., pharmaceutical agents). The two or more agents may be useful for treating and/or preventing a same disease or different diseases described herein. Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, compounds of the invention, and the complexes, liposomes, micelles, and particles (e.g., microparticles and nanoparticles) thereof, may be modified to include targeting moieties. For example, the compounds of the invention may include a targeting moiety. A variety of agents or regions that target particular cells are known in the art. See, e.g., Cotten et al., *Methods Enzym.* 217:618, 1993. The targeting agent may be included throughout a particle of a compound of the invention or may be only on the surface of the particle. The targeting agent may be a protein, peptide, carbohydrate, glycoprotein, lipid, small molecule, or polynucleotide, etc. The targeting agent may be used to target specific cells or tissues or may be used to promote endocytosis or phagocytosis of the particle. Examples of targeting agents include, but are not limited to, antibodies, fragments of antibodies, proteins, peptides, carbohydrates, receptor ligands, sialic acid, and aptamers, etc. If the targeting agent is included throughout a particle, the targeting agent may be included in the mixture that is used to form the particle. If the targeting agent is only on the surface of a particle, the targeting agent may be associated with (e.g., by covalent or non-covalent (e.g., electrostatic, hydrophobic, hydrogen bonding, van der Waals, π-π stacking) interactions) the formed particle using standard chemical techniques.

Complexes of an Agent and a Compound of the Invention

The present invention contemplates that the compounds of the invention are useful in the delivery of one or more agents (such as a polynucleotide (e.g., DNA (e.g., pDNA) or RNA (e.g., siRNA, mRNA), synthetic analogs of DNA and/or RNA, and DNA/RNA hybrids, etc.)) to a subject in need thereof. Without wishing to be bound by any particular theory, the compounds of the invention have several desirable properties that make a composition including the inventive compound and an agent suitable for delivering the agent to a subject in need thereof. The desirable properties include: 1) the ability of the inventive compound to complex with and "protect" the agent that may otherwise be labile; 2) the ability of the inventive compound to buffer the pH in an endosome of a cell of the subject; 3) the ability of the inventive compound to act as a "proton sponge" and cause endosomolysis; and 4) the ability of the inventive compound to substantially neutralize the negative charges of the agent.

A compound of the invention and an agent may form a complex in a composition of the invention. For example, a compound of the invention comprises secondary or tertiary amino moieties, which may be useful in enhancing the ability of an inventive composition including an agent (such as a polynucleotide) to deliver the agent to a subject (e.g., into a cell of the subject) in need thereof. The amino moieties, sterically hindered or not, may non-covalently interact with a polynucleotide. A polynucleotide may be contacted with a compound of the invention under conditions suitable to form a complex. In certain embodiments, the polynucleotide binds to a compound of the invention to form a complex through one or more non-covalent interactions described herein. In certain embodiments, the polynucleotide binds to a compound of the invention to form a complex through electrostatic interactions. Without wishing to be bound by any particular theory, one or more amino moieties of an inventive compound may be positively charged, and the polynucleotide (e.g., the monophosphate, diphosphate, and/or triphosphate moieties of the polynucleotide) may be negatively charged, when a compound of the invention, or a composition thereof, is delivered to a subject in need thereof (e.g., when the compound, or a composition thereof, is delivered to the subject at the physiological pH). The polynucleotide may bind to a compound of the invention to form a complex through electrostatic interactions between the negative charges of the inventive compound and the positive charges of the polynucleotide. By substantially neutralizing the charges (e.g., negative charges) of the polynucleotide, the resulting complex may be able to more easily pass through the hydrophobic membranes (e.g., cytoplasmic, lysosomal, endosomal, nuclear) of a cell, compared to a polynucleotide whose charges are not neutralized. In certain embodiments, the complex is substantially neutral. In certain embodiments, the complex is slightly positively charged. In certain embodiments, the complex has a positive $\zeta$-potential. In certain embodiments the $\zeta$-potential is between 0 and +30.

The compounds of the invention include unsubstituted or substituted alkyl moieties on the amino moieties. The alkyl moieties are hydrophobic and may be useful in enhancing the ability of an inventive composition including an agent (such as a polynucleotide) to deliver the agent to a subject (e.g., into a cell of the subject) in need thereof. For example, the hydrophobic alkyl moieties may assist a complex of an inventive compound and a polynucleotide to more easily pass through cell membranes, which are also hydrophobic, compared to a polynucleotide, which is typically hydrophilic.

Polynucleotides may be degraded chemically and/or enzymatically (e.g., by nucleases and nucleotidases). The interaction of a compound of the invention with the polynucleotide is thought to at least partially prevent the degradation of the polynucleotide.

A compound of the invention may be at least partially provided as a salt (e.g., being protonated) so as to form a complex with a negatively charged agent (e.g., a polynucleotide). In certain embodiments, the complex form particles that are useful in the delivery of the agent to a subject. In certain embodiments, more than one inventive compound may be associated with an agent. For example, the complex may include 1-10, 1-100, 1-1,000, 10-1,000, 100-1,000, or 100-10,000 inventive compounds associated with an agent.

The ratio of the amount of a compound of the invention to the amount of an agent (e.g., a polynucleotide) in an inventive composition including the compound and agent (e.g., as a complex) may be adjusted so that the agent may be more efficiently delivered to a subject in need thereof and/or the toxicity of the composition is decreased. In certain embodiments, the ratio of the inventive compound to the agent is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the inventive compound to the agent is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the invention.

The ratio of the amount of the amino moieties of a compound of the invention to the amount of the phosphate moieties of a polynucleotide (i.e., nitrogen:phosphate ratio) in an inventive composition including the compound and polynucleotide (e.g., as a complex) may also be adjusted so that the polynucleotide may be more efficiently delivered to a subject in need thereof and/or the toxicity of the composition is decreased. See, e.g., Incani et al., *Soft Matter* (2010) 6:2124-2138. In certain embodiments, the nitrogen:phosphate ratio is at least about 1:1, at least about 2:1, at least about 5:1, at least about 10:1, at least about 20:1, at least about 50:1, at least about 100:1, at least about 200:1, or at least about 500:1 mol/mol. In certain embodiments, the nitrogen:phosphate ratio is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the invention.

An agent described herein may be covalently or non-covalently (e.g., complexed or encapsulated) attached to a compound of the invention, or included in a composition comprising a compound of the invention. In certain embodiments, upon delivery of the agent into a cell of a subject in need thereof, the agent is able to interfere with the expression of a specific gene in the cell.

Particles

A composition including an inventive compound and an agent may be in the form of a particle. In certain embodiments, the inventive compound is in the form of a particle. In certain embodiments, the agent is in the form of a particle. In certain embodiments, the inventive compound and agent form a complex, and the complex is in the form of a particle. In certain embodiments, the inventive compound encapsulates the agent and is in the form of a particle. In certain embodiments, the inventive compound is mixed with the agent, and the mixture is in the form of a particle.

In certain embodiments, an inventive compound (e.g., a plurality of molecules of the inventive compound) is in the form of a particle. In certain embodiments, a complex of an inventive compound (e.g., a plurality of molecules of the inventive compound) and an agent in a composition of the invention is in the form of a particle. In certain embodiments, the particle is a microparticle. In certain embodiments, the particle is a nanoparticle. Such a nanoparticle may be referred to as a "lipid nanoparticle" (LNP). In certain embodiments, the average diameter of the particle is at least about 10 nm, at least about 30 nm, at least about 100 nm, at least about 300 nm, at least about 1 µm, at least about 3 µm, at least about 10 µm, at least about 30 µm, at least about 100 µm, at least about 300 µm, or at least about 1 mm.

In certain embodiments, the average diameter of the particle is less than about 1 mm, less than about 300 µm, less than about 100 µm, less than about 30 µm less than about 10 µm, less than about 3 µm, less than about 1 µm, less than about 300 nm, less than about 100 nm, less than about 30 nm, or less than about 10 nm. Combinations of the above ranges (e.g., at least about 100 nm and less than about 1 µm) are also within the scope of the present invention.

The particles described herein may include additional materials such as polymers (e.g., synthetic polymers (e.g., PEG, PLGA) and natural polymers (e.g., phospholipids, proteins)). In certain embodiments, the additional materials are approved by a regulatory agency, such as the U.S. FDA, for human and veterinary use.

The particles may be prepared using any method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, polydispersity, etc.). The method of preparing the particle and the conditions (e.g., solvent, temperature, concentration, and air flow rate, etc.) used may also depend on the agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the above methods have a size range outside of the desired range, the particles can be sized, for example, using a sieve. The particles may also be coated. In certain embodiments, the particles are coated with a targeting agent. In certain embodiments, the particles are coated with a surface-altering agent. In some embodiments, the particles are coated to achieve desirable surface properties (e.g., a particular charge).

Micelles, Liposomes, and Lipoplexes

A composition including an inventive compound and an agent may be in the form of a micelle or liposome. In certain embodiments, the inventive compound is in the form of a micelle or liposome. In certain embodiments, the agent is in the form of a micelle or liposome. In certain embodiments, the inventive compound and agent form a complex, and the complex is in the form of a micelle or liposome. In certain embodiments, the inventive compound encapsulates the agent and is in the form of a micelle or liposome. In certain embodiments, the inventive compound is mixed with the agent, and the mixture is in the form of a micelle or liposome. Micelles and liposomes are particularly useful in delivering an agent, such as a hydrophobic agent. When the micelle or liposome is complexed with (e.g., encapsulates or covers) a polynucleotide, the resulting complex may be referred to as a "lipoplex." Many techniques for preparing micelles and liposomes are known in the art, and any such method may be used to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of lipsomes may involve preparing a compound of the invention for hydration, hydrating the compound with agitation, and sizing the vesicles to achieve a homogenous distribution of liposomes. A compound of the invention may be first dissolved in an organic solvent in a container to result in a homogeneous mixture. The organic solvent is then removed to form a polymer-derived film. This polymer-derived film is thoroughly dried to remove residual organic solvent by placing the container on a vacuum pump for a period of time. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm. In certain embodiments, the amount of a compound of the invention in the liposome ranges from about 30 mol % to about 80 mol %, from about 40 mol % to about 70 mol %, or from about 60 mol % to about 70 mol %. In certain embodiments, the inventive compound employed further complexes an agent, such as a polynucleotide. In such embodiments, the application of the liposome is the delivery of the polynucleotide.

The following scientific papers described other methods for preparing liposomes and micelles: Narang et al., "Cationic Lipids with Increased DNA Binding Affinity for Nonviral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Kits

Also encompassed by the invention are kits (e.g., packs). The kits provided may comprise an inventive composition and a container (e.g., a vial, ampule, bottle, syringe, and/or dispenser package, or other suitable container). In some embodiments, provided kits may optionally further include a second container comprising an excipient for dilution or suspension of an inventive composition. In some embodiments, the inventive composition provided in the first container and the inventive composition provided in the second container are combined to form one unit dosage form.

Thus, in one aspect, provided are kits including a first container comprising a composition of the invention. In certain embodiments, the kits described herein are useful for delivering an agent to a subject or cell. In certain embodiments, the kits are useful for delivering an agent to a target tissue of a subject. In certain embodiments, the kits are useful for delivering an agent to the liver of a subject. In certain embodiments, the kits are useful for delivering an agent to the spleen of a subject. In certain embodiments, the kits are useful for delivering an agent to the lung of a subject. In certain embodiments, the kits are useful for selectively delivering an agent to the liver, spleen, and/or lung of a subject. In certain embodiments, the kits described herein are useful for preventing and/or treating a disease described herein. In certain embodiments, the kits are useful for preventing and/or treating a genetic disease. In certain embodiments, the kits are useful for preventing and/or treating a proliferative disease. In certain embodiments, the kits are useful for treating and/or preventing cancer. In certain embodiments, the kits are useful for treating and/or preventing a benign neoplasm. In certain embodiments, the kits are useful for treating and/or preventing pathological angiogenesis. In certain embodiments, the kits are useful for treating and/or preventing an inflammatory disease. In certain embodiments, the kits are useful for treating and/or preventing an autoimmune disease. In certain embodiments, the kits are useful for treating and/or preventing a hematological disease. In certain embodiments, the kits are useful for treating and/or preventing a neurological disease. In certain embodiments, the kits are useful for treating and/or preventing an immunological disease. In certain embodiments, the kits are useful for treating and/or preventing a gastrointestinal disease (e.g., liver disease). In certain embodiments, the kits are useful for treating and/or preventing a respiratory disease (e.g., lung disease). In certain embodiments, the kits are useful for treating and/or preventing a painful condition. In certain embodiments, the kits are useful for treating and/or preventing a psychiatric disorder. In certain embodiments, the kits are useful for treating and/or preventing a metabolic disorder. In certain embodiments, the kits are useful for treating and/or preventing a spleen disease. In certain embodiments, the kits are useful for treating and/or preventing hepatic carcinoma, hypercholesterolemia, refractory anemia, or familial amyloid neuropathy.

In certain embodiments, the kits further include instructions for using (e.g., administering) the composition. The kits may also include information as required by a regulatory agency such as the U.S. Food and Drug Administration (FDA). In certain embodiments, the information included in the kits is prescribing information. In certain embodiments, the kits, including the instructions, provide for treating and/or preventing a disease described herein. In certain embodiments, the kits, including the instructions, provide for preventing and/or treating a genetic disease. In certain embodiments, the kits, including the instructions, provide for preventing and/or treating a proliferative disease. In certain embodiments, the kits, including the instructions, provide for treating and/or preventing cancer. In certain embodiments, the kits, including the instructions, provide for treating and/or preventing a benign neoplasm. In certain embodiments, the kits, including the instructions, provide for treating and/or preventing pathological angiogenesis. In certain embodiments, the kits, including the instructions, provide for treating and/or preventing an inflammatory disease. In certain embodiments, the kits, including the instructions, provide for treating and/or preventing an autoimmune disease. In certain embodiments, the kits, including the instructions, provide for treating and/or preventing a hematological disease. In certain embodiments, the kits, including the instructions, provide for treating and/or preventing a neurological disease. In certain embodiments, the kits, including the instructions, provide for treating and/or preventing an immunological disease. In certain embodiments, the kits, including the instructions, provide for treating and/or preventing a gastrointestinal disease (e.g., liver disease). In certain embodiments, the kits, including the instructions, provide for treating and/or preventing a respiratory disease (e.g., lung disease). In certain embodiments, the kits, including the instructions, provide for treating and/or preventing a painful condition. In certain embodiments, the kits, including the instructions, provide for treating and/or preventing a psychiatric disorder. In certain embodiments, the kits, including the instructions, provide for treating and/or preventing a metabolic disorder. In certain embodiments, the kits, including the instructions, provide for treating and/or preventing a spleen disease. In certain embodiments, the kits, including the instructions, provide for treating and/or preventing hepatic carcinoma, hypercholesterolemia, refractory anemia, or familial amyloid neuropathy. The kit of the invention may include one or more agents described herein as a separate composition.

Methods of Preparing the Compounds

The present invention also provides methods of preparing the compounds of the invention. In one aspect, provided are methods of preparing the compounds of Formula (I), and salts and stereoisomers thereof, the methods including:

(a) reacting a compound of Formula (A), or a salt thereof, with a compound of Formula (B), or a salt thereof, to provide a compound of Formula (C), or a salt thereof:

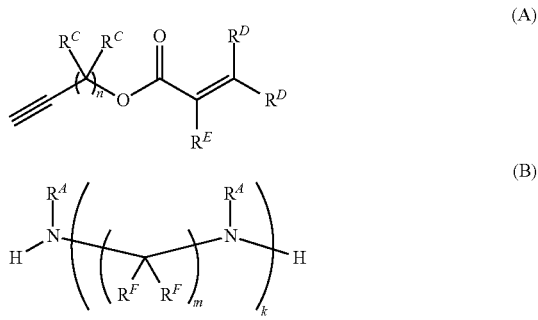

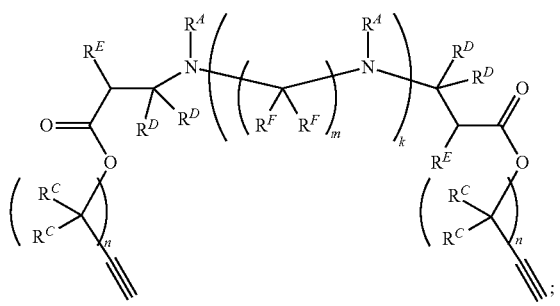

and (b) reacting the compound of Formula (C), or a salt thereof, with a compound of Formula (D), or a salt thereof, to provide the compound of claim 1, or the salt or stereoisomer thereof:

$R^B$—SH (D), wherein $R^A$, $R^B$, $R^C$, $R^D$, $R^E$, $R^F$, k, m, and n are as described herein.

The step(s) of the methods of preparing the compounds of the invention may be performed under any suitable conditions. A suitable condition is a combination of physical and chemical parameters under which an intended product (e.g., a compound of Formula (I), or a salt or stereoisomer thereof) or intermediate may be formed using the inventive methods. A suitable condition may include the absence of a solvent (i.e., neat). A suitable condition may include a suitable solvent. In certain embodiments, the suitable solvent is an organic solvent. In certain embodiments, the suitable solvent is an alkyl alcohol (e.g., methanol, ethanol, propanol, and butanol). In certain embodiments, the suitable solvent is ethanol. In certain embodiments, the suitable solvent is acetone, acetonitrile (ACN), N,N-dimethylformamide (DMF), N,N-dimethylacetamide (DMA), dimethysulfoxide (DMSO), ethyl acetate (EtOAc), N-methyl-2-pyrrolidone (NMP), 2-pyrrolidone, tetrahydrofuran (THF), benzene, toluene, xylene, or a mixture thereof. In certain embodiments, the suitable solvent is an inorganic solvent. In certain embodiments, the suitable solvent is water.

Compounds of any one of Formulae (A)-(D), or salts thereof, or a mixture thereof, may be present in a suitable solvent described herein at a suitable concentration. In certain embodiments, the suitable concentration is at least about 10 M, at least about 100 μM, at least about 1 mM, at least about 10 mM, at least about 100 mM, at least about 1 M, or at least about 10 M, as solubility permits. In certain embodiments, the suitable concentration is lower than about 10 M, lower than about 1 M, lower than about 100 mM, lower than about 10 mM, lower than about 1 mM, lower than about 100 μM, or lower than about 10 μM, as the solubility permits. Combinations of the above-referenced ranges (e.g., at least about 1 mM and lower than about 1 M) are also within the scope of the invention.

A suitable condition may include a suitable ratio (e.g., mole ratio) of the amount of a compound of a compound of Formula (A), or a salt thereof, to the amount of a compound of Formula (B), or a salt thereof. A suitable condition may also include a suitable ratio of the amount of a compound of Formula (D), or a salt thereof, to the amount of a compound of Formula (C), or a salt thereof. In certain embodiments, the suitable ratio described herein is at least about 1:1, at least about 2:1, at least about 2.5:1, at least about 6:1, at least about 10:1, at least about 20:1, at least about 50:1, at least about 100:1, at least about 300:1, or at least about 1,000:1 mol/mol. In certain embodiments, the suitable ratio is at most about 1,000:1, at most about 300:1, at most about 100:1, at most about 50:1, at most about 20:1, at most about 10:1, at most about 6:1, at most about 2.5:1, at most about 2:1, or at most about 1:1 mol/mol. Combinations of the above-referenced ranges (e.g., at least about 2:1 and at most about 20:1 mol/mol) are also within the scope of the invention. In certain embodiments, the suitable ratio is about 2.5:1 mol/mol. In certain embodiments, the suitable ratio is about 5.6:1 mol/mol.

A suitable condition may also include a suitable temperature under which a step of a method of preparing the compounds of the invention is performed. In certain embodiments, the suitable temperature is at least about 20° C., at least about 23° C., at least about 25° C., at least about 45° C., at least about 60° C., at least about 80° C., at least about 100° C., or at least about 120° C. In certain embodiments, the suitable temperature is lower than about 120° C., lower than about 100° C., lower than about 80° C., lower than about 60° C., lower than about 45° C., lower than about 25° C., lower than about 23° C., or lower than about 20° C. Combinations of the above-referenced ranges (e.g., at least about 25° C. and lower than about 60° C.) are also within the scope of the invention. In certain embodiments, the suitable temperature is ambient temperature (e.g., about 20° C., about 23° C., or about 25° C.). In certain embodiments, the suitable temperature is about 45° C. A suitable temperature may be a variable temperature during a step of a method of preparing the compounds of the invention.

A suitable condition may also include a suitable pressure under which a step of a method of preparing the compounds of the invention is performed. In certain embodiments, the suitable pressure is at least about 1 atmosphere, at least about 2 atmospheres, at least about 5 atmospheres, at least about 10 atmospheres, at least about 20 atmospheres, or at least about 50 atmospheres. In certain embodiments, the suitable pressure is lower than about 50 atmospheres, lower than about 20 atmospheres, lower than about 10 atmospheres, lower than about 5 atmospheres, lower than about 2 atmospheres, or lower than 1 about atmosphere. Combinations of the above-referenced ranges (e.g., at least about 1 atmosphere and lower than about 10 atmospheres) are also within the scope of the invention. In certain embodiments, the suitable pressure is about 1 atmosphere.

A suitable condition may also include a suitable atmosphere under which a step of a method of preparing the compounds of the invention is performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that a step of a method of preparing the compounds of the invention lasts. In certain embodiments, the suitable time duration is in the order of minutes (e.g., about 1, about 3, about 10, or about 30 minutes), hours (e.g., about 1, about 2, about 4, about 6, about 12, or about 18 hours), or days (e.g., about 1 day). In certain embodiments, the suitable time duration is about 3 minutes. In certain embodiments, the suitable time duration is about 12 hours.

A condition may also include irradiation with ultraviolet (UV) light. In certain embodiments, the intensity of the UV irradiation is at least about 0.1, at least about 0.3, at least about 1, at least about 3, at least about 10, at least about 30, at least about 100, at least about 300, or at least about 1,000 mW/cm$^2$. In certain embodiments, the intensity of the UV irradiation is at most about 1,000, at most about 300, at most about 100, at most about 30, at most about 10, at most about 3, at most about 1, at most about 0.3, or at most about 0.1 mW/cm$^2$. Combinations of the above-referenced ranges (e.g., at least about 1 and at most about 100 mW/cm$^2$) are also within the scope of the invention. In certain embodiments, the intensity of the UV irradiation is about 10 mW/cm$^2$. In certain embodiments, the wavelength of the UV irradiation is at least about 100, at least about 150, at least about 200, at least about 250, at least about 280, at least about 300, at least about 350 at least about 400, at least about 450, or at least about 500 nm. In certain embodiments, the wavelength of the UV irradiation is at most about 500, at most about 450, at most about 400, at most about 350, at most about 300, at most about 280, at most about 250, at most about 200, at most about 150, or at most about 100 nm. Combinations of the above-referenced ranges (e.g., at least about 280 and at most about 450 nm) are also within the scope of the invention. Ranges of wavelengths (e.g., from about 280 to about 450 nm) are also within the scope of the invention. In certain embodiments, the wavelength of the UV irradiation is from about 280 to about 450 nm.

A suitable condition may also include presence of a catalyst. In certain embodiments, the catalyst is a photoinitiator (e.g., a compound capable of generating free radicals and catalyzing a photochemical reaction). In certain embodiments, the catalyst is an acetophenone photoinitiator (e.g., 2,2-dimethoxy-2-phenylacetophenone (DMPA)), a benzil or benzoin photoinitiator (e.g., 4,4'-dimethylbenzil or benzoin), a benzophenone photoinitiator (e.g., benzophenone), a cationic photoinitiator (e.g., diphenyliodonium nitrate), a thioxanthone photoinitiator (e.g., thioxanthen-9-one), azobisisobutyronitrile (AIBN), benzoyl peroxide (BPO), anthraquinone-2-sulfonic acid sodium salt monohydrate, 2-tert-butylanthraquinone, camphorquinone, diphenyl(2,4,6-trimethylbenzoyl)phosphine oxide, 9,10-phenanthrenequinone, or phenylbis(2,4,6-trimethylbenzoyl)phosphine oxide. In certain embodiments, the catalyst is DMPA.

A suitable condition may also include irradiation with microwave, such as what is described in Majetich et al., *J. Microwave Rower and Electromagnetic Energy* 1995, 30, 27-45. A suitable condition may further include agitating (e.g., stirring and/or shaking).

One or more intermediates resulting from a step of a method of preparing the compounds of the invention may be isolated and/or purified, and the isolated and/or purified intermediates may be reacted in a next step of the method. The isolated and/or purified intermediates may be substantially free of impurities or may contain one or more other components, such as reagents and solvents employed in the step yielding the intermediates, and byproducts. The one or more intermediates may also be reacted in a next step without being isolated and/or purified. The intermediates and/or intended products of the methods of preparing the compounds of the invention may be isolated and/or purified using methods known in the art, such as chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying. In certain embodiments, the intended products described herein are substantially free of impurities.

Methods of Treatment and Uses

It is estimated that over 10,000 human diseases are caused by genetic disorders, which are abnormalities in genes or chromosomes. See, e.g., McClellan, J. and M. C. King, *Genetic heterogeneity in human disease.* Cell. 141 (2): p. 210-7; Leachman, S. A., et al., *J. Dermatol. Sci.,* 2008. 51 (3): p. 151-7. Many of these diseases are fatal, such as cancer, severe hypercholesterolemia, and familial amyloidotic polyneuropathy. See, e.g., Frank-Kamenetsky, M., et al., *Proc. Natl. Acad. Sci. U.S.A.* 2008. 105 (33): p. 11915-20; Coelho, T., *Curr. Opin. Neurol.,* 1996. 9 (5): p. 355-9. Since the discovery of gene expression silencing via RNA interference (RNAi) by Fire and Mello (Fire, A., et al., *Nature,* 1998. 391 (6669): p. 806-11), there has been extensive effort toward developing therapeutic applications for RNAi in humans. See, e.g., Davis, M. E., *Mol. Pharm.* 2009. 6 (3): p. 659-68; Whitehead, K. A., R. Langer, and D. G. Anderson, *Nat. Rev. Drug Discovery,* 2009. 8 (2): p. 129-138; Tan, S. J., et al., *Small.* 7 (7): p. 841-56; Castanotto, D. and J. J. Rossi, *Nature,* 2009. 457 (7228): p. 426-33; Chen, Y. and L. Huang, *Expert Opin. Drug Deliv.* 2008. 5 (12): p. 1301-11; Weinstein, S. and D. Peer, *Nanotechnology.* 21 (23): p. 232001; Fenske, D. B. and P. R. Cullis, *Expert Opin. Drug Deliv.* 2008. 5 (1): p. 25-44; and Thiel, K. W. and P. H. Giangrande, *Oligonucleotides,* 2009. 19 (3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Biotechnol. J.* 6 (9): p. 1130-46. However, the efficient and safe delivery of siRNA is still a key challenge in the development of siRNA therapeutics. See, e.g., Juliano, R., et al., *Mol. Pharm.* 2009. 6 (3): p. 686-95.

In one aspect, the present invention provides methods of delivering an agent described herein to a subject in need thereof or a cell. In certain embodiments, provided are methods of delivering the agent to a target tissue to the subject. In certain embodiments, provided are methods of delivering the agent to the liver of the subject. In certain embodiments, provided are methods of delivering the agent to the spleen of the subject. In certain embodiments, provided are methods of delivering the agent to the lung of the subject. In certain embodiments, provided are methods of selectively delivering the agent to the liver, spleen, and/or lung of the subject. In certain embodiments, provided are methods of delivering a polynucleotide to the subject or cell. In certain embodiments, provided are methods of delivering a DNA to the subject or cell. In certain embodiments, provided are methods of delivering a pDNA to the subject or cell. In certain embodiments, provided are methods of delivering an RNA to the subject or cell. In certain embodiments, provided are methods of delivering an siRNA to the subject or cell. In certain embodiments, provided are methods of delivering an mRNA to the subject or cell. In certain embodiments, the agent is delivered into a cell of the subject.

Another aspect of the invention relates to methods of increasing the delivery of an agent (e.g., a pharmaceutical agent) to a subject or cell. In certain embodiments, the delivery of the agent to the subject or cell is increased. In certain embodiments, the delivery of the agent to the subject or cell by an inventive composition that includes the agent and an inventive compound is increased compared to the delivery of the agent to the subject or cell by a composition that includes the agent but does not include the inventive compound.

In another aspect, the present invention provides methods of treating and/or preventing a disease. In certain embodiments, the present invention provides methods of treating a disease. In certain embodiments, the present invention provides methods of preventing a disease. In certain embodiments, the disease being treated and/or prevented is a disease described herein. In certain embodiments, the disease is treated and/or prevented by the inventive methods. In certain embodiments, the disease is treated by the inventive methods. In certain embodiments, a symptom of the disease is reduced or eliminated by the inventive methods. In certain embodiments, the progression of the disease is slowed by the inventive methods. In certain embodiments, the disease is prevented by the inventive methods. In certain embodiments, the onset of the disease is prevented by the inventive methods. In certain embodiments, the regression of the disease is prevented by the inventive methods.

In another aspect, the present invention provides methods of reducing the risk of having a disease in a subject in need thereof. In certain embodiments, the risk of having the disease is reduced by the inventive methods.

In certain embodiments, the disease described herein is a genetic disease. In certain embodiments, the genetic disease is a genetic disease described herein. In certain embodiments, the disease described herein is cancer. In certain embodiments, the cancer is a cancer described herein. In certain embodiments, the disease described herein is a benign neoplasm. In certain embodiments, the benign neoplasm is a benign neoplasm described herein. In certain embodiments, the disease described herein is pathological angiogenesis. In certain embodiments, the pathological angiogenesis is pathological angiogenesis described herein. In certain embodiments, the disease described herein is an inflammatory disease. In certain embodiments, the inflammatory disease is an inflammatory disease described herein. In certain embodiments, the disease described herein is an autoimmune disease. In certain embodiments, the autoimmune disease is an autoimmune disease described herein. In certain embodiments, the disease described herein is a hematological disease. In certain embodiments, the hematological disease is a hematological disease described herein. In certain embodiments, the disease described herein is a neurological disease. In certain embodiments, the neurological disease is a neurological disease described herein. In certain embodiments, the disease described herein is an immunological disease. In certain embodiments, the disease described herein is a gastrointestinal disease (e.g., liver disease). In certain embodiments, the disease described herein is a respiratory disease (e.g., lung disease). In certain embodiments, the disease described herein is a psychiatric disorder. In certain embodiments, the disease described herein is a metabolic disorder. In certain embodiments, the disease described herein is a spleen disease. In certain embodiments, the disease described herein is a painful condition. In certain embodiments, the painful condition is inflammatory pain. In certain embodiments, the painful condition (e.g., inflammatory pain) is associated with an inflammatory disorder and/or an autoimmune disorder. In certain embodiments, the disease described herein is hepatic carcinoma. In certain embodiments, the disease described herein is hypercholesterolemia. In certain embodiments, the disease described herein is refractory anemia. In certain embodiments, the disease described herein is familial amyloid neuropathy.

Another aspect of the invention relates to methods of genetically engineer a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites). In certain embodiments, the subject is genetically engineered to increase the subject's ability to grow under unfavorable conditions (such as unfavorable weather conditions, e.g., dryness, infertility, and/or extremely cold or extremely high temperature).

In certain embodiments, the methods of the invention comprise administering to the subject a composition of the invention. In certain embodiments, the methods of the invention comprise administering to the subject an effective amount of a composition of the invention. In certain embodiments, the methods of the invention comprise administering to the subject a therapeutically effective amount of a pharmaceutical composition of the invention. In certain embodiments, the methods of the invention comprise contacting the cell with a composition of the invention. In certain embodiments, the methods of the invention comprise contacting the cell with an effective amount of a composition of the invention. In certain embodiments, the methods of the invention comprise contacting the cell with a therapeutically effective amount of a pharmaceutical composition of the invention.

In certain embodiments, the subject described herein is a human. In certain embodiments, the subject is an animal. In certain embodiments, the subject is a non-human animal. The animal may be of either sex and may be at any stage of development. In certain embodiments, the subject is a fish. In certain embodiments, the subject is a mammal. In certain embodiments, the subject is a non-human mammal. In certain embodiments, the subject is a human or non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a plant described herein. In certain embodiments, the subject is a human having a disease described herein (e.g., a proliferative disease). In certain embodiments, the subject is a human suspected of having a disease described herein (e.g., a proliferative disease). In certain embodiments, the subject is a human at risk of having a disease described herein (e.g., a proliferative disease).

In certain embodiments, the cell described herein is in vivo. In certain embodiments, the cell is in vitro. In certain embodiments, the cell is ex vivo.

In certain embodiments, the inventive methods are in vivo methods. In certain embodiments, the inventive methods are in vitro methods. In certain embodiments, the inventive methods are ex vivo methods.

Another aspect of the invention relates to methods of screening a library of compounds to identify a compound that is useful in the methods of the invention. In certain embodiments, the methods of screening a library of compounds are useful in identifying a compound with desired or undesired properties. In certain embodiments, the desired property is solubility in water, solubility at different pH, ability to bind polynucleotides, ability to bind heparin, ability to bind small molecules, ability to bind protein, ability to form microparticles, ability to increase transfection efficiency, ability to support normal cell growth, ability to inhibit abnormal cell growth, ability to support cell attachment, ability to support tissue growth, and/or intracellular delivery of an agent described herein and/or an agent complexed or attached thereto to aid in bioprocessing. In certain embodiments, the undesired property is the lack of a desired property. In certain embodiments, the compound identified is useful for treating and/or preventing a disease described herein. In certain embodiments, the library of compounds is a library of compounds of the invention. In certain embodiments, the methods of screening a library include providing at least two different compounds of the invention; and performing at least one assay using the different compounds of the invention. In certain embodiments, at least one assay is useful in identifying a compound that is useful in the inventive methods. The assay may be an immunoassay, such as a sandwich-type assay, competitive binding assay, one-step direct test, two-step test, or blot assay. The step of performing at least one assay may be performed robotically or manually.

In another aspect, the present invention provides the compounds and compositions of the invention for use in the treatment and/or prevention of a disease described herein in a subject in need thereof. In certain embodiments, the present invention provides the compounds and compositions of the invention for use in the treatment of a disease described herein in a subject in need thereof.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds

Recent high-throughput screens of lipid-like compounds indicate that structures with multiple short alkyl tails stemming from a polyamine core are able to facilitate efficient gene silencing (3, 16, 17). To synthesize pure multi-tailed compounds with varying polyamine head group architectures, a rapid and efficient two-step solvent free synthetic route was developed that requires neither protection/deprotection steps nor the use of costly and time-consuming chromatographic purification (see, e.g., Schemes 1 and 2). The first step involves a quantitative Michael addition between a primary amine 2 or secondary diamine 5 and propargyl acrylate 1. The resulting bis-alkyne modified amines 3 and 6 are subjected to a thiol-yne "click" photoaddition with decanethiol 4 in the presence of a catalyst (e.g., a photocatalyst, such as a photoinitiator). The thiol-yne reaction is rapid and efficient and yields pure four-tailed lipid products in only about 180 seconds after methanol precipitation. This approach generates a chemically pure library of lipids bearing the same number and position of lipid tails with differing head group architectures. Using this two-step synthetic route, the entire purified lipid library can be generated from start to finish in parallel in less than 2 days.

Compounds of the invention (e.g., compounds of Formula (I-B-4) or (I-C-4), and salts and stereoisomers thereof) may be prepared by methods shown in Schemes 1 and 2. Alternatively, the compounds of the invention may be prepared by other methods described herein or known in the art. All chemical reagents (amines for the preparation of compounds I-1 to I-32, propargyl acrylate, 1-decanethiol, cholesterol, 2-(p-toluidino)-6-napthalene sulfonic acid, 1,2-distearoyl-sn-glycero-3-phosphocholine, and 2,2-dimethoxy-2-phenylacetophenone) were purchased from commercial sources and used without further purification. In one set of experiments, compound 2 (1 equivalent) was reacted with about 2.5 equivalents of compound 1 (neat) at about 45° C. overnight. Excess amount of compound 1 was removed via a centrifuge evaporator (Genavac). The resulting residue was substantially pure compound 3 (confirmed via $^1$H-NMR and LCMS). Compound 3 was mixed with about 5.6 equivalents of compound 4 and about 4 wt % of 2,2-dimethoxy-2-phenylacetophenone (DMPA), and the resulting mixture was irradiated with UV light at about 10 mW/cm$^2$ for about 180 seconds. The desired product (e.g., a compound of Formula (I-B-4) was precipitated out of the liquid phase with methanol and dried with a centrifuge evaporator.

Scheme 1. Exemplary synthesis of compounds of Formula (I).

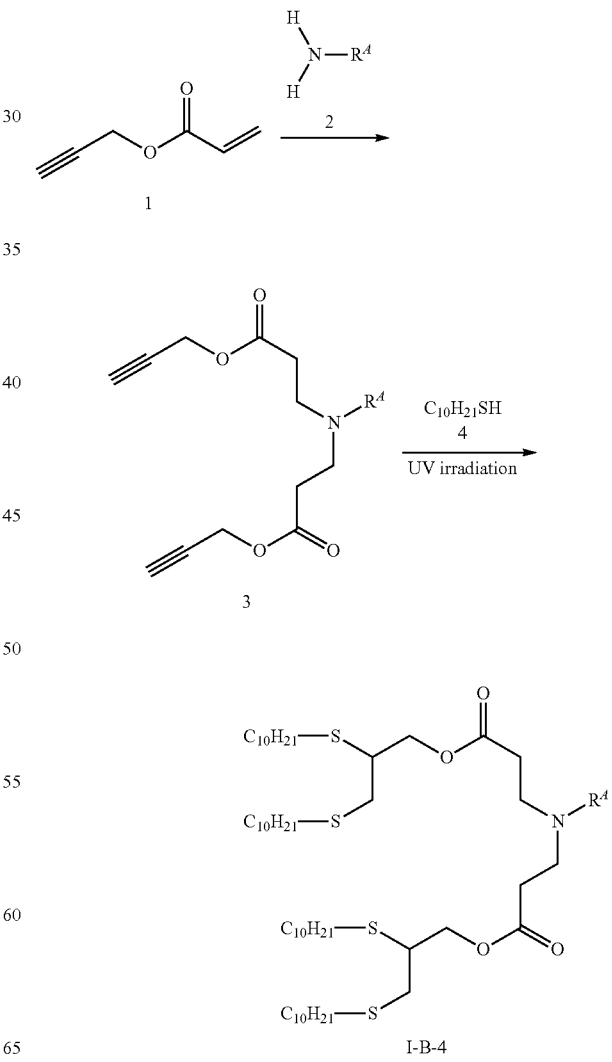

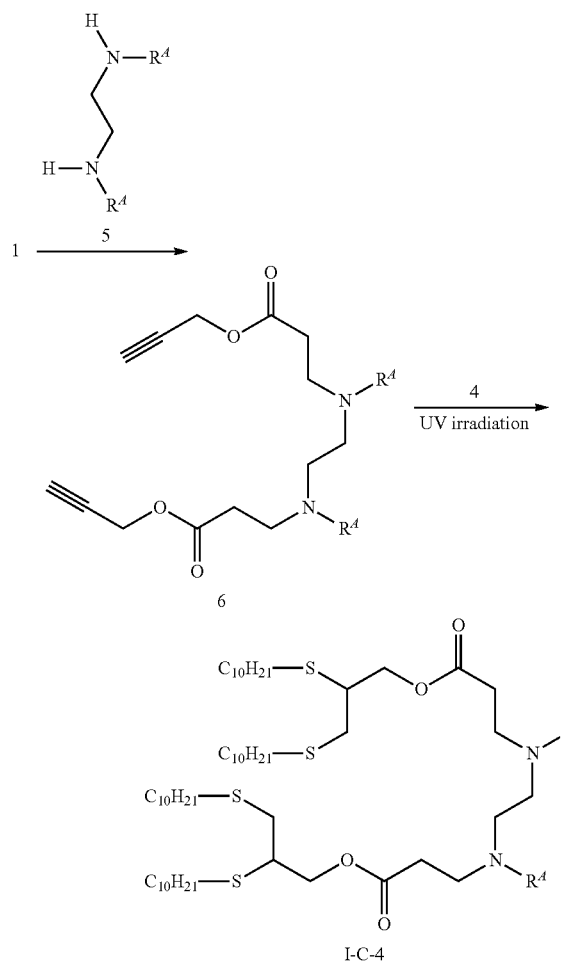

Scheme 2. Exemplary synthesis of compounds of Formula (I).

The high-resolution mass spectra (HRMS) of exemplary compounds of Formula (I) were determined using LCMS (Waters® Xevo QTof MS paired with an ACQUITY UPLC system). The results are shown in Table 1.

TABLE 1

LCMS data of exemplary compounds of Formula (I).

| Compound # | Molecular Formula | Calculated [M + 1] | Found [M + 1] |
|---|---|---|---|
| I-1  | $C_{57}H_{114}N_2O_4S_4$ | 1019.8 | 1019.8 |
| I-2  | $C_{59}H_{118}N_2O_4S_4$ | 1047.8 | 1047.8 |
| I-3  | $C_{56}H_{112}N_2O_4S_4$ | 1005.8 | 1005.8 |
| I-4  | $C_{60}H_{120}N_2O_4S_4$ | 1061.8 | 1061.9 |
| I-5  | $C_{59}H_{118}N_2O_4S_4$ | 1047.8 | 1047.8 |
| I-6  | $C_{63}H_{126}N_2O_4S_4$ | 1103.9 | 1103.9 |
| I-7  | $C_{59}H_{116}N_2O_4S_4$ | 1045.8 | 1045.8 |
| I-8  | $C_{58}H_{114}N_2O_5S_4$ | 1047.8 | 1047.8 |
| I-9  | $C_{58}H_{114}N_2O_4S_4$ | 1031.8 | 1031.8 |
| I-10 | $C_{56}H_{110}N_2O_4S_4$ | 1003.7 | 1003.8 |
| I-11 | $C_{57}H_{112}N_2O_4S_4$ | 1017.8 | 1017.8 |
| I-12 | $C_{59}H_{116}N_2O_4S_4$ | 1045.8 | 1045.8 |
| I-13 | $C_{59}H_{110}N_2O_4S_4$ | 1039.7 | 1039.8 |
| I-14 | $C_{59}H_{116}N_2O_4S_4$ | 1045.8 | 1045.8 |
| I-15 | $C_{59}H_{116}N_2O_4S_4$ | 1045.8 | 1045.8 |
| I-16 | $C_{59}H_{116}N_2O_4S_4$ | 1045.8 | 1045.8 |
| I-17 | $C_{59}H_{116}N_2O_4S_4$ | 1045.8 | 1045.8 |
| I-18 | $C_{59}H_{115}NO_4S_4$ | 1030.8 | 1030.8 |
| I-19 | $C_{61}H_{120}N_2O_4S_4$ | 1073.8 | 1073.9 |
| I-20 | $C_{58}H_{111}N_3O_4S_4$ | 1042.7 | 1042.8 |

TABLE 1-continued

LCMS data of exemplary compounds of Formula (I).

| Compound # | Molecular Formula | Calculated [M + 1] | Found [M + 1] |
|---|---|---|---|
| I-21 | $C_{61}H_{121}N_3O_4S_4$ | 1088.8 | 1088.9 |
| I-22 | $C_{60}H_{119}N_3O_4S_4$ | 1074.8 | 1074.9 |
| I-23 | $C_{59}H_{117}N_3O_4S_4$ | 1060.8 | 1060.8 |
| I-24 | $C_{60}H_{119}N_3O_4S_4$ | 1074.8 | 1074.8 |
| I-25 | $C_{59}H_{117}N_3O_4S_4$ | 1060.8 | 1060.8 |
| I-26 | $C_{56}H_{111}NO_4S_4$ | 990.7 | 990.8 |
| I-27 | $C_{58}H_{114}N_2O_4S_4$ | 1031.8 | 1031.8 |
| I-28 | $C_{58}H_{114}N_2O_6S_5$ | 1095.7 | 1095.8 |
| I-29 | $C_{64}H_{118}N_2O_4S_4$ | 1107.8 | 1107.8 |
| I-30 | $C_{63}H_{116}N_2O_4S_4$ | 1093.8 | 1093.8 |
| I-31 | $C_{57}H_{114}N_2O_4S_4$ | 1019.8 | 1019.8 |
| I-32 | $C_{56}H_{112}N_2O_4S_4$ | 1005.8 | 1005.8 |

Example 2. Biological Assays

General Methods

What is described herein is a systematic evaluation of multiple parameters associated with both the physicochemical properties and biological barriers to delivery for a group of lipid nanoparticles (LNPs). The approach involves mapping out the entire delivery pathway and evaluating the correlation between each property or delivery barrier and gene silencing (FIG. 1, steps 1-6). This systematic approach presents two potential advantages. First, the correlation of multiple physicochemical properties and biological barriers for a large set of LNPs with gene silencing allows for identification of relevant relationships between structure, biological function, and biological activity. Understanding these relationships will help improve the design of future therapeutic delivery vehicles. Second, a multi-parametric evaluation with LNPs may lead to the identification of parameters that can complement in vitro gene knockdown as a pre-screening tool for the selection of LNPs for in vivo use.

To obtain accurate correlations and accelerate both synthesis and evaluation, novel lipids (e.g., compounds of Formula (I), and salts and stereoisomers thereof) were synthesized that can be formulated with siRNAs to produce LNPs. LNPs were employed in this study because they have been shown to facilitate efficient delivery to hepatic and immune targets (17-23). In the past few years, LNPs formulated with siRNAs against TTR and PCSK9 in rodents and non-human primates have produced promising preclinical results and several clinical trials involving LNPs are currently underway (21-24). Recently, clinical trials involving administration of a single dose of LNPs with siRNAs against TTR (ALN-TTR02) have shown robust knockdown of serum TTR protein levels of up to 94% (24, 25). In addition to systemic delivery to hepatic and immune targets, LNPs have also found use in the development of improved cellular vaccine therapies for cancer treatment. LNPs formulated with siRNAs against programmed death ligands (PD-L1 and PD-L2) were recently shown to significantly boost the immunogenicity of dendritic cell-based vaccines following ex vivo treatment (25, 26). To evaluate the potential barriers to LNP mediated siRNA delivery, the following parameters were measured: 1) cellular uptake; 2) endosomal escape capability; 3) extracellular; and 4) intracellular LNP disassembly (via FRET-labeled molecular siRNA probes) (16, 17, 26). All assays were adapted to a 96-well plate format, allowing for rapid throughput. Physicochemical properties of the LNPs such as size, siRNA entrapment, and $pK_a$ were correlated with both biological barriers and gene silencing activity.

Lipid Nanoparticle (LNP) Formulation for In Vitro and In Vivo Gene Silencing Studies siRNA duplexes labeled at the 5' end of the sense strand with either Alexa Fluor® 594 or Alexa Fluor® 647 dyes were purchased from Integrated DNA Technologies (HPLC purified and desalted). The sequences are:

```
(sense)
5'-Alex594-GAUUAUGUCCGGUUAUGUAUU-3'

5'-Alex647-GAUUAUGUCCGGUUAUGUAUU-3'

(antisense)
5'-UACAUAACCGGACAUAAUCUU-3'

Sequence against firefly luciferase:
(sense)
5'-AAcGcuGGGcGuuAAucAAT*T(C18-OPSS)-3'

(antisense)
5'-UUGAUuAACGCCcAGCGUUT*T-3'

Sequence against FVII:
(sense)
5'-GGAucAucucAAGucuuAcT*T-3'

(antisense)
5'-GuAAGAcuuGAGAuGAuccT*T-3'
```

Note: 2'-methoxy modified nucleotides are in lowercase and phosphorothioate linkages are represented by asterisks. C18-OPSS represents pyridyl disulfide with an 18-carbon chain linker.

Sequences against firefly luciferase and FVII, dual HeLa cells expressing firefly and Renilla luciferase and mPEG2000-DMG were obtained from Alnylam Pharmaceuticals. Phenol red-free DMEM, fetal bovine serum (FBS) and 0.25% trypsin-EDTA were obtained from Invitrogen.

Lipid nanoparticles were formulated by mixing an equal volume of an ethanolic solution of a lipid of the invention (e.g., a compound of the invention) and an ethanolic solution of an siRNA in 10 mM Citrate buffer at pH 3 to give a 5:1 synthesized lipid:siRNA ratio. The resulting solution was then diluted in an equal volume of 1× phosphate-buffered saline (PBS). The ethanolic lipid solution contained a mixture of synthesized lipids, cholesterol (Sigma Aldrich), 1,2-distearoyl-sn-glycero-3-phosphocholine (DSPC, Avanti Polar Lipids, Alabaster, Ala.) and mPEG2000-DMG (MW 2660, Alnylam Pharmaceuticals, Cambridge, Mass.) at a molar ratio of 50:38.5:10:1.5 in 200-proof ethanol. For all studies, the ethanolic lipid and siRNA solutions were hand mixed via pipette. The LNPs for in vivo use were also dialyzed for 75 minutes against 1×PBS in 3500 MW cut-off (MWCO) cassettes (Pierce/Thermo Scientific, Rockford, Ill.) prior to use.

In Vitro Transfection

In vitro transfection was performed on HeLa cells stably modified to constitutively express both firefly and Renilla luciferases. Cells were maintained at 37° C. in a 5% $CO_2$ atmosphere in high glucose Dulbelco modified Eagles medium without phenol red (Invitrogen, Carlsbad, Calif.) supplemented with 10% fetal bovine serum (FBS, Invitrogen). Prior to transfection, 15,000 cells were seeded in white 96-well plates and allowed to attach overnight. On the day of transfection, the media was replaced with 90 μL of fresh media. LNPs were formulated at a concentration of 10 ng/μL and diluted with 1×PBS to obtain the desired concentration. For example, to achieve a transfection of 25 ng of siRNA per well, the 10 ng/μL stock was diluted 1:4 to give 2.5 ng/μL, and 10 μL of this solution was added to the cells in 90 μL of media. Lipofectamine (RNAiMAX) was used according to the manufacturer's instructions as a positive control. Relative firefly luciferase silencing was assessed approximately 24 hours after LNP addition using a Dual-Glo luciferase assay kit (Promega, Madison, Wis.). The firefly luciferase values were normalized to the Renilla luciferase values in order to correct for potential toxicity and/or off-target effects. All experiments were carried out in sextuplicates.

In Vivo Factor VII (FVII) Gene Silencing

All animal experiments were conducted using institutionally approved protocols. C57BL/6 mice (Charles River Laboratories, Wilmington, Mass.) were warmed under a heat lamp and weighed before receiving tail vein injections of either PBS (negative control) or LNPs containing siRNA against FVII at a dose of 1 mg/kg total siRNA. Two days post-injection, the mice were anesthetized via isoflurane inhalation, and about 200 μL of blood was collected retroorbitally into Microtainer™ tubes (BD Biosciences, Franklin Lakes, N.J.). Blood was centrifuged at 4000×g for 10 min, and the supernatant was analyzed for FVII using a Biophen FVII assay kit (Aniara Corporation, Mason, Ohio).

Extracellular/Intracellular Fluorescence Resonance Energy Transfer (FRET) Assays and Cellular Uptake LNPs containing an equimolar mixture of siRNAs labeled with Alexa Fluor® 594 and Alexa Fluor® 647 were diluted to 10 ng siRNA/μL with 1×PBS and added to a black 96-well plate pre-plated with 20,000 HeLa cells at 37° C. Control wells contained LNPs with 1% Triton-X. To measure the FRET, the samples were excited at 540 nm, and the fluorescence intensity was read at 690 and 620 nm using a Tecan Safire 2 Microplate reader at 37° C. FRET was determined as the ratio of the fluorescence intensities at 690/620 nm. FRET signals for all LNPs were normalized to that of the control wells. For extracellular FRET experiments, an identical experiment was carried out without cells, and the FRET data obtained were similar. For intracellular FRET studies, the media were aspirated, and the cells were washed with calcium and magnesium free 1×PBS and trypsinized with 30 μL of 0.25% trypsin-EDTA. The trypsined cells were then neutralized with 120 μL of quenching media (25% cell culture media in 1×PBS) and transferred to a 96-well v-bottom plate and analyzed via flow cytometry. For each sample, 10,000 events were monitored and evaluated by a BD LSR II HTS flow cytometer (BD Bioscience). Samples were excited with a 561 nm excitation laser, and their emission was observed with a 695/40 nm emission filter set. The emission signal obtained was normalized to the emission signal obtained from the Alexa Fluor® 647 channel to normalize for the total LNP uptake at each time point. In addition, each channel was compensated for bleed through using single fluorophore controls. For cell uptake studies, LNPs formulated with just Alexa Fluor® 647 were analyzed using settings for the Alexa Fluor® 647 channel: exciation via a 633 nm (red, HeNe) laser and emission via a 660/20 nm filter.

Hemolysis Assay

Human red blood cells (RBCs, Innovative Research) were washed twice with 1×PBS and diluted in either 1×PBS or citrate buffer saline at pH 5.5 (CBS, 20 mM citrate buffer, 130 mM NaCl) to a 4% v/v RBC solution. In a v-bottom, 96-well plate, 100 μL of blank LNPs formulated at an equivalent concentration of 23.75 ng siRNA/μL (no siRNA was used) were added to 100 μL of the 4% v/v RBC solution in either PBS or CBS and heated to 37° C. for one hour. After cooling, the plate was centrifuged at 4° C. at 1000×g for 5 minutes. 100 µL of the supernatant was transferred into a clear 96-well assay plate and the UV absorption was read 540 nm. Positive and negative control experiments were carried out with 0.1% Triton-X (100%) and buffer alone, respectively.

Dynamic Light Scattering

After formulation, the LNPs-siRNA were diluted with 1×PBS to a final siRNA concentration of 2 µg/mL. The average particle size was measured via dynamic light scattering on a Malvern Zetasizer Nano ZS (Malvern Instruments, Worcestershire, UK). All experiments were carried out in triplicates.

RiboGreen™ Assay

After formulation, the LNPs-siRNA were diluted with IX PBS to a final siRNA concentration of 1 µg/mL. The total and unbound siRNA concentration after formulation was determined using the Quant-iT RiboGreen™ RNA assay (Invitrogen) in the presence or absence of 1% Triton-X. The siRNA entrapment efficiency was calculated using the following equation:

$$100 \times (siRNA_{total} - siRNA_{unbound})/siRNA_{total}.$$

6-p-toluidinyl-naphthalene-2-sulfonate (TNS) Assay

A series of buffers with pH ranging between 2.5 and 8.5 were prepared by adjusting the pH of a solution containing 10 mM citrate, 10 mM phosphate, 10 mM borate, and 150 mM NaCl with 1N HCl. 90 µL of each buffer solution was added to a 96-well plate. A 300 µM stock solution of TNS was prepared in DMSO and 2 µL of this solution was added to the buffer solutions in the 96 well plate. After formulation, 10 µL of an LNP solution (prepared without siRNA) was added to the above mixture such that the synthesized lipid concentration (not co-lipids) in the final mixture was 22 M. The fluorescence of the resulting solution was obtained on a Tecan Safire 2 Microplate reader using an excitation wavelength of 325 nm and an emission wavelength of 435 nm. The fluorescence signal was plotted against pH and fitted using a three-parameter logistic equation (GraphPad Prism v.5.0a, GraphPad Software, San Diego Calif. USA). The pH value at which half of the maximum fluorescence is reached was reported as the apparent $pK_a$ of the LNPs.

Confocal Microscopy

HeLa cells were seeded at 1.5×104 cells per well in black (clear bottom) 96-well plates (Greiner Bio-one) and incubated for 24 hours prior to transfection. The cells were then transfected with the inventive LNPs containing 50 ng of FRET-labeled probes for one hour. The cells were washed, fixed, and counterstained in PBS containing Hoechst (2 µg/mL) for nuclei identification. The cells were then imaged using an automated spinning disk confocal microscope (OPERA, Perkin Elmer) with a 40× objective. The exposure rates were maintained constant for individual fluorophores across the 96-well plate. The images were acquired from the Acapella software with a 20 µm scale bar.

Results

Figure 6:
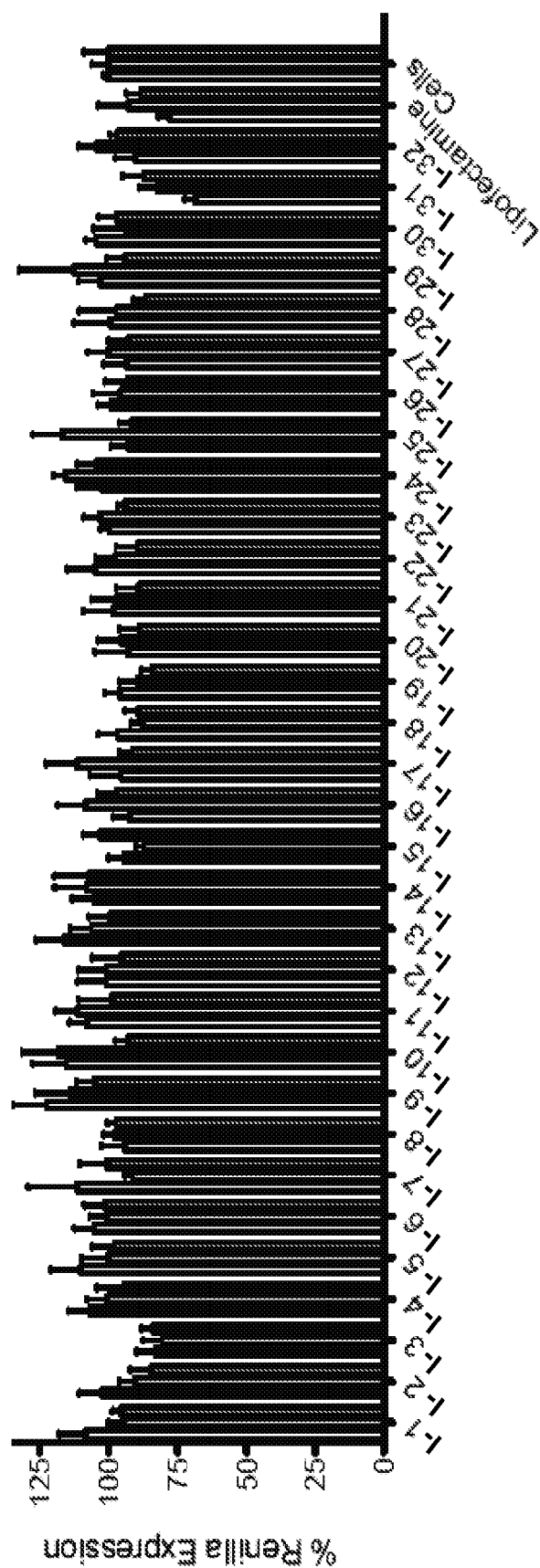
FIG. 6 shows the Renilla expression after a 24 hour transfection with LNPs-siRNA against firefly luciferase in a HeLa cell line expressing both firefly and Renilla luciferase. Decrease in Renilla expression relative to control is a sign of LNP-mediated toxicity or off-target effects. The results are presented as Renilla expression normalized to control cells treated with 1X PBS. White bars: 50 ng of siRNA; gray bars: 25 ng of siRNA; black bars: 10 ng of siRNA. Error bars represent S.D., n=6.
Figure 7B:
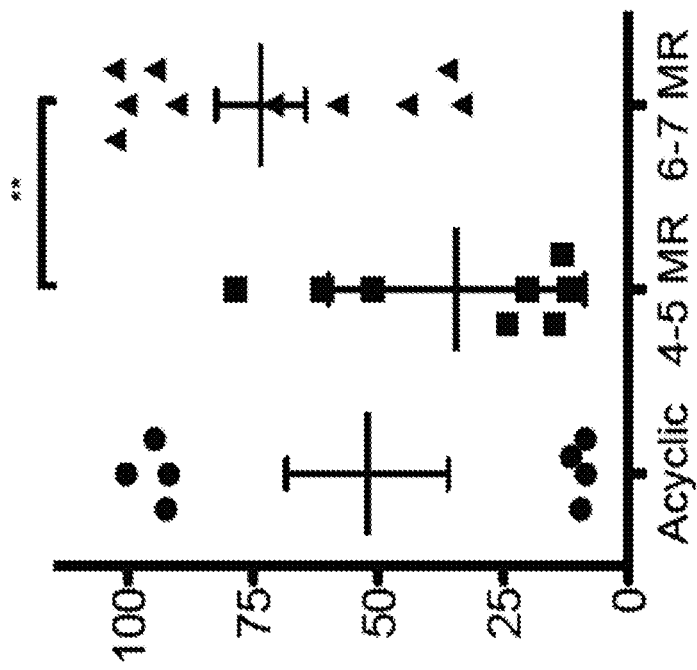
FIG. 7B shows the in vitro transfection data grouped according to lipids that have acyclic head groups, 4- to 5-membered rings (4-5 MR) and 6- to 7-membered rings (6-7 MR) in the head group. [**]P<0.01.
Figure 7A:
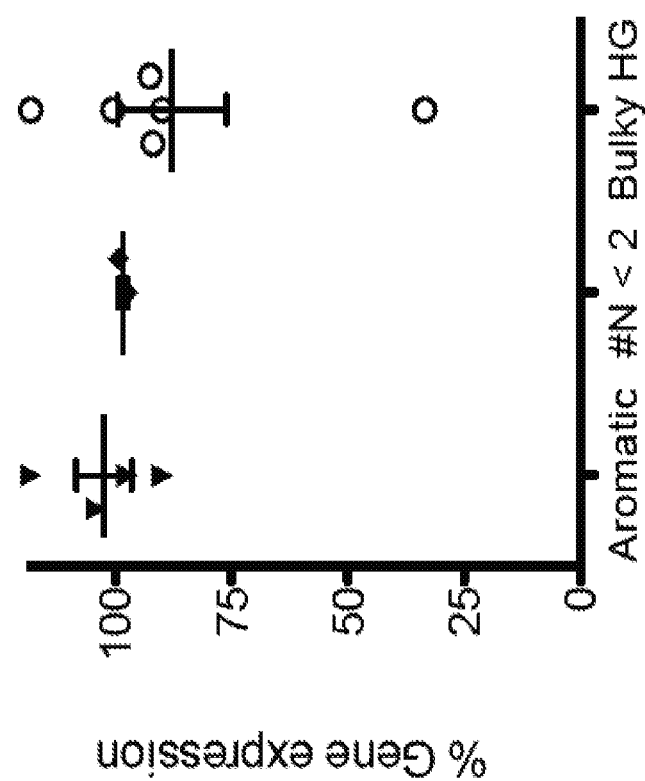
FIG. 7A shows the in vitro transfection data grouped according to lipids that contain aromatic groups, have less than two nitrogen atoms, and those with bulky head groups (compounds I-4, I-6, I-21, I-24, I-29 and I-30).
Figures 8A, 8B:
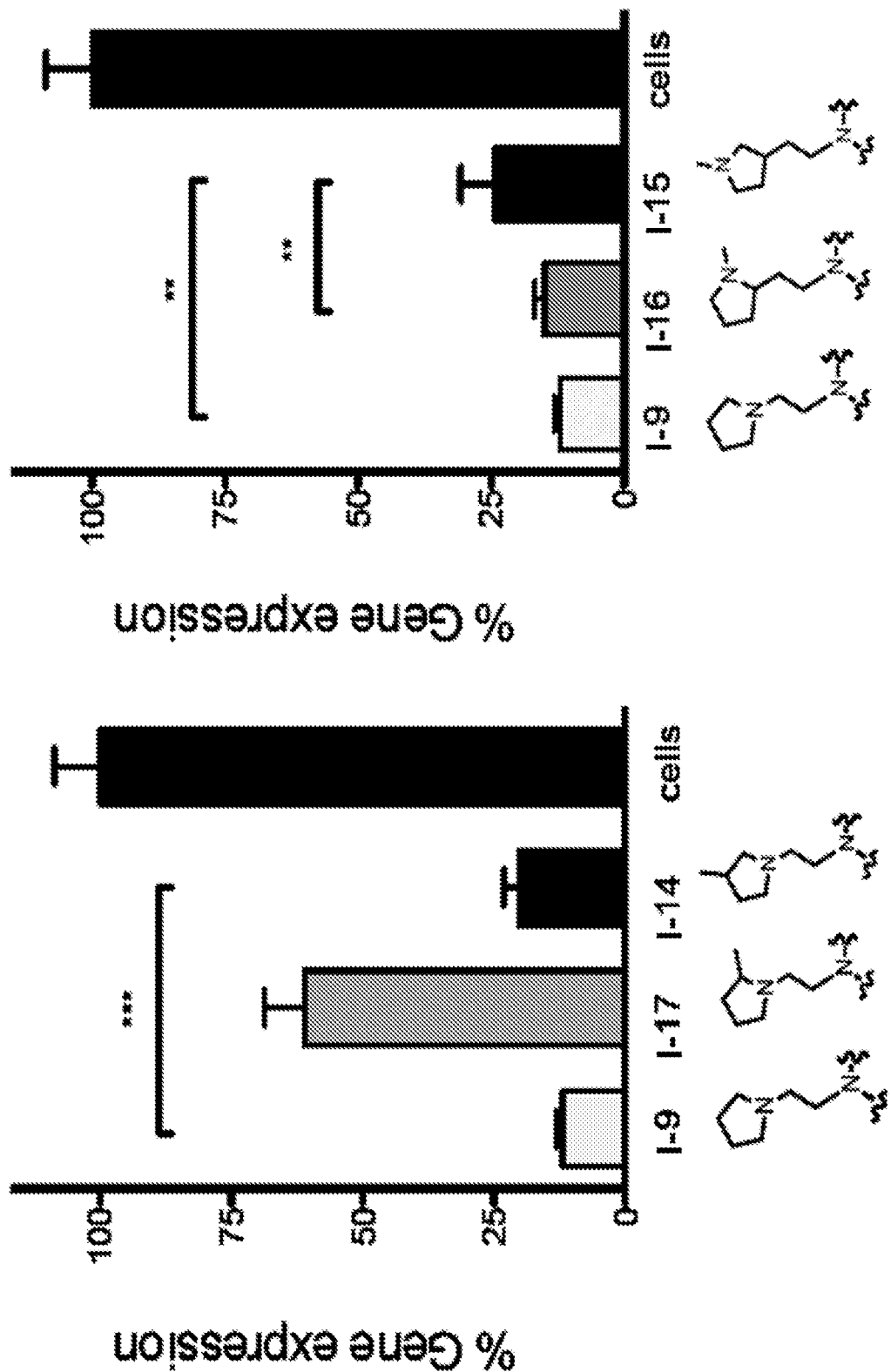
FIG. 8A shows the structure activity relationship between lipids I-9, I-17, and I-14 (effect of amine position in the 5-membered ring).
FIG. 8B shows the structure activity relationship between lipids I-9, I-16, and I-15 (effect of the relative position of the methyl group on the pyrrolidine ring). Error bars represent S.D., n=6. [] P<0.01, [*]P<0.001.

Each member of the lipid library was formulated into LNPs with co-lipids (DSPC, Cholesterol and PEG-lipid) and anti-firefly luciferase siRNA. HeLa cells expressing both firefly and Renilla luciferase genes were transfected with the LNPs in serum containing media for 24 hours and assayed thereafter. Renilla expression was monitored as an internal control for LNP related cytotoxicity. Transfection with LNPs in vitro resulted in a "hit" rate of about 40% (i.e. 40% of the lipids achieved greater than 50% gene silencing) even at siRNA doses as low as 10 ng (about 7 nM siRNA concentration). None of the LNPs tested appeared toxic to cells at the doses tested (FIG. 6). After further analysis of the LNP transfection data, several SARs become apparent. It was observed that compounds containing aromatic (compounds I-13, I-20, I-29, and I-30) and bulky head groups (compounds I-4, I-6, I-21, I-24, I-29, and I-30) as well as those with less than two nitrogen atoms (compounds I-18 and I-26) gave poor gene silencing (FIG. 7A). There was no difference in performance between structures bearing acyclic head groups. However, compounds with four to five membered rings in their head groups on average performed better than those with six to seven membered rings in their head group (FIG. 7B). It was also observed that a subtle change in the group neighboring the ionizable amine group (see, e.g., compounds I-9, I-17, and I-14) or a change in the position of the ionizable amine group (see, e.g., compounds I-9, I-16, and I-15), leads to dramatic changes in gene silencing performance (FIGS. 8A and 8B).

Figure 2A:
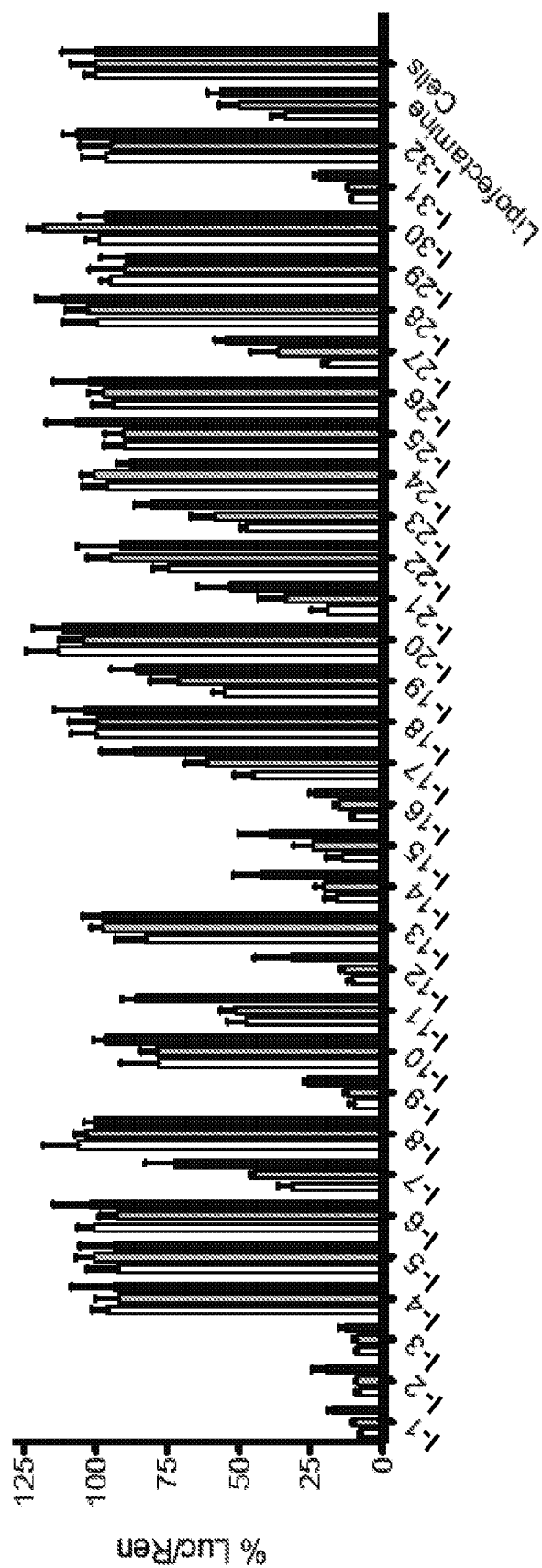
FIG. 2A shows the dose-dependent knockdown of firefly luciferase via LNP-siRNA in a HeLa cell line expressing both firefly and Renilla (Ren) luciferase. Results are presented as the luciferase expression normalized to the Renilla expression (Luc/Ren). White bars: 50 ng siRNA; gray bars: 25 ng siRNA; black bars: 10 ng siRNA. Error bars represent standard deviation (S.D.), n=6.
Figure 2B:
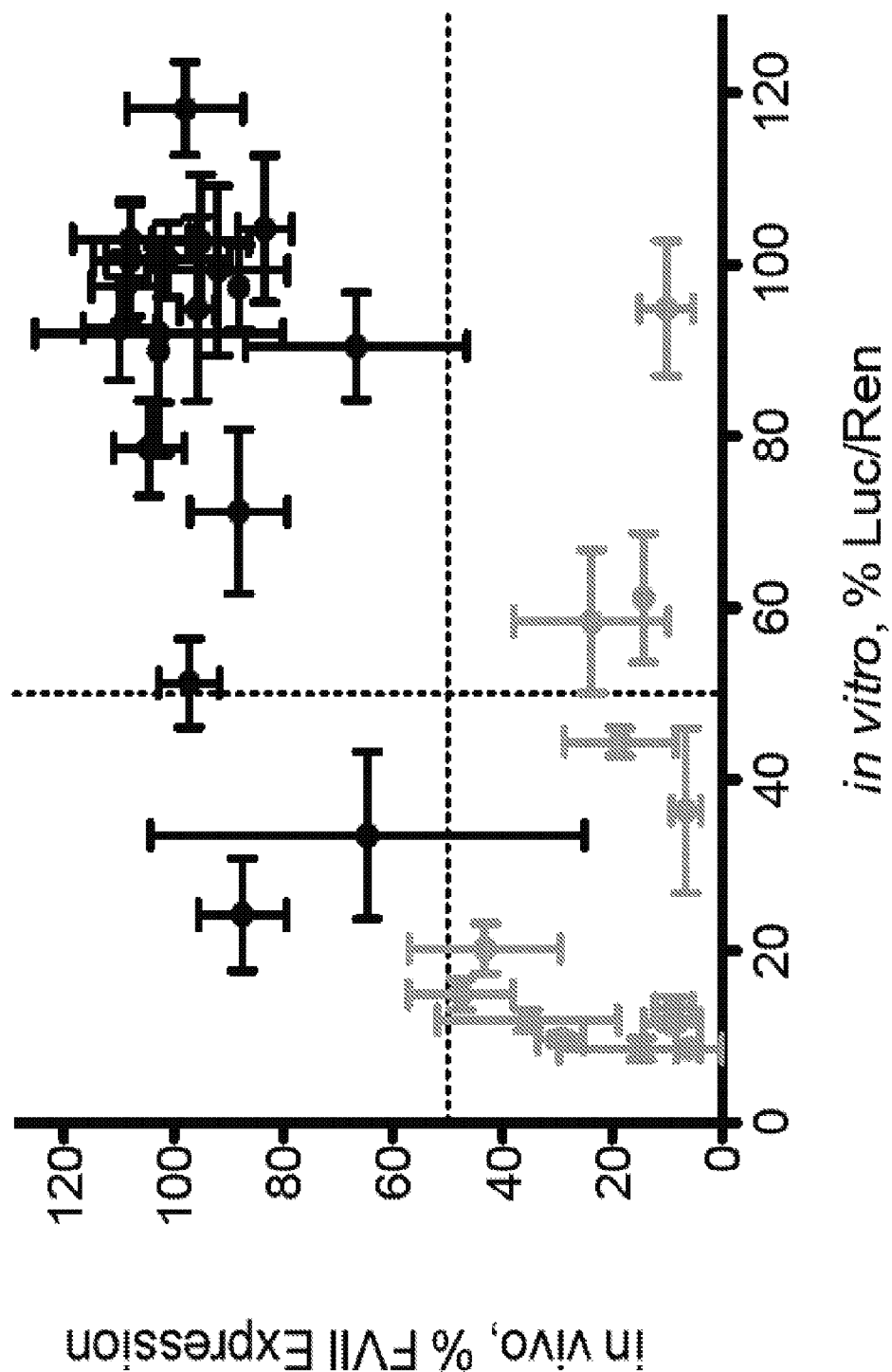
FIG. 2B shows the correlation between in vitro luciferase (Luc/Ren, at 25 ng siRNA) and in vivo FVII gene expression. Vertical error bars represent S.D., n=6. Horizontal error bars represent S.D., n=3. Dotted lines represent the 50% in vitro and in vivo gene expression levels. False positives: top left corner. False negatives: bottom right corner. Grey: compounds that gave better than 50% knockdown in vivo. Black: compounds that did not give better than 50% knockdown in vivo.
Figure 9:
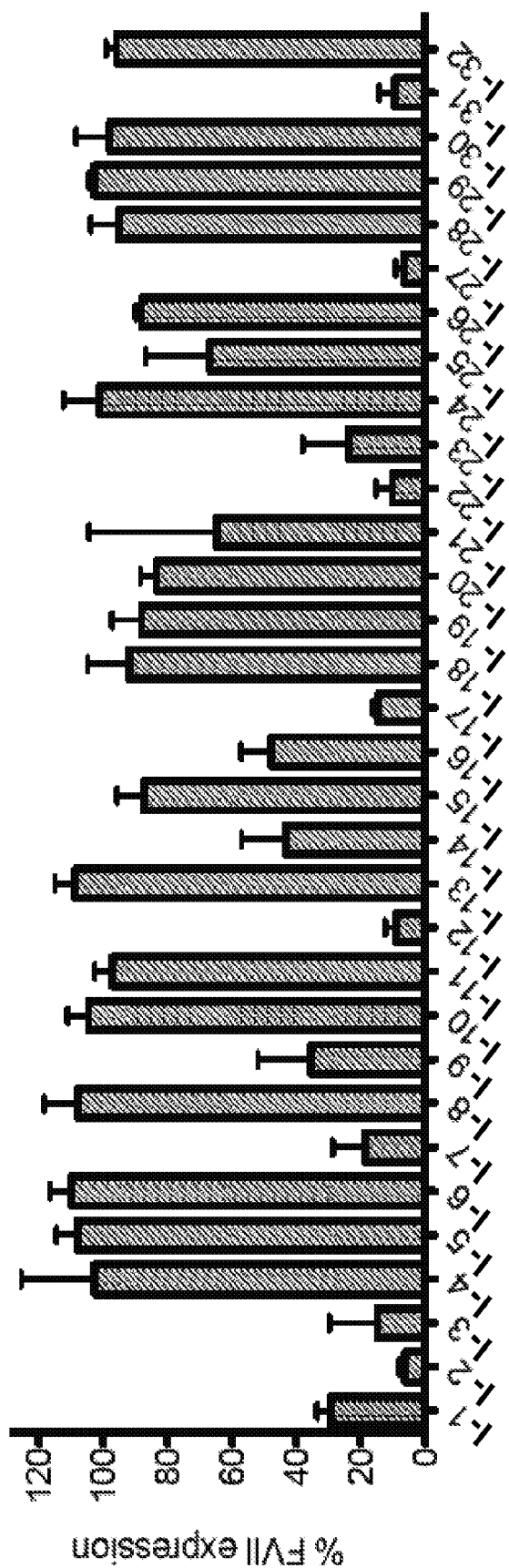
FIG. 9 shows the in vivo Factor VII (FVII) gene expression two days after administration of an inventive compound and siRNA at a dose of 1 mg/kg of the siRNA. Error bars represent S.D., n=3.

The performance of the inventive LNPs in vivo was evaluated using a mouse murine clotting factor VII (FVII) model for monitoring hepatocyte-specific delivery (3, 16, 26). The inventive lipids were formulated into LNPs with siRNA against FVII and administered i.v. at a dose of 1 mg/kg. Knockdown results from these experiments showed a hit rate of about 40%, similar to the rate obtained in vitro (FIG. 9). LNPs that show better than 50% gene silencing in vivo are colored grey. Furthermore, correlation between these results and the in vitro transfection data (at 25 ng siRNA) has an $R^2$=0.53, with two false positives and three false negatives (FIG. 2B). The former is expected as the barriers to delivery encountered in vivo are known to be more stringent that those in vitro. The latter shows that potential in vivo "hits" may be discounted and never discovered. To understand the mechanism behind the uncovered SARs and in vitro-in vivo correlations, an investigation was carried out into the physicochemical properties of these LNPs as well as the barriers they need to overcome to allow for efficient delivery of the siRNA payload.

Figure 3A:
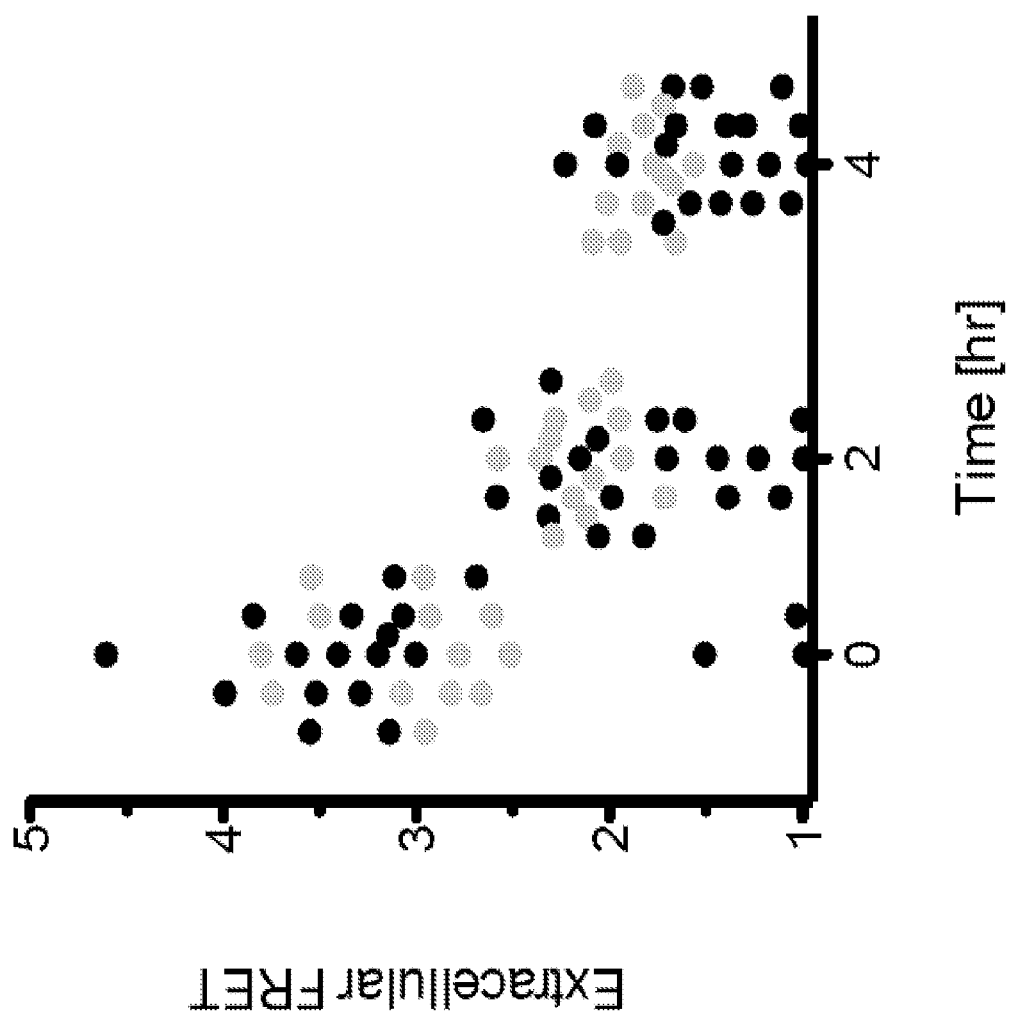
FIG. 3A shows the extracellular FRET of the LNPs as a function of time.
Figure 3B:
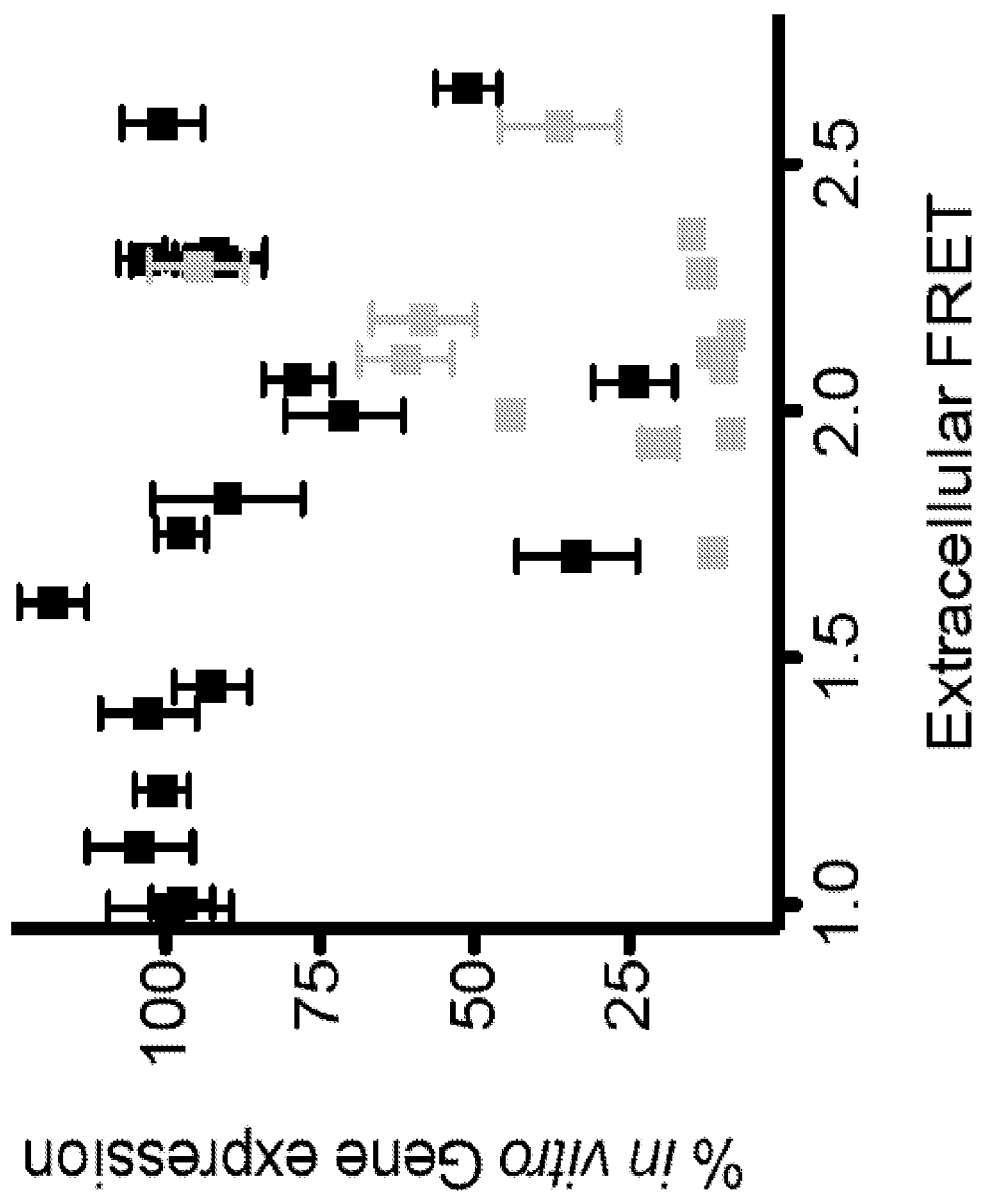
FIG. 3B shows the correlation between in vitro % gene expression and extracellular FRET (measured after 2 hours). Black vertical error bars represent S.D., n=6.

One of the early barriers (barrier #1 in FIG. 1) encountered by nanoparticles en route to the target cell is serum protein binding and the potential for premature nanoparticle disassembly in the extracellular milieu. As such, extracellular stability of the LNPs was measured via a recently developed FRET-labeled siRNA probe technique (26-28). The probe design is based on a FRET-labeled siRNA pair (Alexa Fluor® 594/647) that fluoresces due to the proximity of the siRNA pair in the intact nanoparticle. A key advantage of this technique is that the lipids do not need labeling, thus allowing the entire library to be assayed and compared using the same probe conditions. LNPs formulated with the FRET-labeled siRNA pair were monitored in serum containing cell media at 37° C. for four hours. FIG. 3A shows the assembly state of the LNPs (represented by the FRET signal) as a function of time. The data shows that LNPs with near complete disassembly (i.e. FRET values near 1) after two hours had very poor gene silencing activities (FIG. 3B).

Figure 3C:
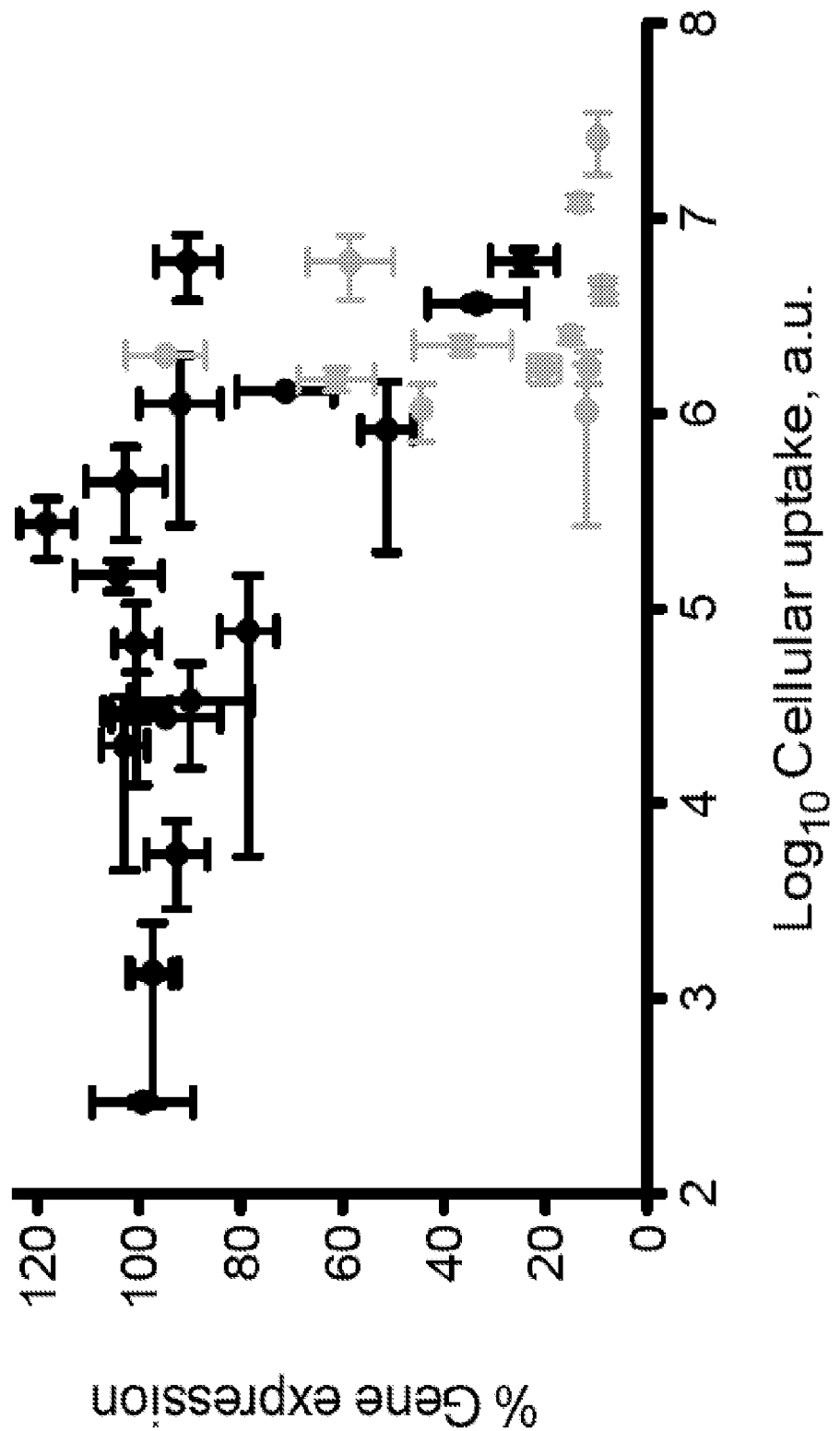
FIG. 3C shows the correlation between in vitro % gene expression and cell uptake. Black vertical error bars represent S.D., n=6. Horizontal error bars represent S.D., n=2.

Next, LNPs that remain stable in the extracellular milieu must cross the cellular membrane barrier (barrier #2, FIG. 1) to gain entry into the cell's endocytic compartment. As such, cellular uptake of LNPs containing fluorescently labeled siRNAs was measured in HeLa cells via flow cytometry. The results in FIG. 3C indicate that a certain uptake threshold exists below which gene silencing is not observed. These results indicate that although uptake is a critical barrier, it alone cannot guarantee efficient delivery.

Figures 3D, 3E:
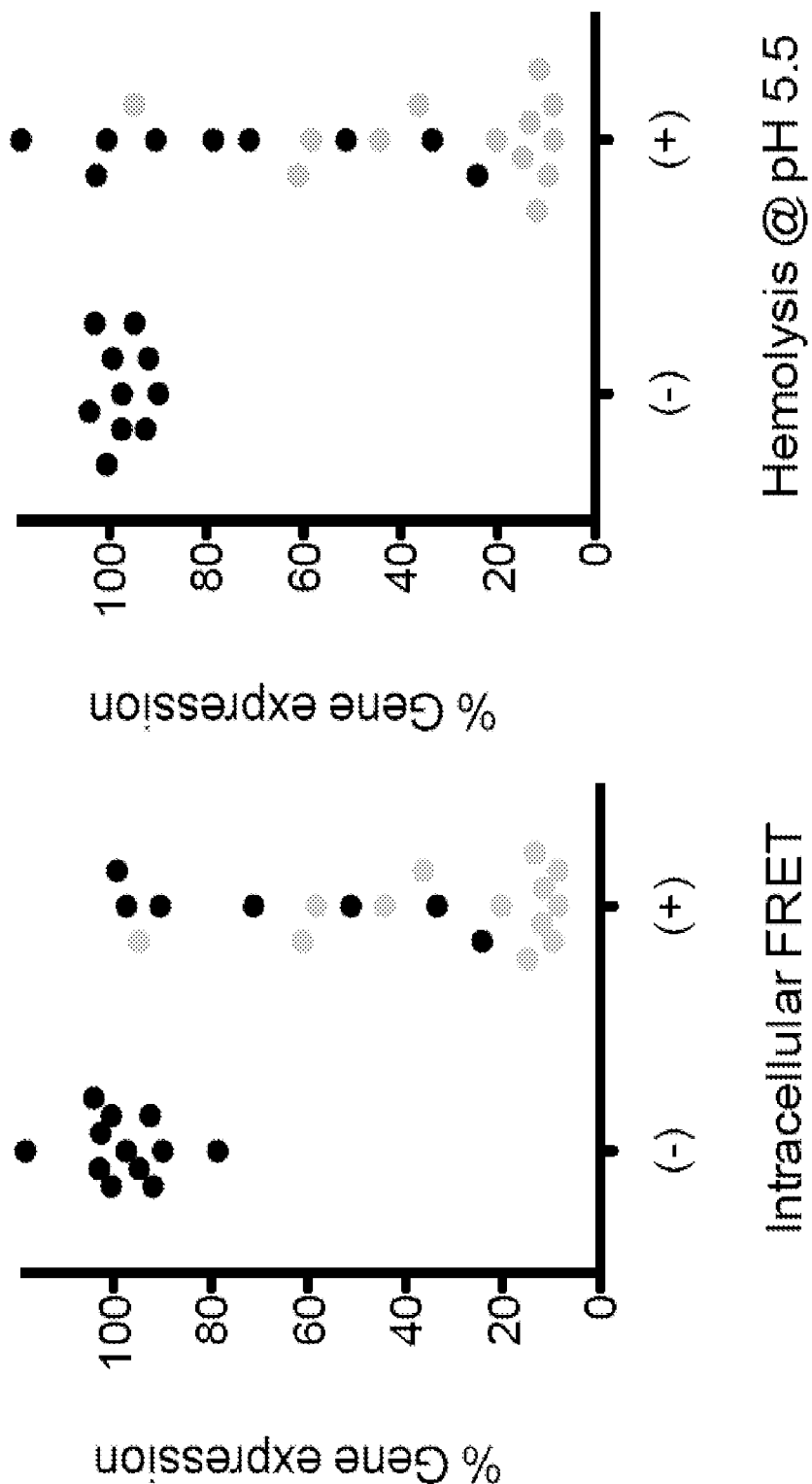
FIG. 3D shows the relationship between in vitro % gene expression and intracellular FRET. (+) and (−) indicate the presence and absence of an intracellular FRET signal respectively.
FIG. 3E shows the relationship between in vitro % gene expression and Hemolysis at pH 5.5. (+) and (−) indicate hemolysis greater or less than 10% (after normalization to the negative control). Grey: compounds that gave better than 50% knockdown in vivo. Black: compounds that did not give better than 50% knockdown in vivo.
Figure 10:
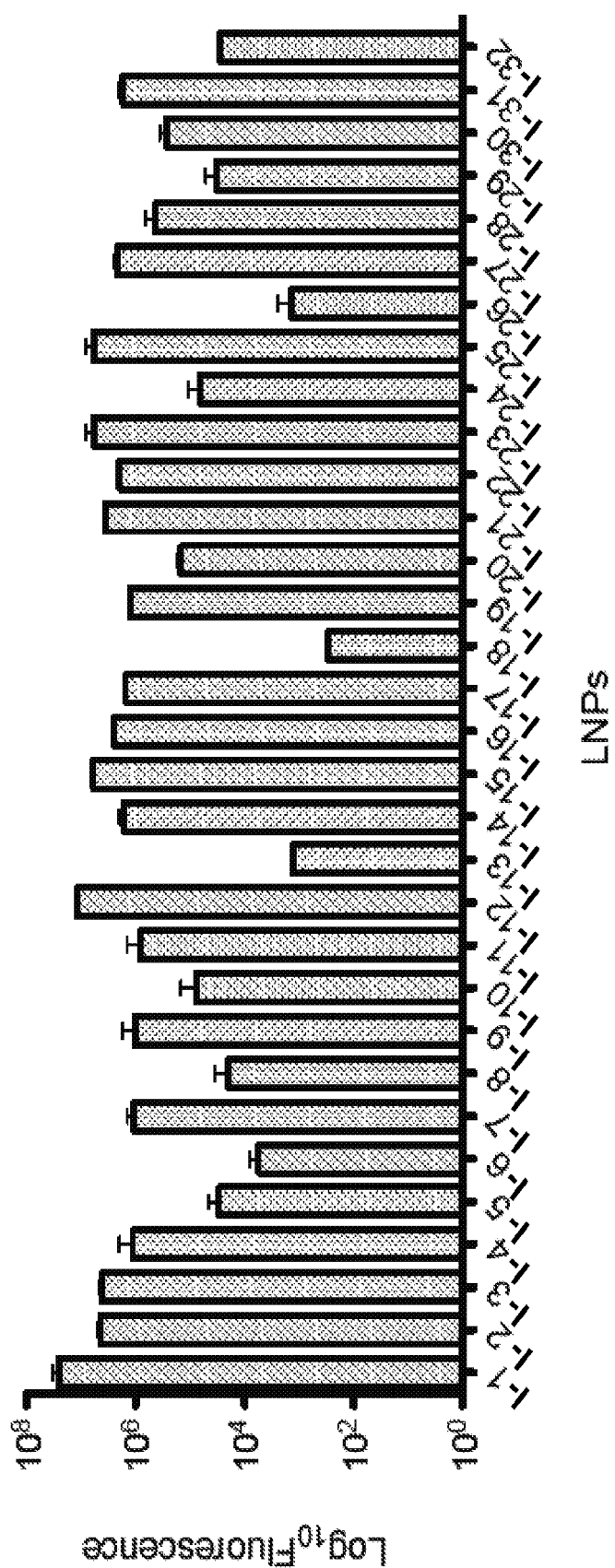
FIG. 10 shows the HeLa cell uptake after two hours incubation with the inventive LNPs containing an siRNA labeled with Alexa Fluor® 647 in serum containing media. Cells were analyzed via flow cytometry using settings for the Alexa Fluor® 647 channel: excitation via a 633 nm (red, HeNe) laser and emission via a 660/20 nm filter. Error bars represent S.D., n=2.
Figure 11:
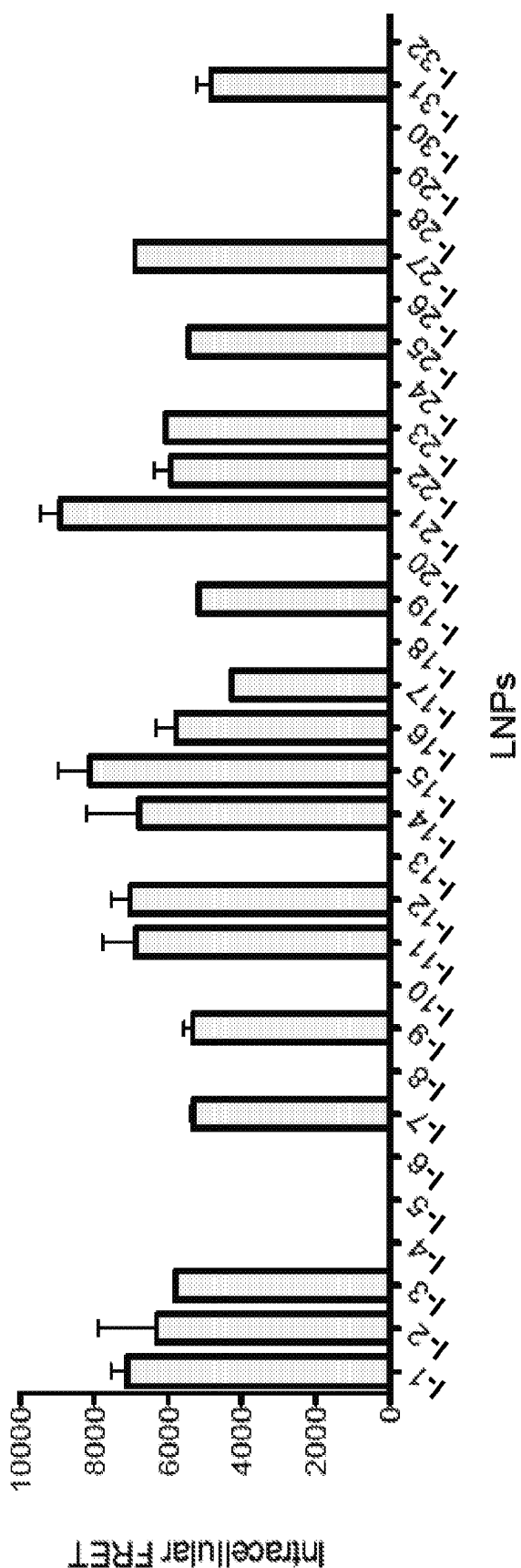
FIG. 11 shows the intracellular FRET analyzed via flow cytometry after transfection of HeLa cells with the inventive LNPs containing FRET-labeled siRNAs. Error bars represent S.D., n=2.

LNPs must cross the cellular membrane as intact nanoparticles and resist premature dissociation at the cell membranes via surface proteoglycans (barrier #3, FIG. 1) (27-30). Since cellular uptake is strictly a measure of total cellular associated fluorescence, LNPs that dissociate at the cell membrane or dissociated fluorophores that are nonspecifically taken up by cells may be included as part of the total cellular LNP count. To account for this non-LNP fluorescence, intact LNPs were differentiated from free siRNAs by measuring the FRET signal in HeLa cells soon after transfection with LNPs containing FRET-labeled siRNA probes. Intracellular FRET data at an early time point indicated that uptake of intact LNPs was necessary for gene silencing (FIG. 3D). LNPs that showed limited cellular uptake gave no intracellular FRET. However, a few LNPs with relatively high uptake such as compounds I-4 and I-28 (FIG. 10) did not give an intracellular FRET signal (FIG. 11). This result suggests that these LNPs may dissociate soon after cellular entry, thus explaining their high uptake but limited gene silencing performance.

Figures 12A, 12B:
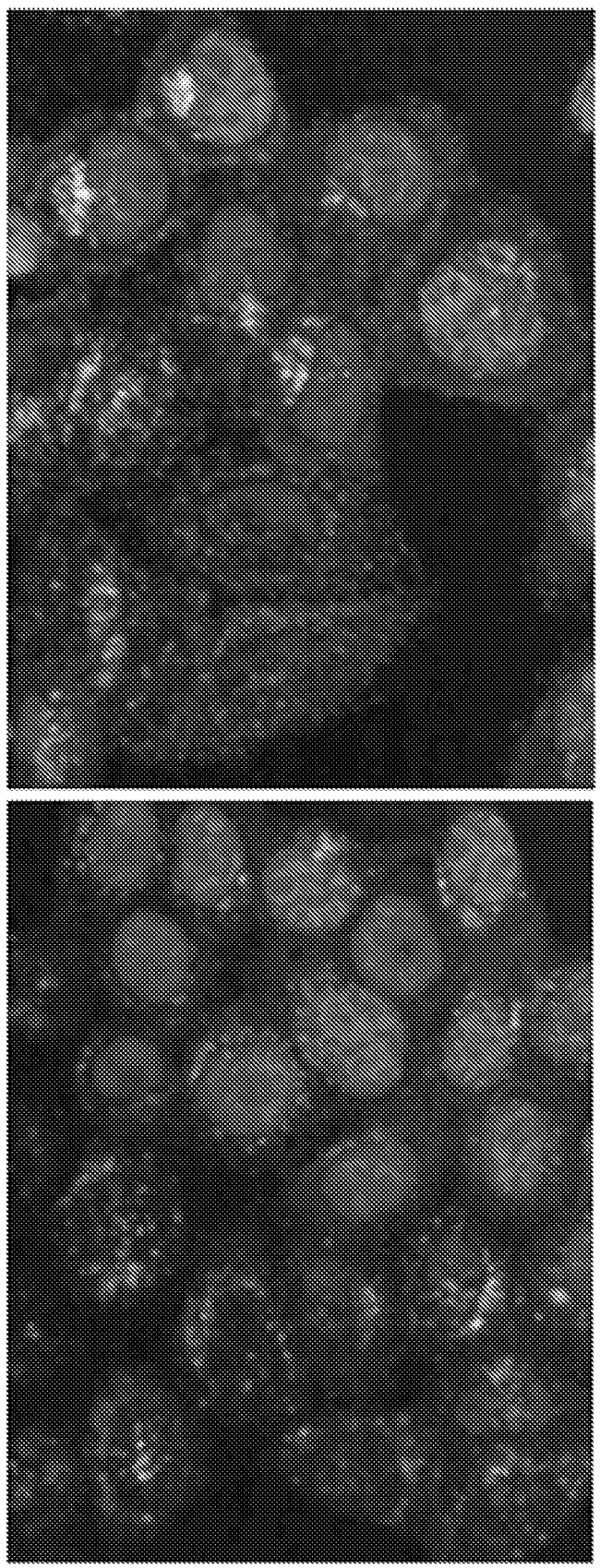
FIGS. 12A and 12B show the representative images of the inventive LNPs (I-2 and I-3) transfected into HeLa cells using FRET-labeled siRNA probes (Alexa Fluor®594 and Alexa Fluor® 647 labeled siRNAs). LNPs can be seen located near the cell membrane and inside endocytic vesicles. The green color in the images represents Alexa Fluor® 594, and the red color represents Alexa Fluor® 647. Co-localization of both dyes appears yellow. The nucleus is stained blue with Hoechst dye.
Figure 13A:
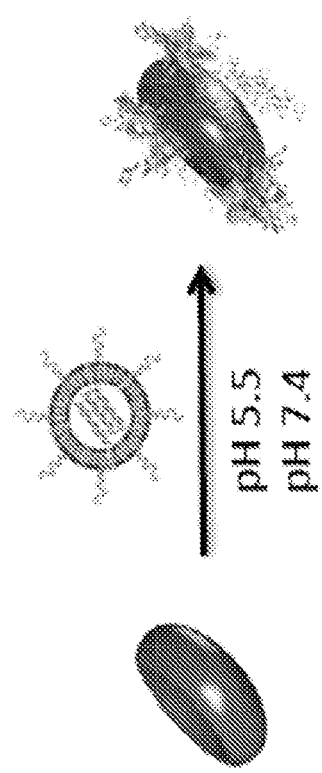
FIGS. 13A and 13B show the LNP-mediated hemolysis of red blood cells (RBCs) at pH 5.5 (white bars) and 7.4 (gray bars). Error bars represent S.E.M, n=3.
Figure 13B:
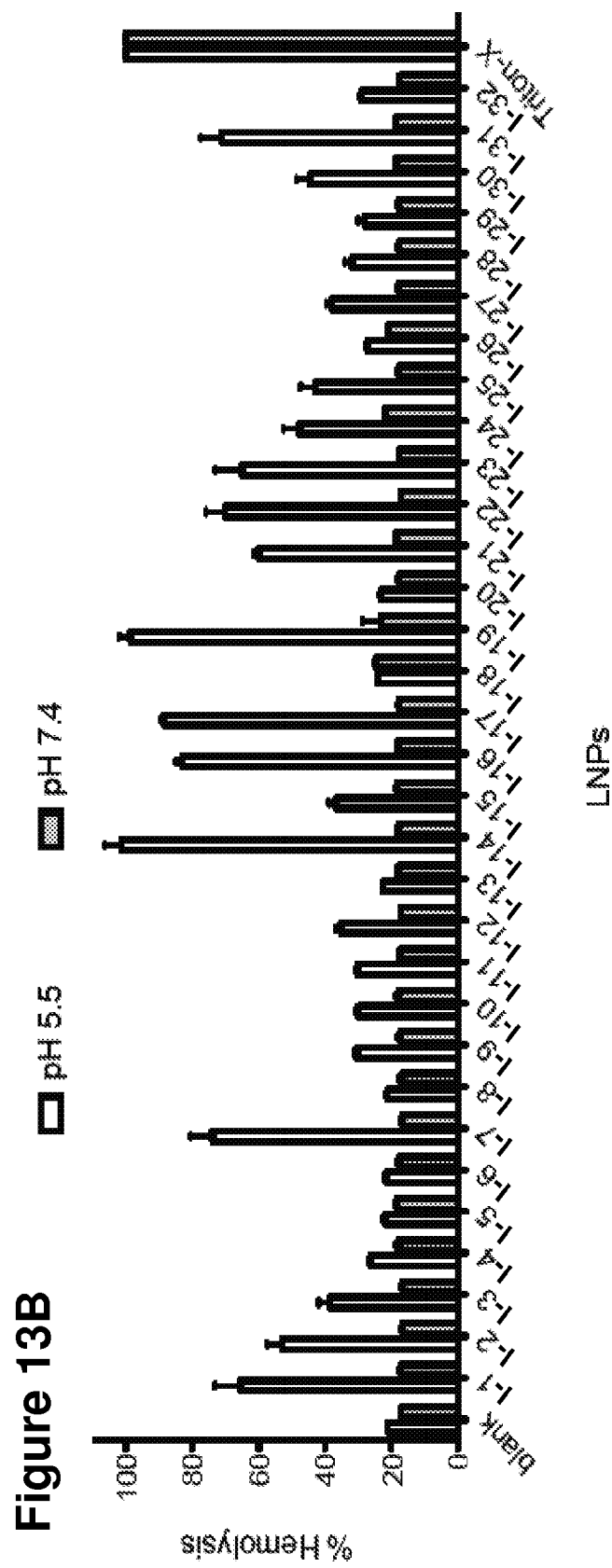

Following cellular uptake, it is believed that LNPs residing in the endocytic vesicles (FIG. 12) must escape this compartment (barrier #4, FIG. 1) in order to gain access to the RNAi machinery (29-31). The relative capacity for LNP mediated endosomal escape was simulated using a red blood cell (RBC) hemolysis assay. This assay was performed both at a physiological pH of 7.4 and endosomal pH of 5.5 (11, 31, 32). Membrane lysis at pH 7.4 is an indication of toxicity while lysis at 5.5 is a model for the ability of the LNPs to escape vesicular structures (e.g., endosomes/lysosomes) upon acidification. All LNPs tested were non-hemolytic at physiological pH (FIG. 13). However at pH 5.5, a majority of LNPs induced varying degrees of RBC hemolysis (FIG. 13). LNPs that showed less than 10% hemolysis (after normalization to the negative control) had very poor gene silencing activities (FIG. 3E). Although some LNPs appear to be hemolytic (e.g. compounds I-2 and I-3), large amounts of LNPs and siRNAs still appear to reside in the endocytic vesicles (FIG. 12, punctate dot structures in cells).

Figure 4A:
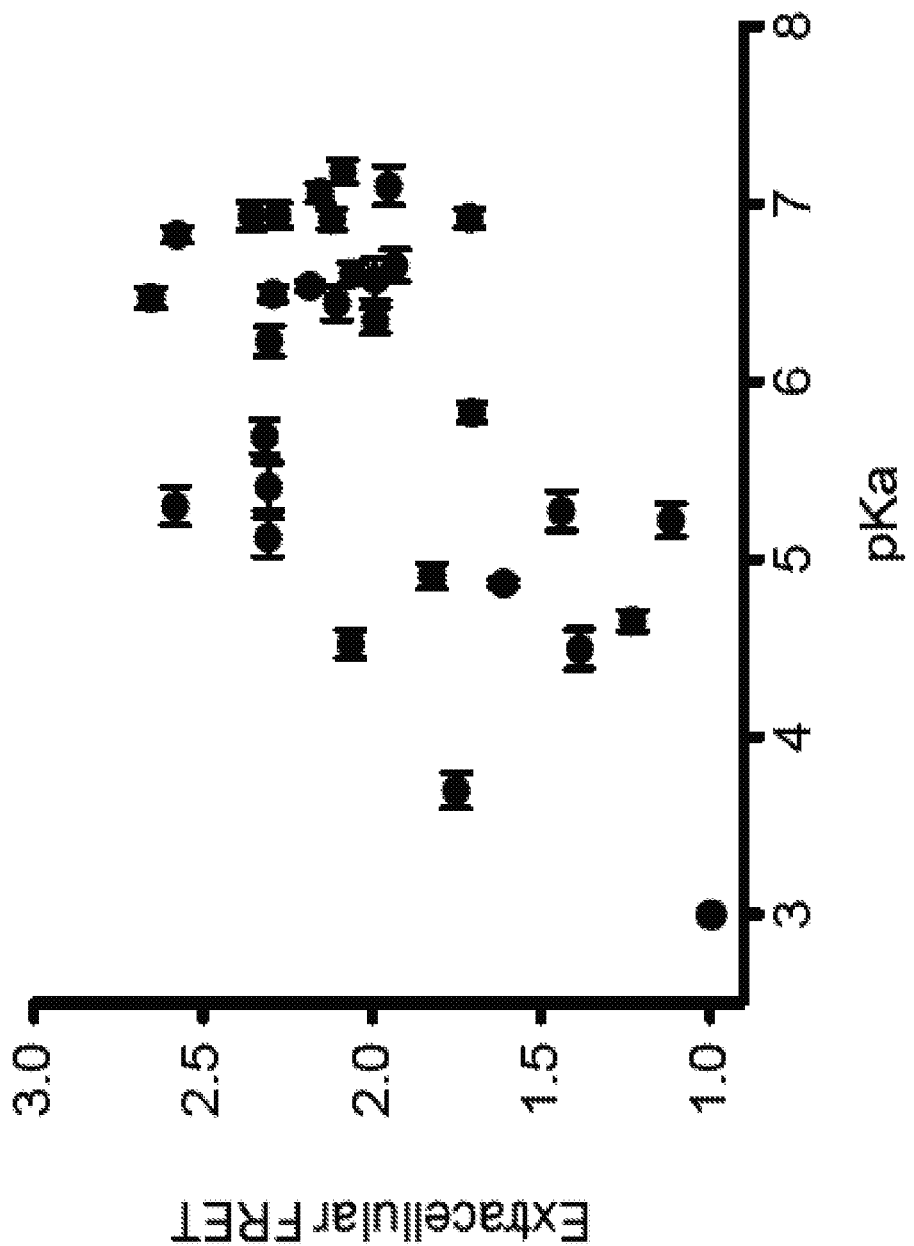
FIG. 4A shows the correlation between the extracellular FRET signal (after two hours of incubation in serum containing media) and the $pK_a$ values of the LNPs of the invention.
Figure 4B:
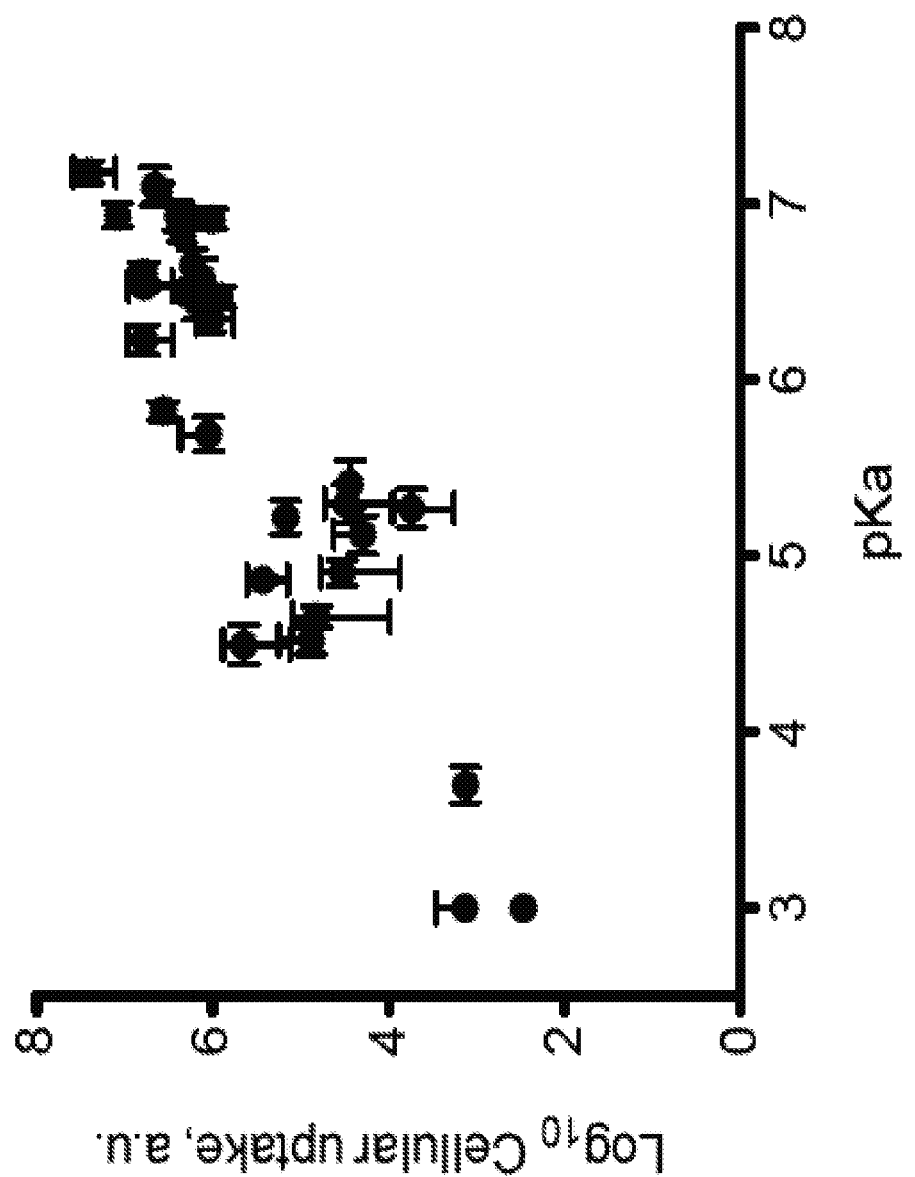
FIG. 4B shows the correlation between cell uptake of LNPs (after two hours incubation in serum containing media) and the $pK_a$ values of the LNPs.
Figure 4C:
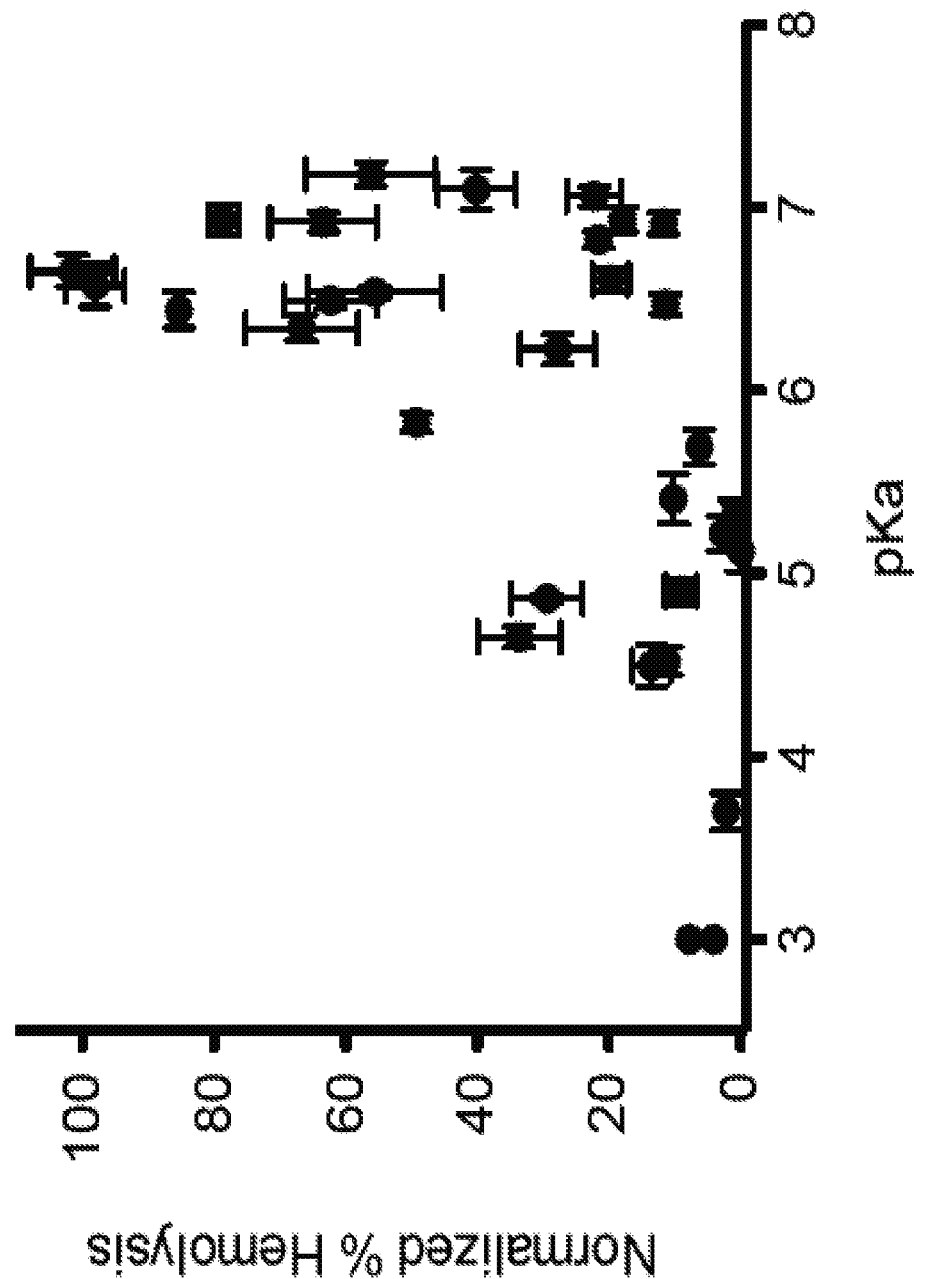
FIG. 4C shows the correlation between the LNP-mediated cell hemolysis at pH 5.5 and the $pK_a$ values of the LNPs.
Figure 4D:
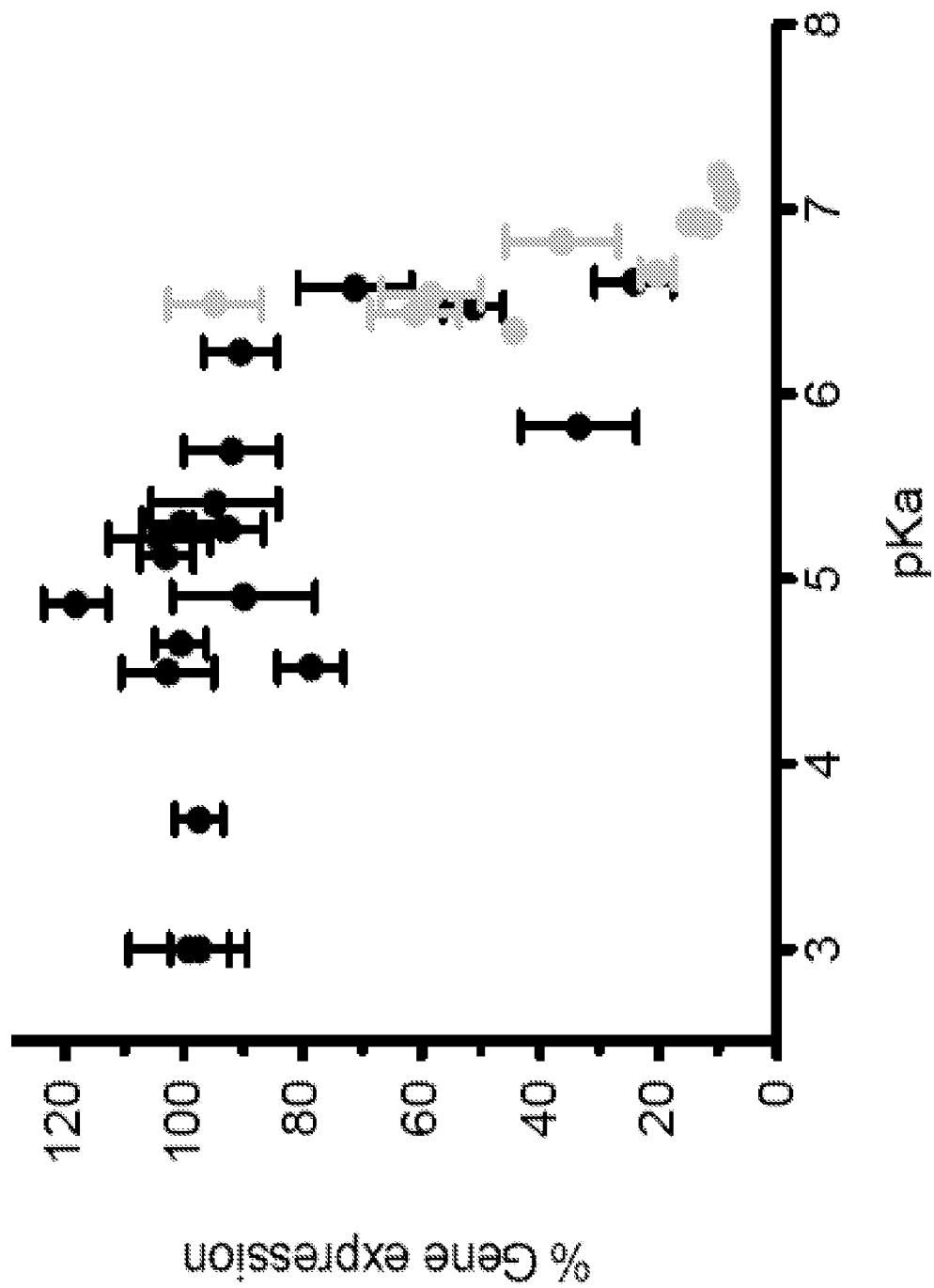
FIG. 4D shows the correlation between the $pK_a$ values of the LNPs and in vitro gene expression after transfection with 25 ng of siRNA. Grey: LNPs that gave better than 50% knockdown in vivo. Black: LNPs that did not give better than 50% knockdown in vivo. Vertical error bars represent S.D., n=6.
Figure 14:
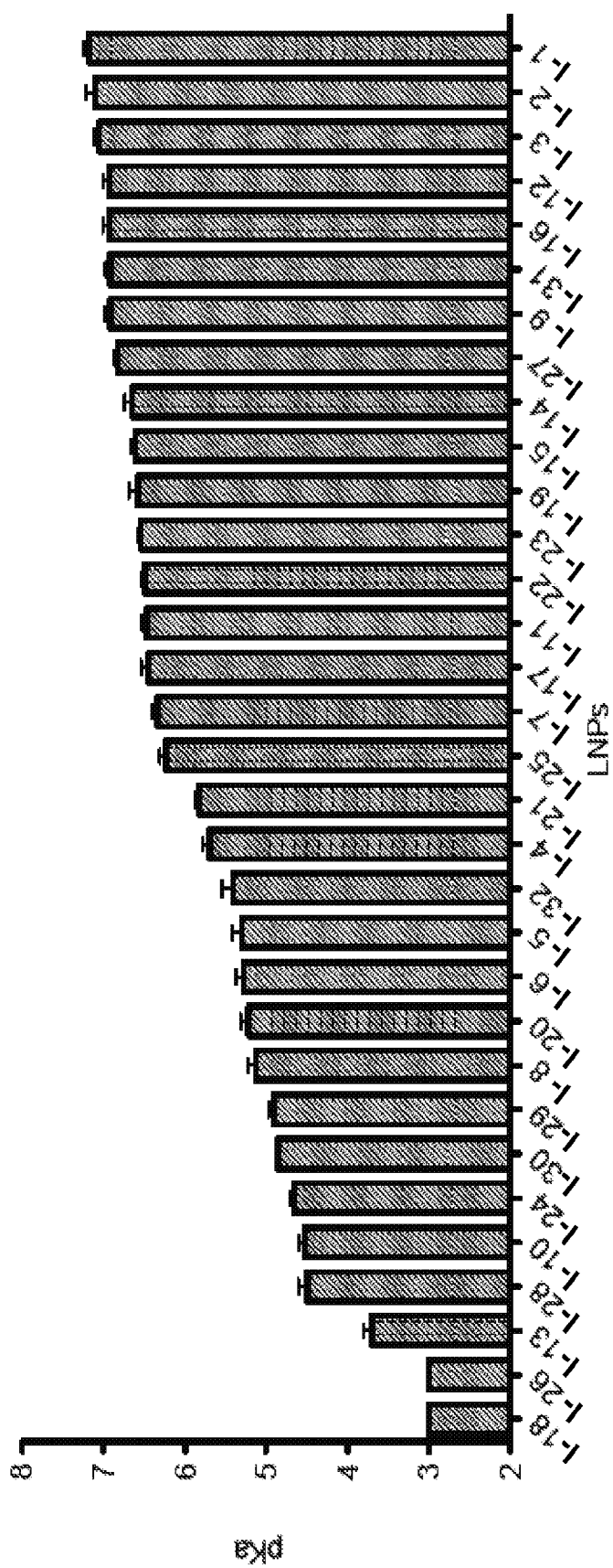
FIG. 14 shows the determination of the $pK_a$ values of the inventive LNPs via 6-p-toluidinyl-naphthalene-2-sulfonate (TNS) fluorescence titration between pH 2.5 and 8.5. Sigmoidal best-fit analyses were applied to the S-curves with $pK_a$ defined as the pH at half-maximal fluorescence intensity. Error bars represent standard error from the calculation. All experiments were done in duplicates.

Three physicochemical properties of the LNPs were investigated, including LNP size, siRNA entrapment and $pK_a$. Of these three, the LNP $pK_a$ showed the strongest correlation with biological barriers and gene silencing. LNP $pK_a$ was measured using a well-known 2-(p-toluidino)-6-napthalene sulfonic acid (TNS) assay (11, 32) by titrating the LNPs from pH 2.5 to 8.5. The pKa of each fully formulated LNP was determined from the resulting fluorescence titration S-curve using a curve-fit analysis. The advantage of this method is that LNP structure and formulation are taken into account and thus the measured $pK_a$ represents that of the LNP as a whole rather than just the individual lipid (11, 13). The measured $pK_a$ values (FIG. 14) showed good correlations with extracellular FRET and cellular uptake (FIG. 4B). This suggests that the charge state of the LNP has an influence on the stability and cellular uptake of LNPs. The $pK_a$ of the LNPs also showed a non-linear correlation with their hemolytic ability at pH 5.5 (FIG. 4C). LNPs with strong hemolytic ability (above 50% hemolysis) had $pK_a$ values between 6 and 7 (FIG. 4C). Finally, the $pK_a$ values of the LNPs show a non-linear correlation with in vitro gene silencing (FIG. 4D). All the top performers in vivo (above 50% silencing, color coded blue or grey in FIG. 4D) have $pK_a$ values in the range of 6 to 7 and all lipids with $pK_a$ values below 5.8 (14 out of 32 compounds) were unable to silence the target gene both in vitro and in vivo. These results show that an optimal pH range between 6.2 and 6.5 is preferred for maximum activity of ester and dioxolane based lipids (13).

Figure 15:
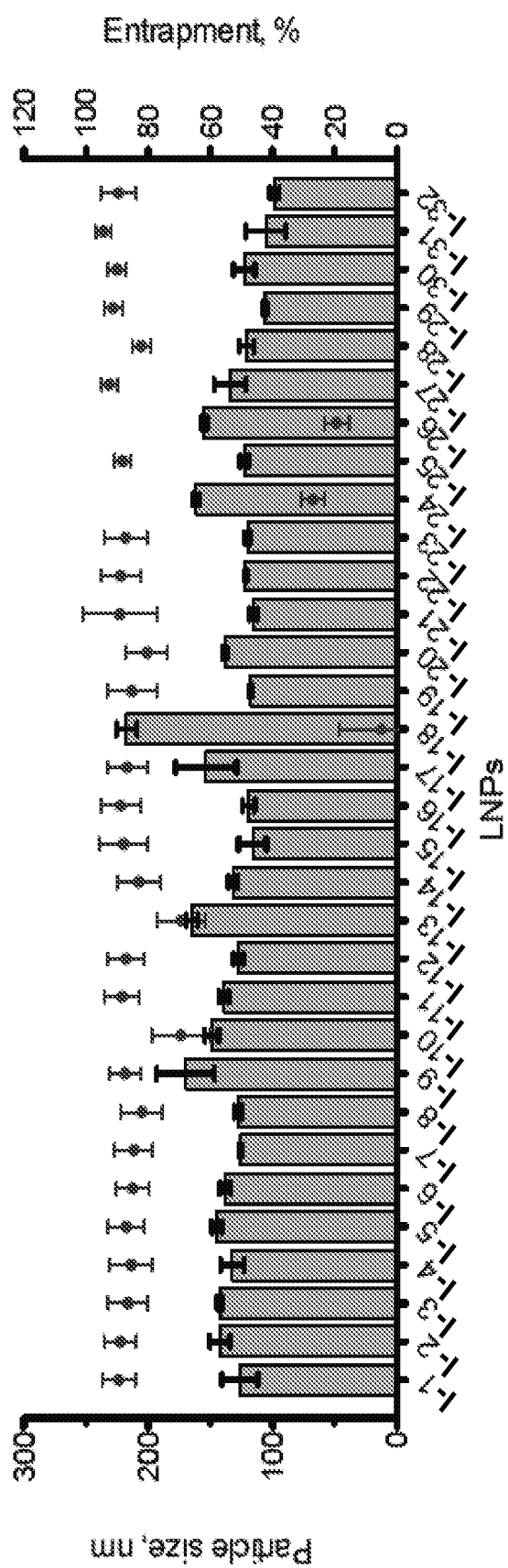
FIG. 15 shows the effective diameter (gray bars) and siRNA entrapment (black dots) of the inventive LNPs. Error bars represent S.D., n=3.

The LNPs examined all had similar diameters as measured by dynamic light scattering (FIG. 15). The siRNA entrapment for each LNP was measured via a Ribogreen™ exclusion assay (FIG. 15), and the results indicate that compounds with low entrapment efficiencies (under 50%) such as compounds I-18, I-24, and I-26 are still able to form nanoparticles (see particle size in FIG. 15) but are unable to silence the target gene.

Discussion

Figure 5:
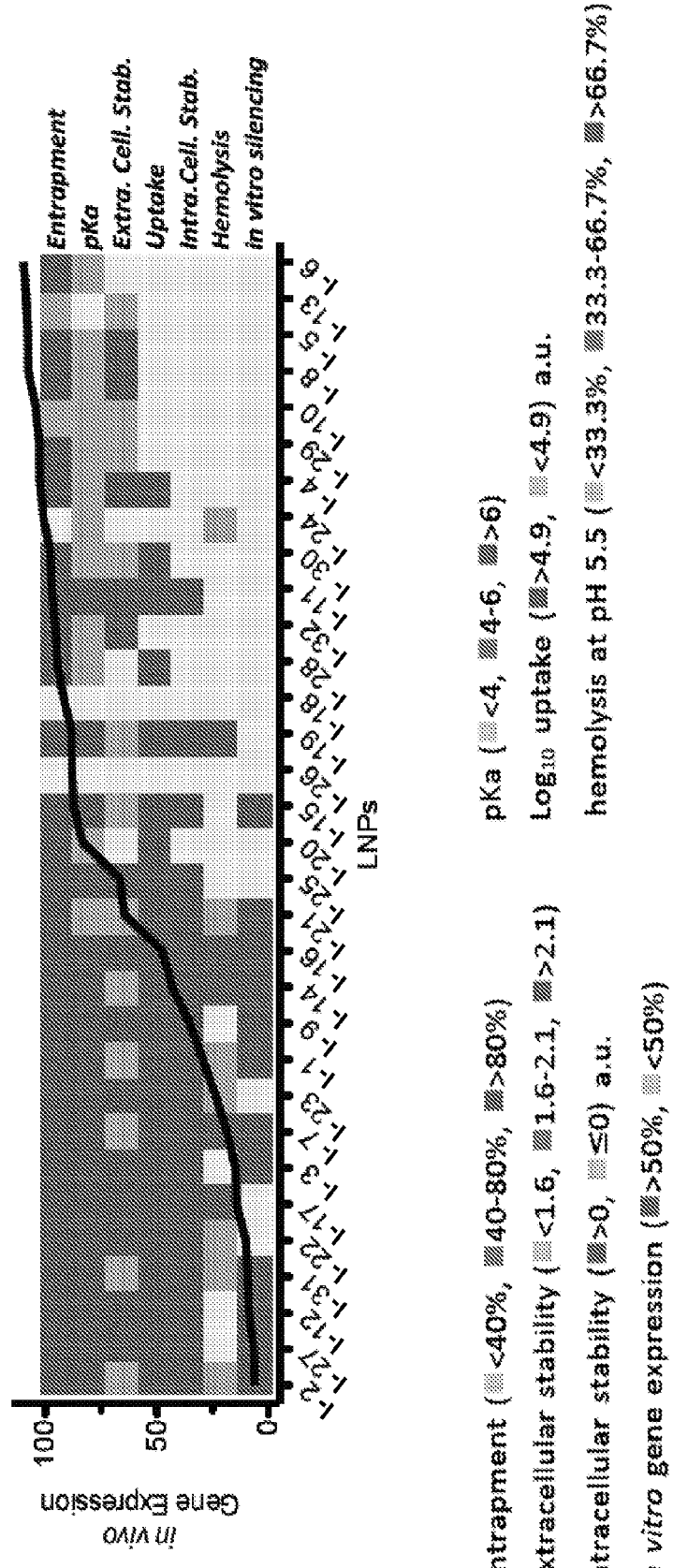
FIG. 5 is a heat map representation of the physicochemical properties and cellular functions of the LNP library from FIG. 1 plotted against their in vivo gene expression (black line) after administration of an siRNA at a 1 mg/kg dose.

In order to rationally design nanoparticles that can overcome the transport barriers facing delivery of siRNAs, it is necessary to understand the relationship between the physicochemical properties of the nanoparticles and the biological barriers they face. For this reason, multiple parameters associated with the barriers to delivery and physicochemical properties of LNPs were evaluated. Results from this evaluation suggest that most barriers and properties present a certain threshold below which efficient delivery is not realized. For example, LNPs showing less than 10% hemolysis were inefficient at silencing the target gene. Likewise, LNPs with $pK_a$ values less than 5.5 were unable to silence the target gene in vitro and in vivo. It was envisioned that the collective of all the measured parameters might provide additional insight into the potential for in vivo activity beyond what is inferred from in vitro gene silencing alone. To do this, the measured parameters and properties were condensed into a simplified heat map and overlaid the heat map with gene silencing performance (FIG. 5).

Each row in the heat map represents a physicochemical property or parameter associated with a cellular barrier (right y-axis) and the color gradient (light, medium, and dark grey) represents their respective magnitude. For example, the dark grey blocks in the first row in FIG. 5 represent high siRNA entrapment values (80-100%) while the light grey blocks represent low entrapment values (under 40%). The collective data set in FIG. 5 indicates that LNPs capable of overcoming most of the listed barriers (greater number of red or black blocks) are able to silence the target gene in vivo. Pre-screening based on the collective data as a metric resulted in zero false negatives and two false positives (compounds I-15 and I-19). In contrast, three false negatives (compounds I-17, I-22, and I-23) and two false positives (compounds I-15 and I-21) were obtained using in vitro gene silencing alone as a screening parameter (FIG. 2B vs. FIG. 5). As such, the collective use of all the in vitro parameters complements the use of the in vitro transfection data set alone for pre-screening and can help reduce the occurrence of false negatives.

The evaluation of multiple physicochemical properties and biological barriers can also aid design and optimization of future LNPs through the recognition of relationships between structure, biological function and biological activity. An example in this study involves the relationship between cellular barriers, $pK_a$ values of the LNPs, and structure of the LNPs. LNPs with low stability, cellular uptake, and hemolysis and subsequently low gene silencing were shown to possess low LNP $pK_a$ values (between 3 and 6; FIG. 4). The low LNP $pK_a$ values of some formulations can be predicted based on lipid structure. For example, lipid structures with electron-withdrawing groups neighboring the amine in the head group are weak bases (13, 20, 28, 29 and 30) and may thus lead to low LNP $pK_a$ values. Other formulations were less predictable. It was observed that structures with bulky head groups (4, 6, 21 and 24) also resulted in LNP formulations with low p$K_a$ values, which subsequently results in low gene silencing.

For the LNPs studied, correlations between their physicochemical properties and biological barriers led to the identification of LNP p$K_a$ as a determinant to the LNP's function and activity. The results also indicated that evaluation of multiple parameters associated with barriers to delivery such as siRNA entrapment, p$K_a$, LNP stability, cell uptake and hemolysis as a collective can serve as a reliable tool for pre-screening LNPs prior to in vivo use.

REFERENCES

1. Davis M E (2009) The First Targeted Delivery of siRNA in Humans via a Self-Assembling, Cyclodextrin Polymer-Based Nanoparticle: From Concept to Clinic. Mol Pharmaceutics 6:659-668.
2. Whitehead K A, Langer R, Anderson D G (2009) Knocking down barriers: advances in siRNA delivery. Nat Rev Drug Discov 8:129-138.
3. Akinc A et al., (2009) Development of Lipidoid-siRNA Formulations for Systemic Delivery to the Liver. Mol Ther 17:872-879.
4. Kumari A, Kumar V, Yadav S K (2011) Nanocarriers: a tool to overcome biological barriers in siRNA delivery. Expert Opin Biol Ther 11:1327-1339.
5. Santel A et al., (2006) A novel siRNA-lipoplex technology for RNA interference in the mouse vascular endothelium. Gene Ther 13:1222-1234.
6. Wang J, Lu Z, Wientjes M G, Au JL-S (2010) Delivery of siRNA therapeutics: barriers and carriers. AAPS J 12:492-503.
7. Rozema D B et al., (2007) Dynamic PolyConjugates for targeted in vivo delivery of siRNA to hepatocytes. Proc Natl Acad Sci USA 104:12982-12987.
8. Tang Y et al., (2012) Efficient in vitro siRNA delivery and intramuscular gene silencing using PEG-modified PAMAM dendrimers. Mol Pharmaceutics 9:1812-1821.
9. Alabi C, Vegas A, Anderson D (2012) Attacking the genome: emerging siRNA nanocarriers from concept to clinic. Curr Opin Pharmacol 12:1-7.
10. Zhang J, Fan H, Levorse D A, Crocker L S (2011) Interaction of cholesterol-conjugated ionizable amino lipids with biomembranes: lipid polymorphism, structure-activity relationship, and implications for siRNA delivery. Langmuir 27:9473-9483.
11. Zhang J, Fan H, Levorse D A, Crocker L S (2011) Ionization behavior of amino lipids for siRNA delivery: determination of ionization constants, SAR, and the impact of lipid pKa on cationic lipid-biomembrane interactions. Langmuir 27:1907-1914.
12. Philipp A, Zhao X, Tarcha P, Wagner E, Zintchenko A (2009) Hydrophobically Modified Oligoethylenimines as Highly Efficient Transfection Agents for siRNA Delivery. Bioconjugate Chem 20:2055-2061.
13. Jayaraman M et al., (2012) Maximizing the Potency of siRNA Lipid Nanoparticles for Hepatic Gene Silencing In vivo. Angew Chem Int Ed Engl 51:8529-8533.
14. Heyes J, Palmer L, Bremner K, MacLachlan I (2005) Cationic lipid saturation influences intracellular delivery of encapsulated nucleic acids. J Control Release 107:276-287.
15. Gratton S E A et al., (2008) The effect of particle design on cellular internalization pathways. Proc Natl Acad Sci USA 105:11613-11618.
16. Akinc A et al., (2008) A combinatorial library of lipid-like materials for delivery of RNAi therapeutics. Nat Biotechnol 26:561-569.
17. Love K T et al., (2010) Lipid-like materials for low-dose, in vivo gene silencing. Proc Natl Acad Sci USA 107: 1864-1869.
18. Akinc A et al., (2010) Targeted Delivery of RNAi Therapeutics With Endogenous and Exogenous Ligand-Based Mechanisms. Mol Ther 18:1357-1364.
19. Leuschner F et al., (2011) Therapeutic siRNA silencing in inflammatory monocytes in mice. Nat Biotechnol 29:1005-1010.
20. Novobrantseva T I et al., (2012) Systemic RNAi-mediated Gene Silencing in Nonhuman Primate and Rodent Myeloid Cells. Mol Ther Nucleic Acids 1:e4.
21. Semple S C et al., (2010) Rational design of cationic lipids for siRNA delivery. Nat Biotechnol 28:172-176.
22. A. Simon, Phase I Safety, Pharmacokinetic and Pharmacodynamic Results for ALN-PCS, Preliminary Study Results. (Alnylam Pharmaceuticals, Inc, 2012)
23. Trial to Evaluate Safety and Tolerability of ALN-PCS02 in Subjects With Elevated LDL-Cholesterol (LDL-C). (Registry of Federally and Privately Supported Clinical Trials, U.S. National Institutes of Health, 2011)
24. A Phase 1, Randomized, Single-blind, Placebo-Controlled, Single Ascending Dose, Safety, Tolerability and Pharmacokinetics Study of ALN-TTR02 in Healthy Volunteers (Alnylam Pharmaceuticals, 2012).
25. Hobo W et al., (2012) Improving dendritic cell vaccine immunogenicity by silencing PD-1 ligands using siRNA-lipid nanoparticles combined with antigen mRNA electroporation. Cancer Immunol Immunother.
26. Alabi C A et al., (2012) FRET-Labeled siRNA Probes for Tracking Assembly and Disassembly of siRNA-Nanocomplexes. ACS Nano 6:6133-6141.
27. Ruponen M et al., (2001) Extracellular glycosaminoglycans modify cellular trafficking of lipoplexes and polyplexes. J Biol Chem 276:33875-33880.
28. Ruponen M, Honkakoski P (2004) Cell-surface glycosaminoglycans inhibit cation-mediated gene transfer. J Gene Med 6:405-414.
29. Nguyen J, Szoka F C (2012) Nucleic Acid Delivery: The Missing Pieces of the Puzzle? Acc Chem Res 45:1153-1162.
30. Varkouhi A K, Scholte M, Storm G, Haisma H J (2011) Endosomal escape pathways for 27 delivery of biologicals. J Control Release 151:220-228.
31. Demaurex N (2002) pH homeostasis of cellular organelles. News in physiological sciences 17:1-5.
32. Bailey A L, Cullis P R (1994) Modulation of membrane fusion by asymmetric transbilayer distributions of amino lipids. Biochemistry 33:12573-12580.
33. Varga C M, Hong K, Lauffenburger D A (2001) Quantitative Analysis of Synthetic Gene Delivery Vector Design Properties. Mol Ther 4:438-446.
34. Bartlett D W, Davis M E (2006) Insights into the kinetics of siRNA-mediated gene silencing from live-cell and live-animal bioluminescent imaging. *Nucleic Acids Res* 34:322-333.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

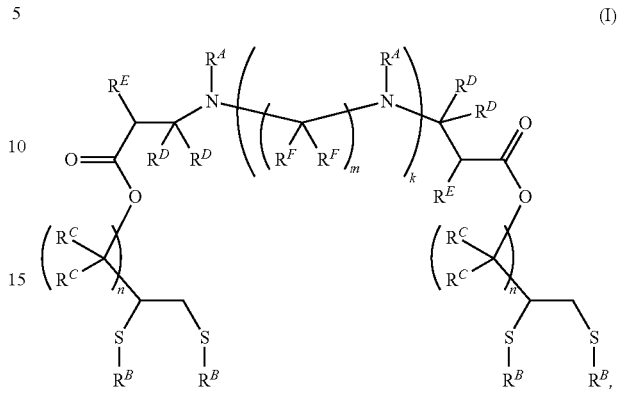

or a salt or stereoisomer thereof;
wherein:
each instance of $R^A$ is independently substituted or unsubstituted acyl, substituted or unsubstituted alkyl, substituted or unsubstituted alkenyl, substituted or unsubstituted heteroaliphatic, substituted or unsubstituted carbocyclyl, substituted or unsubstituted heterocyclyl, substituted or unsubstituted aryl, substituted or unsubstituted heteroaryl, or a nitrogen protecting group;
each instance of $R^B$ is independently substituted or unsubstituted alkyl, substituted or unsubstituted acyl, substituted or unsubstituted carbocyclyl, substituted or unsubstituted heterocyclyl, substituted or unsubstituted aryl, or substituted or unsubstituted heteroaryl;
each instance of $R^C$ is independently hydrogen, halogen, or substituted or unsubstituted $C_{1-6}$ alkyl;
each instance of $R^D$ is independently hydrogen, halogen, or substituted or unsubstituted $C_{1-6}$ alkyl;
each instance of $R^E$ is independently hydrogen, halogen, or substituted or unsubstituted $C_{1-6}$ alkyl;
each instance of $R^F$ is independently hydrogen, halogen, or substituted or unsubstituted $C_{1-6}$ alkyl;
k is 0 or 1;
m is 2, 3, 4, 5, or 6; and
each instance of n is independently 1, 2, 3, 4, 5, or 6.

2. The compound of claim 1, wherein the compound is of the formula:

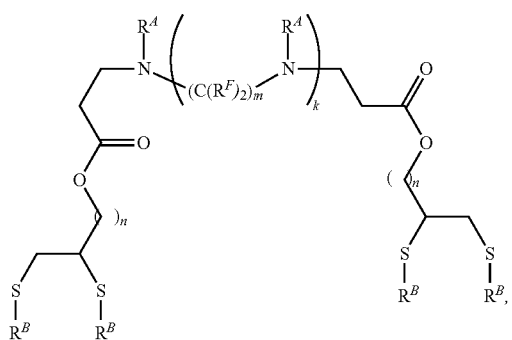

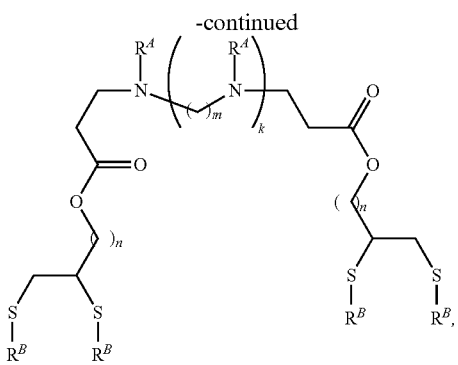

or a salt or stereoisomer thereof.

3. The compound of claim 1, wherein the compound is of the formula:

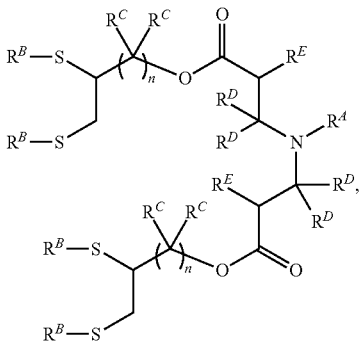

or a salt or stereoisomer thereof.

4. The compound of claim 1, wherein the compound is of the formula:

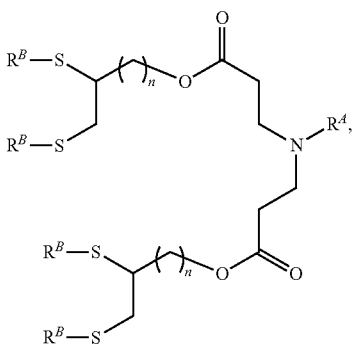

or a salt or stereoisomer thereof.

5. The compound of claim 1, wherein the compound is of the formula:

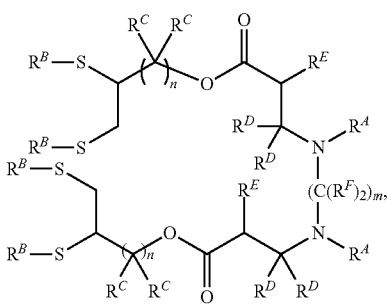

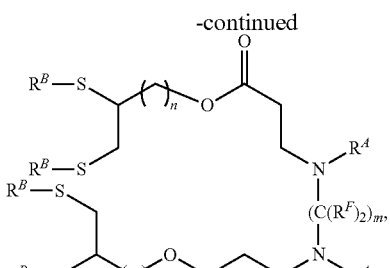

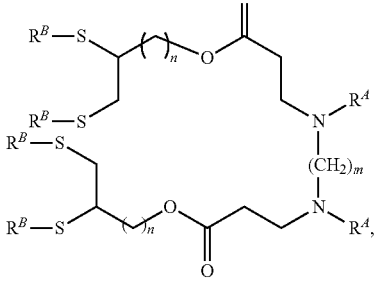

or a salt or stereoisomer thereof.

6. The compound of claim 1, wherein at least one instance of $R^A$ is substituted or unsubstituted alkyl.

7. The compound of claim 1, wherein:
at least one instance of $R^A$ is $C_{1-6}$ alkyl substituted with one or more substituents $R^{A1}$;
each instance of $R^{A1}$ is independently halogen, substituted or unsubstituted acyl, substituted or unsubstituted alkyl, substituted or unsubstituted alkenyl, substituted or unsubstituted heteroaliphatic, substituted or unsubstituted carbocyclyl, substituted or unsubstituted heterocyclyl, substituted or unsubstituted aryl, substituted or unsubstituted heteroaryl, or $-N(R^{A1a})_2$; and
each instance of $R^{A1a}$ is independently hydrogen, substituted or unsubstituted acyl, substituted or unsubstituted alkyl, substituted or unsubstituted alkenyl, substituted or unsubstituted carbocyclyl, substituted or unsubstituted heterocyclyl, substituted or unsubstituted aryl, substituted or unsubstituted heteroaryl, or a nitrogen protecting group, or two instances of $R^{A1a}$ are joined to form a substituted or unsubstituted heterocyclic ring.

8. The compound of claim 7, wherein at least one instance of $R^A$ is $C_{1-6}$ alkyl substituted with one or more substituents $R^{A1}$, wherein at least one instance of $R^{A1}$ is substituted or unsubstituted, 3- to 9-membered, monocyclic carbocyclyl including zero, one, or two double bonds in the carbocyclic ring.

9. The compound of claim 7, wherein at least one instance of $R^A$ is $C_{1-6}$ alkyl substituted with one or more substituents $R^{A1}$, wherein at least one instance of $R^{A1}$ is substituted or unsubstituted, 3- to 9-membered, monocyclic heterocyclyl, wherein one, two, or three atoms in the heterocyclic ring is independently selected from the group consisting of nitrogen, oxygen, or sulfur.

10. The compound of claim 7, wherein at least one instance of $R^A$ is $C_{1-6}$ alkyl substituted with one or more substituents $R^{A1}$, wherein at least one instance of $R^{A1}$ is substituted or unsubstituted, 5- to 6-membered, monocyclic heteroaryl, wherein one, two, three, or four atoms in the heteroaryl ring is independently selected from the group consisting of nitrogen, oxygen, or sulfur.

11. The compound of claim 7, wherein at least one instance of $R^A$ is $C_{1-6}$ alkyl substituted with one or more substituents $R^{A1}$, wherein at least one instance of $R^{A1}$ is substituted or unsubstituted, 9- to 10-membered, bicyclic heteroaryl, wherein one, two, three, or four atoms in the heteroaryl ring is independently selected from the group consisting of nitrogen, oxygen, or sulfur.

12. The compound of claim 7, wherein at least one instance of $R^A$ is $C_{1-6}$ alkyl substituted with one or more substituents $R^{A1}$, wherein at least one instance of $R^{A1}$ is $-N(R^{A1a})_2$.

13. The compound of claim 1, wherein at least one instance of $R^A$ is substituted or unsubstituted, 3- to 9-membered, monocyclic heterocyclyl including zero, one, or two double bonds in the heterocyclic ring, wherein one, two, or three atoms in the heterocyclic ring are independently selected from the group consisting of nitrogen, oxygen, and sulfur.

14. The compound of claim 1, wherein at least one instance of $R^A$ is unsubstituted $C_{1-6}$ alkyl.

15. The compound of claim 1, wherein at least one instance of $R^B$ is substituted or unsubstituted alkyl.

16. The compound of claim 1, wherein all instances of $R^C$ are hydrogen.

17. A method of preparing a compound of claim 1, or a salt or stereoisomer thereof, the method comprising:

(a) reacting a compound of Formula (A), or a salt thereof, with a compound of Formula (B), or a salt thereof, to provide a compound of Formula (C), or a salt thereof:

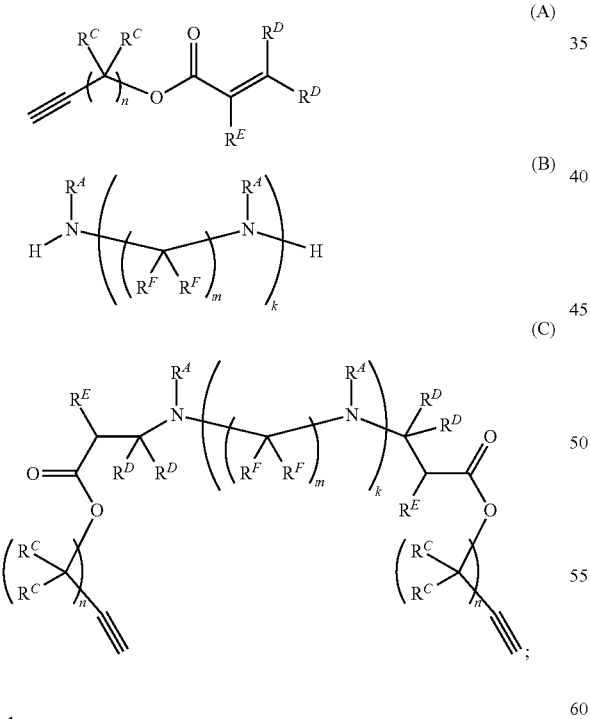

and (b) reacting the compound of Formula (C), or a salt thereof, with a compound of Formula (D), or a salt thereof, to provide the compound of claim 1, or the salt or stereoisomer thereof:

$R^B$—SH (D).

18. A composition comprising:
a compound of claim 1, or a salt thereof;
an agent; and
optionally an excipient.

19. A method of delivering an agent to a subject or cell, the method comprising administering to the subject or contacting the cell with a composition of claim 18.

20. The compound of claim 1, wherein the compound of Formula (I) is a compound of Formula (I-B-3) or Formula (I-C-3):

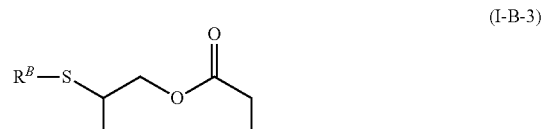

(I-B-3)

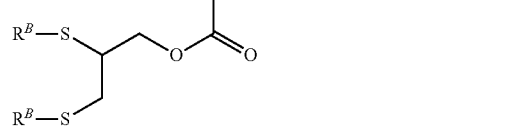

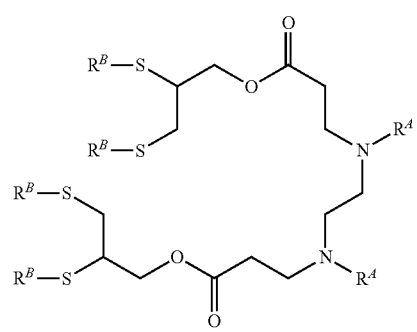

(I-C-3)

or a salt or stereoisomer thereof.

21. The The compound of claim 1, wherein at least one instance of $R^A$ is of the formula:

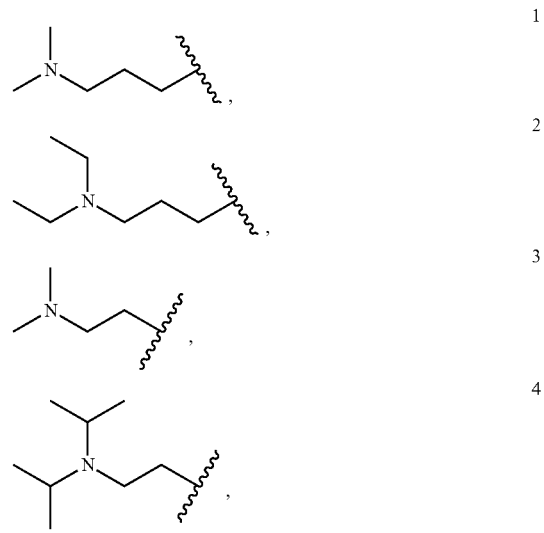

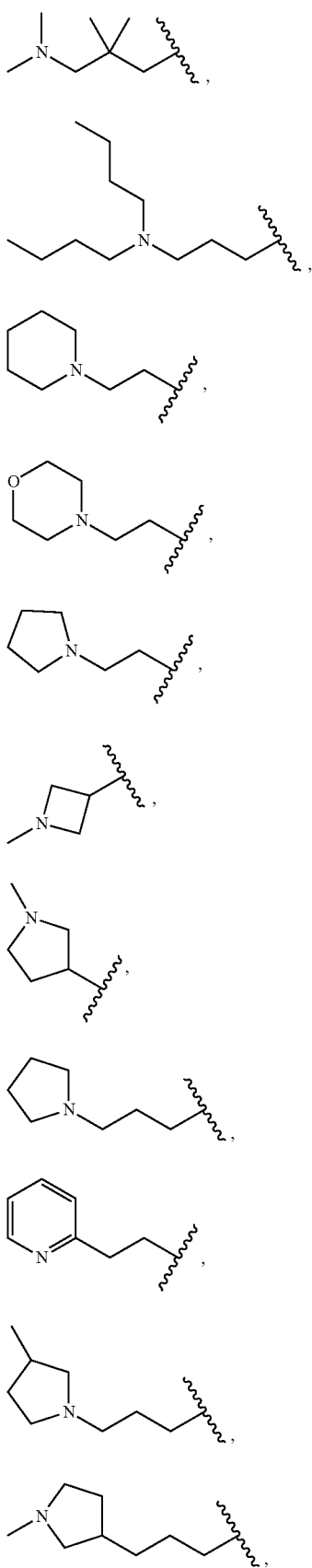
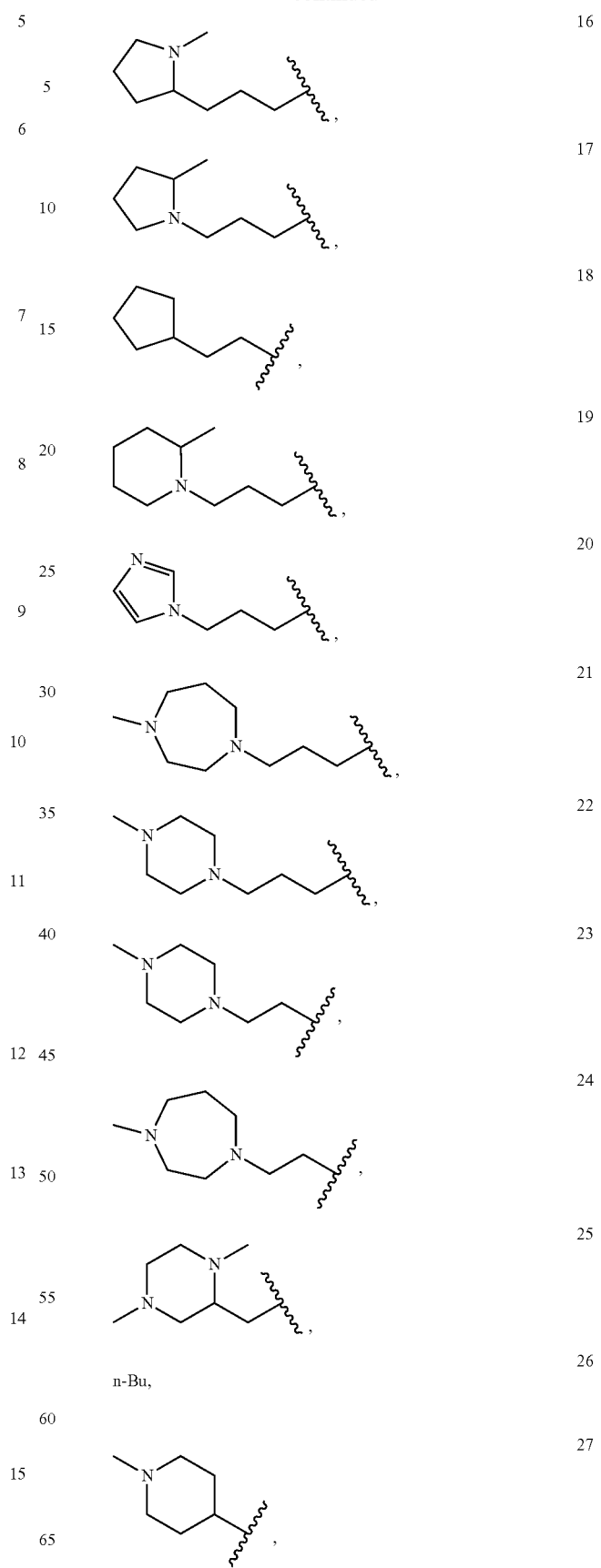

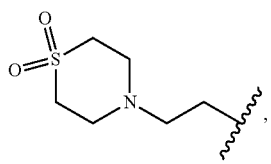
28
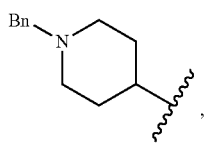
29
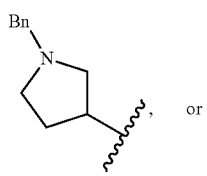
30
, or
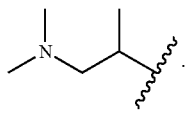
31
22. The compound of claim 1, wherein at least one instance of $R^B$ is unsubstituted or substituted $C_{6-18}$ alkyl.
23. The compound of claim 1, wherein at least one instance of $R^B$ is unsubstituted $C_{6-12}$ alkyl.
24. The compound of claim 1, wherein the compound of Formula (I) is a compound of Formula (I-B-3):
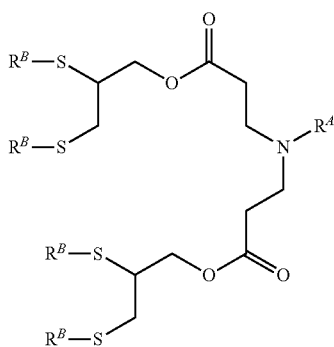
(I-B-3)
or a salt or stereoisomer thereof;
whererin $R^A$ is of the formula:
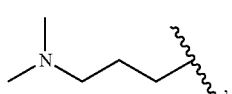
1
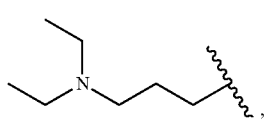
2
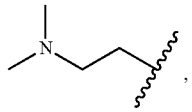
3
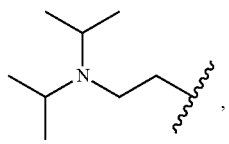
4
5
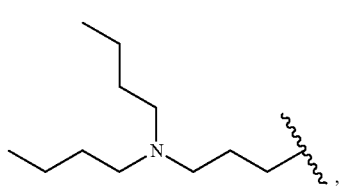
6
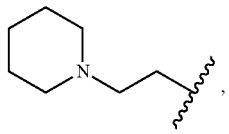
7
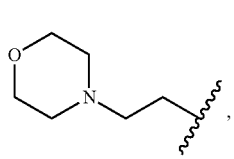
8
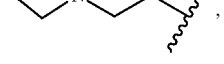
9
10
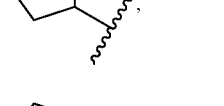
11
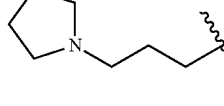
12
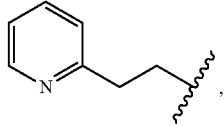
13

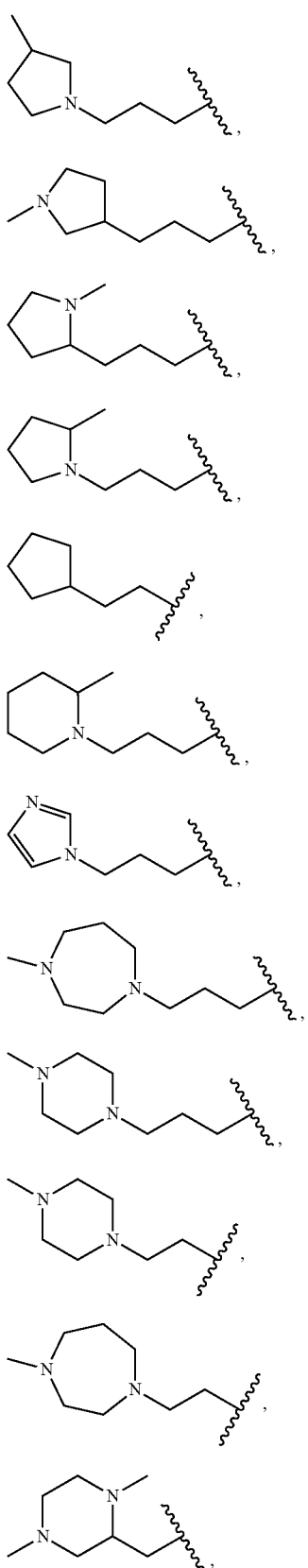

n-Bu,

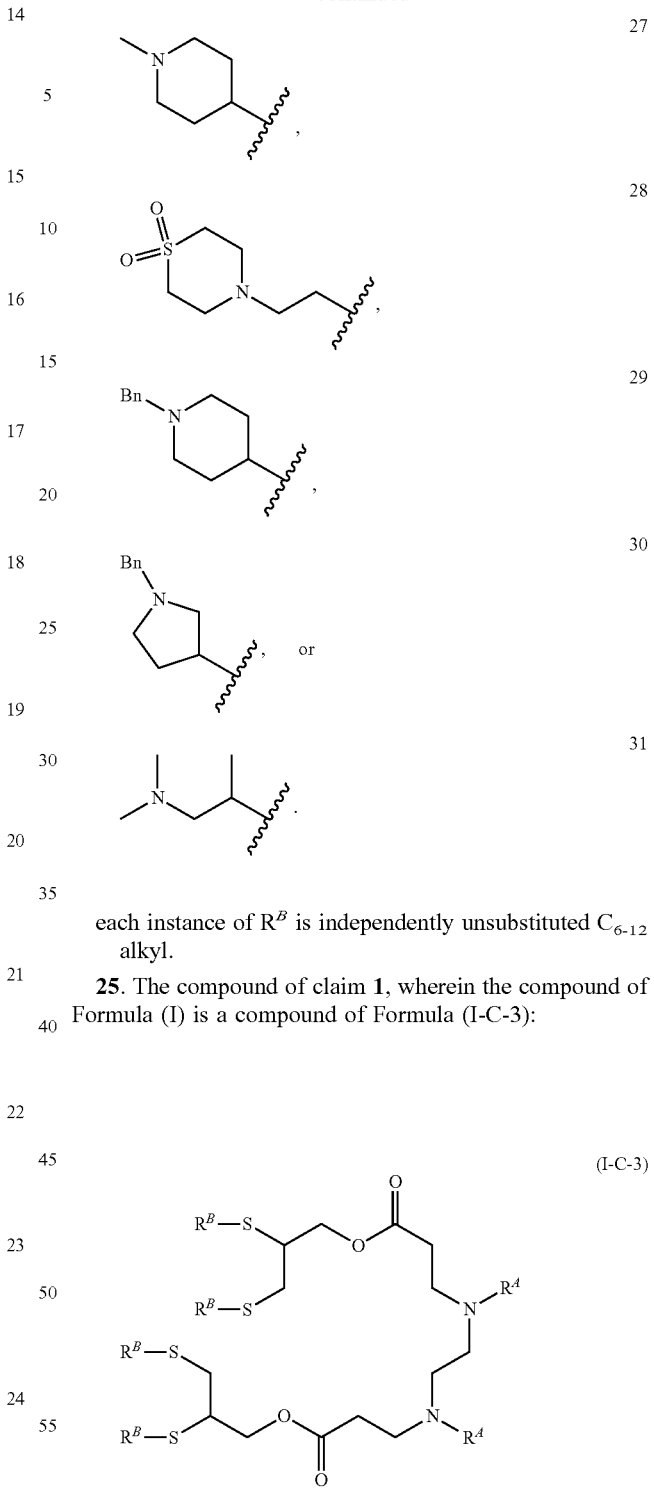

each instance of $R^B$ is independently unsubstituted $C_{6-12}$ alkyl.

25. The compound of claim 1, wherein the compound of Formula (I) is a compound of Formula (I-C-3):

(I-C-3)

or a salt or stereoisomer thereof;
wherein each instance of $R^A$ is independently substituted or unsubstituted $C_{1-6}$ alkyl; and
each instance of $R^B$ is independently unsubstituted $C_{6-12}$ alkyl.

26. The method of claim 17, wherein the compound of Formula (I) is a compound of Formula (I-B-3):

(I-B-3)
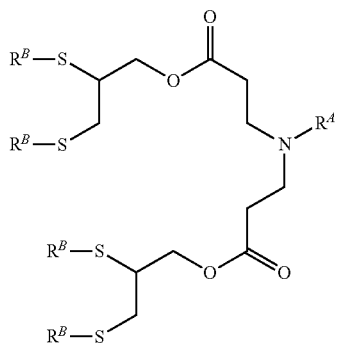
or a salt or stereoisomer thereof;
wherein $R^A$ is of the formula:
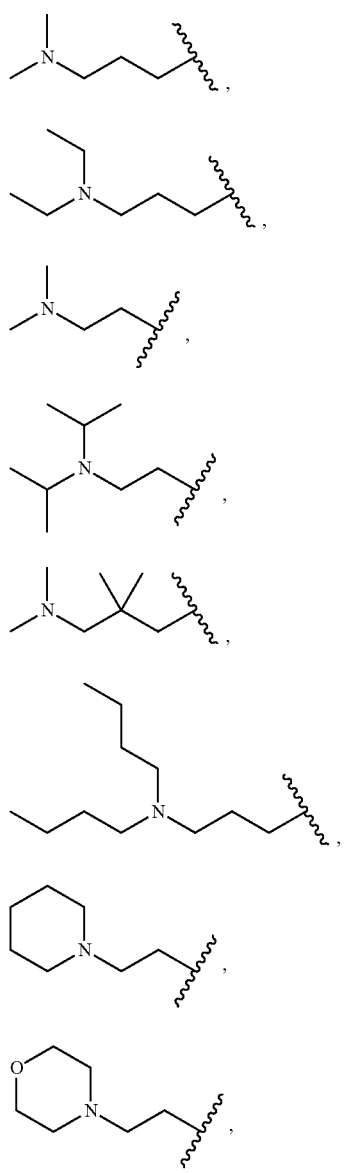
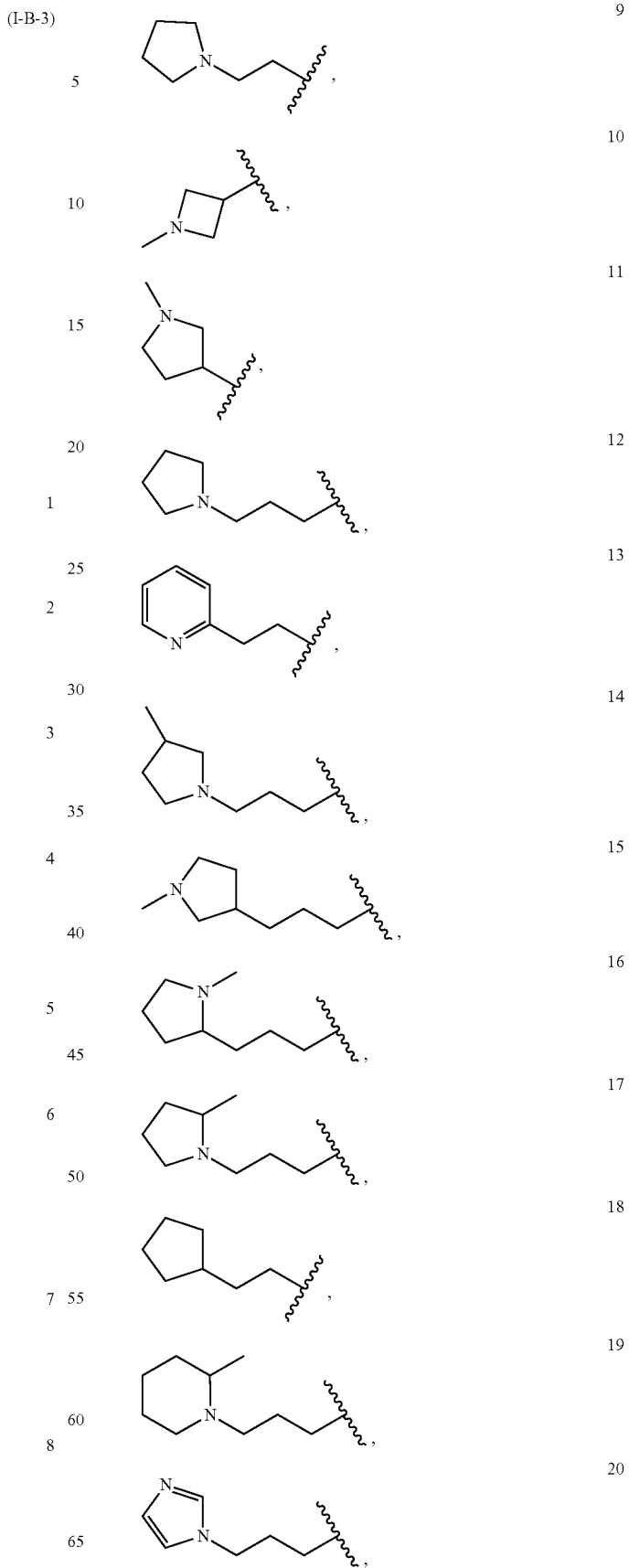

-continued

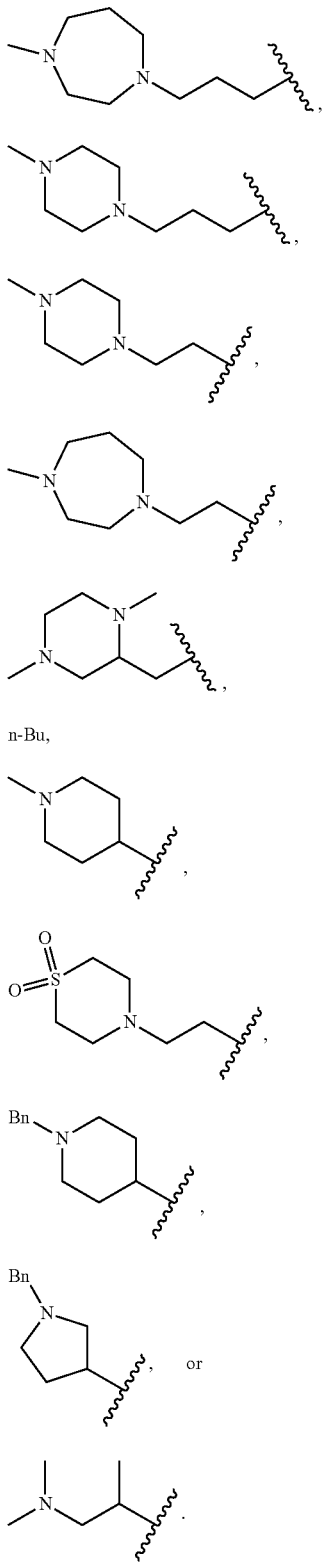

n-Bu, each instance of $R^B$ is independently unsubstituted $C_{6-12}$ alkyl.

27. The method of claim 17, wherein the compound of Formula (I) is a compound of Formula (I-C-3):

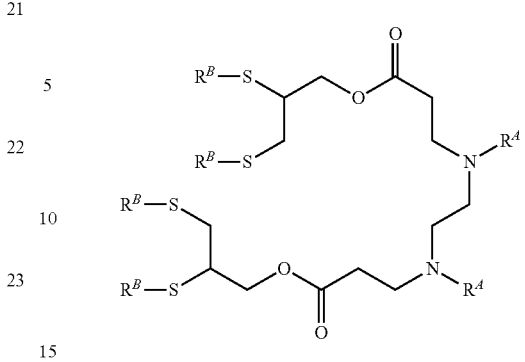
(I-C-3)

or a salt or stereoisomer thereof;

wherein each instance of $R^A$ is independently substituted or unsubstituted $C_{1-6}$ alkyl; and each instance of $R^B$ is independently unsubstituted $C_{6-12}$ alkyl.

28. The composition of claim 18, wherein the compound of Formula (I) is a compound of Formula (I-B-3):

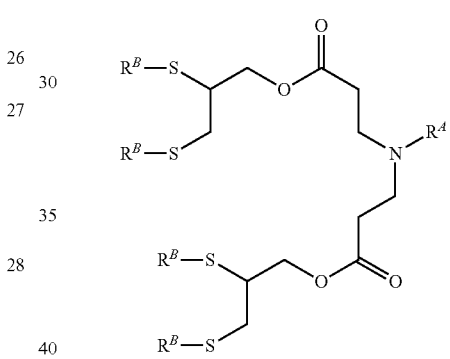
(I-B-3)

or a salt or stereoisomer thereof;

wherein $R^A$ is of the formula:

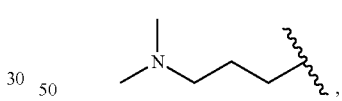
1

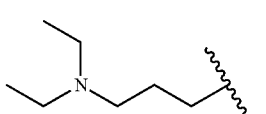
2

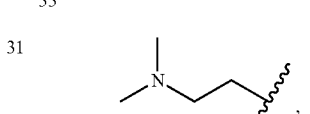
3

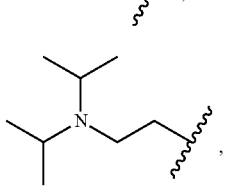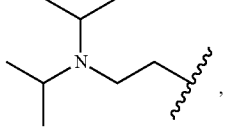
4

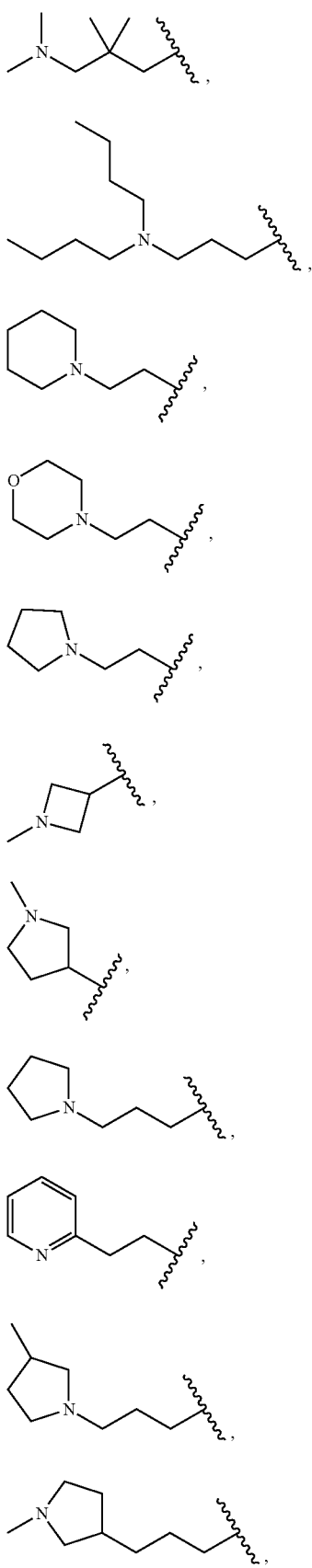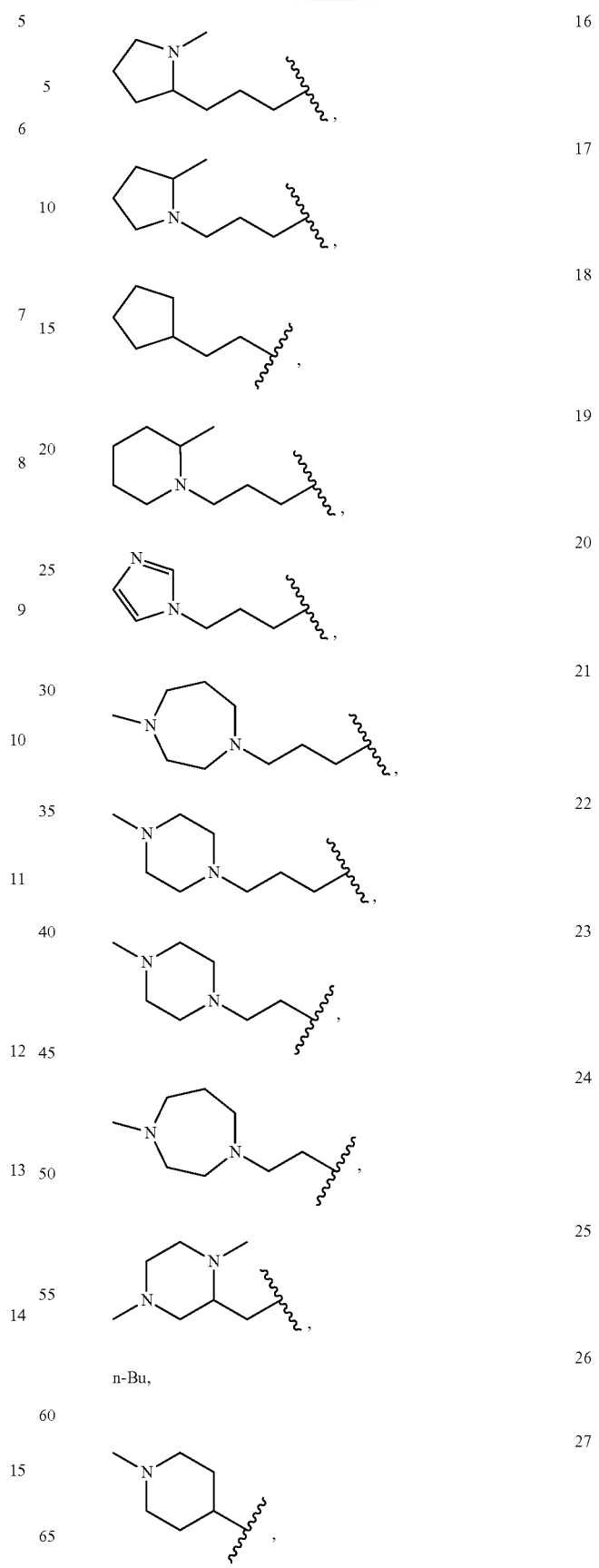

-continued

28
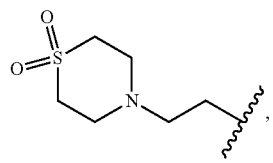,

29
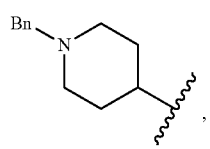,

30
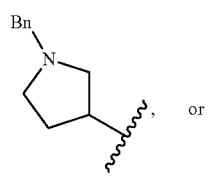 or

31
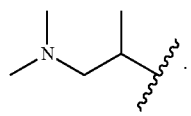.

each instance of $R^B$ is independently unsubstituted $C_{6-12}$ alkyl.

29. The composition of claim 18, wherein the compound of Formula (I) is a compound of Formula (I-C-3):

(I-C-3)
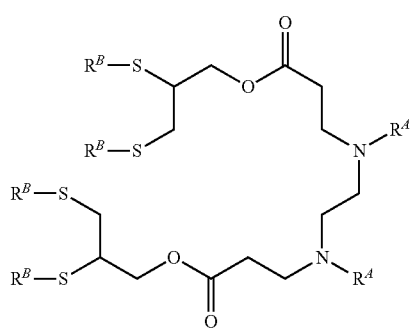

or a salt or stereoisomer thereof;
wherein each instance of $R^A$ is independently substituted or unsubstituted $C_{1-6}$ alkyl; and
each instance of $R^B$ is independently unsubstituted $C_{6-12}$ alkyl.

30. The composition of claim 18, wherein the agent is a polynucleotide, peptide, protein, or small molecule.

31. The composition of claim 30, wherein the agent is a polynucleotide.

32. The composition of claim 31, wherein the polynucleotide is siRNA, mRNA, or plasmid DNA.

33. The method of claim 19, wherein the compound of Formula (I) is a compound of Formula (I-B-3):

(I-B-3)
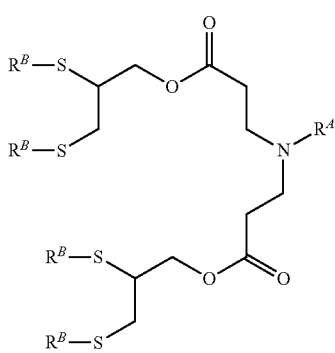

or a salt or stereoisomer thereof;
wherein $R^A$ is of the formula:

1
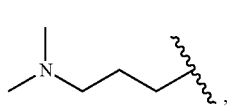,

2
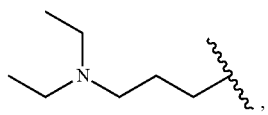,

3
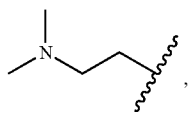,

4
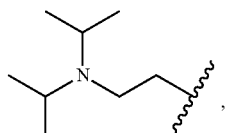,

5
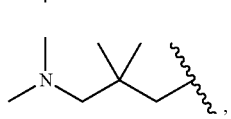,

6
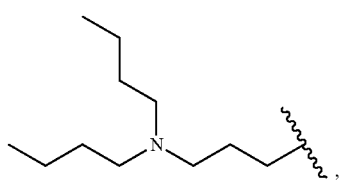,

7
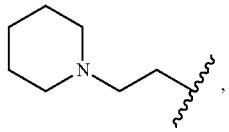,

8
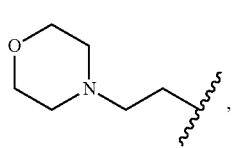,

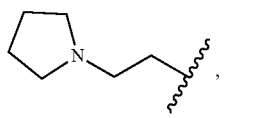
9,
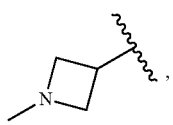
10,
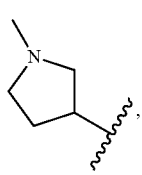
11,
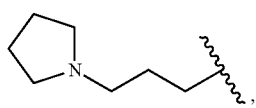
12,
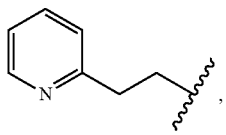
13,
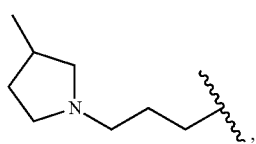
14,
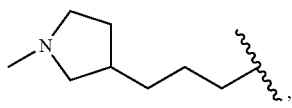
15,
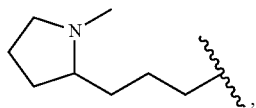
16,
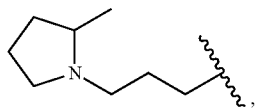
17,
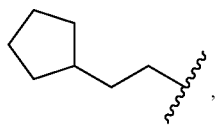
18,
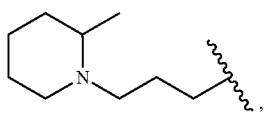
19,
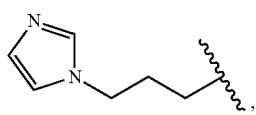
20,
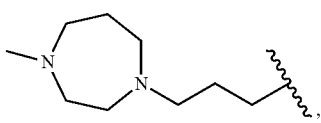
21,
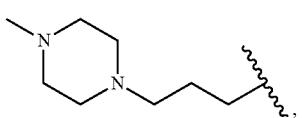
22,
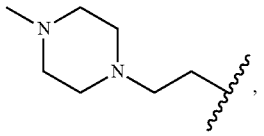
23,
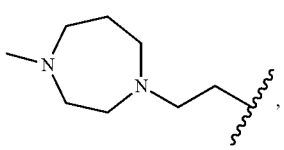
24,
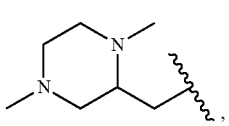
25,
n-Bu, 26
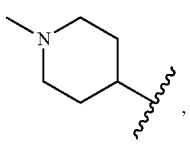
27,
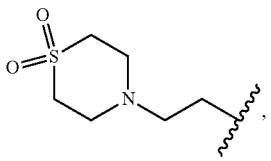
28,
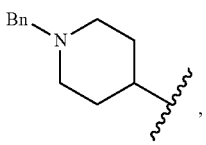
29,
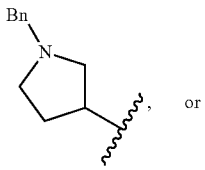
30, or
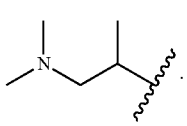
31.
each instance of $R^B$ is independently unsubstituted $C_{6-12}$ alkyl.
34. The method of claim 19, wherein the compound of Formula (I) is a compound of Formula (I-C-3):

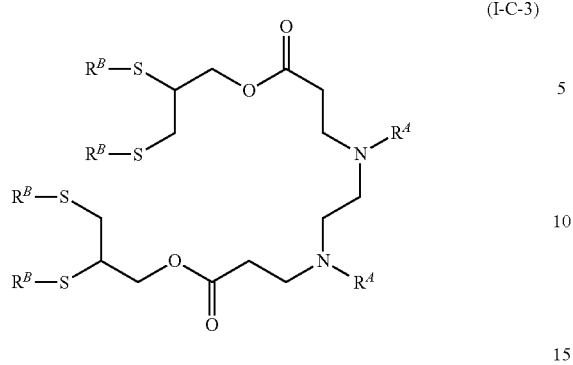
(I-C-3)
or a salt or stereoisomer thereof;
wherein each instance of $R^A$ is independently substituted or unsubstituted $C_{1-6}$ alkyl; and
each instance of $R^B$ is independently unsubstituted $C_{6-12}$ alkyl.
* * * * *